US011118016B2

(12) United States Patent
Owen et al.

(10) Patent No.: US 11,118,016 B2
(45) Date of Patent: Sep. 14, 2021

(54) THERAPEUTIC DENDRIMER

(71) Applicant: Starpharma Pty Ltd., Abbotsford (AU)

(72) Inventors: David Owen, Abbortsford (AU); Brian Devlin Kelly, Abbotsford (AU)

(73) Assignee: Starpharma Pty Ltd., Abbotsford (AU)

( * ) Notice: Subject to any disclaimer, the term of this patent is extended or adjusted under 35 U.S.C. 154(b) by 0 days.

(21) Appl. No.: 17/003,699

(22) Filed: Aug. 26, 2020

(65) Prior Publication Data

US 2020/0392295 A1 Dec. 17, 2020

Related U.S. Application Data

(63) Continuation of application No. 16/933,354, filed on Jul. 20, 2020, now abandoned, which is a continuation of application No. PCT/AU2019/050759, filed on Jul. 19, 2019.

(30) Foreign Application Priority Data

Jul. 19, 2018 (AU) ................................ 2018902611

(51) Int. Cl.
| | | |
|---|---|---|
| *C08G 83/00* | (2006.01) | |
| *A61K 47/12* | (2006.01) | |
| *A61K 47/26* | (2006.01) | |
| *A61K 9/00* | (2006.01) | |

(52) U.S. Cl.
CPC ............ *C08G 83/003* (2013.01); *A61K 47/12* (2013.01); *A61K 47/26* (2013.01); *A61K 9/0019* (2013.01)

(58) Field of Classification Search
CPC ...... C08G 83/003; A61K 47/12; A61K 47/26; A61K 9/0019
See application file for complete search history.

(56) References Cited

U.S. PATENT DOCUMENTS

| | | | |
|---|---|---|---|
| 5,840,900 A | 11/1998 | Greenwald et al. | |
| 8,703,907 B2 | 4/2014 | Ashley et al. | |
| 8,754,190 B2 | 6/2014 | Ashley et al. | |
| 8,946,405 B2 | 2/2015 | Ashley et al. | |
| 9,387,254 B2 | 7/2016 | Santi et al. | |
| 9,744,246 B2 | 8/2017 | Owen et al. | |
| 10,265,409 B2 | 4/2019 | Owen et al. | |
| 2009/0324535 A1 | 12/2009 | Boyd et al. | |
| 2010/0136614 A1 | 6/2010 | Luo et al. | |
| 2010/0247668 A1* | 9/2010 | Eliasof .................. | A61P 35/00 424/501 |
| 2014/0171375 A1* | 6/2014 | Owen .................. | C08G 83/003 514/19.3 |
| 2014/0296257 A1* | 10/2014 | Hersel .................. | A61K 31/428 514/259.41 |

FOREIGN PATENT DOCUMENTS

| | | |
|---|---|---|
| CN | 101420962 A | 4/2009 |
| CN | 102120036 A | 7/2011 |
| DE | 10041559 A1 | 3/2002 |
| WO | 2001/07348 A1 | 2/2001 |
| WO | 2001/049696 A1 | 7/2001 |
| WO | 2003/055935 A1 | 7/2003 |
| WO | 2007/048190 A1 | 5/2007 |
| WO | 2007/080114 A2 | 7/2007 |
| WO | 2007/082331 A1 | 7/2007 |
| WO | 2008/017122 A1 | 2/2008 |
| WO | 2008/017125 A1 | 2/2008 |
| WO | 2011/072290 A2 | 6/2011 |
| WO | 2011/140376 A1 | 11/2011 |
| WO | 2012/167309 A1 | 12/2012 |
| WO | 2014/036323 A1 | 3/2014 |
| WO | 2015/035446 A1 | 3/2015 |
| WO | 2015/184510 A1 | 12/2015 |

OTHER PUBLICATIONS

Patricia Vrignaud, et al, Preclinical Antitumor Activity of Cabazitaxel, a Semisynthetic Taxane Active in Taxane-resistant Tumors, 19 Clin. Cancer Res. 2973 (Year: 2013).*
Emily Girard, et al, Efficacy of Cabazitaxel in Mouse Models of Pediatric Brain Tumors, 17 Neuro-Oncology 107 (Year: 2015).*
Ansell et al., Modulating the therapeutic activity of nanoparticle delivered paclitaxel by manipulating the hydrophobicity of prodrug conjugates. J Med Chem. Jun. 2008;51(11):3288-96.
Bhadra et al., PEGylated peptide dendrimeric carriers for the delivery of antimalarial drug chloroquine phosphate. Pharma Res. Mar. 2006;23(3):623-33.
Bi et al., Multifunctional poly(amidoamine) dendrimer-taxol conjugates: synthesis, characterisation, and stability. J Comput Theor Nanosci. 2007;4(6):1179-87.
Cline et al., Paclitaxel-conjugated Pamam dendrimers adversely affect microtubule structure through two independent modes of action. Biomacromolecules. Mar. 2013;14(3):654-64.
De Bono et al., Prednisone plus cabazitaxel or mitoxantrone for metastatic castration-resistant prostate cancer progressing after docetaxel treatment: A randomised open-label trial. Lancet. Oct. 2010;376(9747):1147-54.
Fox et al., Synthesis and in vivo antitumor efficacy of PEGylated poly (I-lysine) dendrimer-camptothecin conjugates. Mol Pharm. Sep.-Oct. 2009;6(5):1562-72.
Kaminskas et al., Capping methotrexate alpha-carboxyl groups enhances systemic exposure and retains the cytotoxicity of drug conjugated PEGylated polylysine dendrimers, Mol Pharm. Apr. 2011;8(2):338-49.

(Continued)

*Primary Examiner* — Sean M Basquill
(74) *Attorney, Agent, or Firm* — McCarter & English, LLP; Yu Lu; Gina M. Stewart

(57) ABSTRACT

Provided herein are dendrimers comprising: a core unit, five generations of building units which are lysine residues or analogues thereof, first terminal groups comprising a cabazitazel residue covalently attached to a diglycolyl linker group, and second terminal groups comprising a PEG group. Also provided herein are pharmaceutical compositions comprising the dendrimers, and methods and uses of the dendrimers in therapy of disorders such as cancers. Processes for making the dendrimers and intermediates are also provided.

18 Claims, 6 Drawing Sheets

(56) References Cited

OTHER PUBLICATIONS

Kaminskas et al., Doxorubicin-conjugated PEGylated dendrimers show similar tumoricidal activity but lower systemic toxicity when compared to PEGylated liposome and solution formulations in mouse and rat tumor models. Mol Pharm. Mar. 2012;9(3):422-32.

Kaminskas et al., Partly-PEGylated poly-L-lysine dendrimers have reduced plasma stability and circulation times compared with fully PEGylated dendrimers. J Pharm Sci. Oct. 2009;98(10):3871-5.

Kaminskas et al., Pulmonary administration of a doxorubicin-conjugated dendrimer enhances drug exposure to lung metastases and improves cancer therapy. J Control Release. Jun. 2014;183:18-26.

Kaminskas et al., The impact of molecular weight and PEG chain length on the systemic pharmacokinetics of PEGylated poly-l-lysine dendrimers. Mol Pharm. May-Jun. 2008;5(3):449-63.

Kapp et al., Platinum(II)-dendrimer conjugates: synthesis and investigations on cytotoxicity, cellular distribution, platinum release, DNA and protein binding. Bioconjug Chem. Feb. 2010;21(2):328-37.

Lim et al., Design, synthesis, characterisation and biological evaluation of triazine dendrimers bearing paclitaxel using ester and ester/disulfide linkages. Bioconjug Chem. Nov. 2009;20(11):2154-61.

Matsumoto et al., Controlled drug release: new water-soluble prodrugs of an HIV protease inhibitor. Bioorg Med Chem Lett. Feb. 2001;11(4):605-9.

Mita et al., Phase I and pharmacokinetic study of XRP6258 (RPR 116258A), a novel taxane, administered as a 1-hour infusion every 3 weeks in patients with advanced solid tumors. Clin Cancer Res. 2009;15(2):723-30.

Ojima et al., Tumor-specific novel taxoid-monoclonal antibody conjugates. J Med Chem. Dec. 2002;45(26):5620-3.

Sugahara et al., Paclitaxel delivery systems: The use of amino acid linkers in the conjugations of paclitaxel with carboxymethyldextran to create prodrugs. Biol Pharm Bull. May 2002;25(5):632-41.

Venditto et al., Cancer therapies utilizing the camptothecins: a review of the in vivo literature. Mol Pharm. Apr. 2010;7(2):307-49.

Vrignaud et al., Preclinical profile of cabazitaxel. Drug Des Devel Ther. Oct. 2014;8:1851-67.

Yellepeddi et al., Biotinylated PAMAM dendrimers for intracellular delivery of cisplatin to ovarian cancer: Role of SMVT. Anticancer Res. Mar. 2011;31(3):897-906.

Zhu et al., PEGylated PAMAM Dendrimer-doxorubicin conjugates: in vitro evaluation and in vivo tumor accumulation. Pharm Res. Jan. 2010;27(1):161-74.

International Search Report and Written Opinion for Application No. PCT/AU2019/050759, dated Aug. 23, 2019, 11 pages.

\* cited by examiner

THERAPEUTIC DENDRIMER

REFERENCE TO RELATED APPLICATION

This application is a continuation application of U.S. patent application Ser. No. 16/933,354, filed Jul. 20, 2020, which is a continuation of International Patent Application No. PCT/AU2019/050759, filed on Jul. 19, 2019, published as WO 2020/014750 A1, which claims the benefit of the filing date of Australian Patent Application No. 2018902611, filed on Jul. 19, 2018, the entire contents of each of the above applications are incorporated herein by reference.

FIELD OF THE INVENTION

The present disclosure generally relates to drug-dendrimer conjugates comprising a dendrimer including a core and building units, the outermost generation of building units including one or more pharmaceutically active agents attached via a cleavable linker group. The present disclosure also relates to pharmaceutical compositions and methods of treatment comprising the drug-dendrimer conjugates, and to processes and synthetic intermediates for producing the drug-dendrimer conjugates.

BACKGROUND OF THE INVENTION

There are a number of difficulties associated with the formulation and delivery of pharmaceutically active agents including poor aqueous solubility, toxicity, low bioavailability, instability under biological conditions, lack of targeting to the site of action, and rapid in vivo degradation.

To combat some of these difficulties, pharmaceutically active agents may be formulated with solubilising agents which themselves may cause side effects such as hypersensitivity and may require premedication to reduce these side effects. Alternative approaches include encapsulation of the pharmaceutically active agent in liposomes, micelles or polymer matrices or attachment of the pharmaceutically active agent to liposomes, micelles and polymer matrices.

Although these approaches may improve some of the problems associated with the formulation and delivery of pharmaceutically active agents, many still have drawbacks.

Oncology drugs can be particularly difficult to formulate and have side effects that may limit the dosage amount and regimen that can be used for treatment. This can result in reduced efficacy of the treatment. For example, taxane drugs such as cabazitaxel have low aqueous solubility, but also a relatively narrow therapeutic window, and so increasing concentration of the agent by, for example, using solubilisation excipients can result in associated toxicity issues.

The use of liposomes, micelles and polymer matrices as carriers, either encapsulating or having the pharmaceutical agent attached, while allowing solubilisation of the pharmaceutically active agent and in some cases improved bioavailability and reduced toxicity, present difficulties in relation to release of the pharmaceutically active agent. In some cases, the carrier degrades rapidly releasing the pharmaceutically active agent before it has reached the target organ. In other cases, the release of the pharmaceutically active agent from the carrier is slowed to the extent that a therapeutic dose of drug in the body or in the target organ may not be attained. Further, such compositions may present stability and manufacturing challenges.

Therefore, there is a need for alternative formulations and delivery means for delivering drugs to reduce side effects, improve dosage regimens and improved therapeutic window, which may lead to better compliance and efficacy of a drug for patients, while being stable, and practical to manufacture, and having a generally homogenous composition.

SUMMARY OF THE INVENTION

The subject matter of the present disclosure is predicated in part on the surprising discovery that cabazitaxel, when conjugated to a dendrimer, provides improved efficacy and/or pharmacokinetic properties of the drug.

Accordingly, in a first aspect there is provided a dendrimer comprising:
 i) a core unit (C); and
 ii) building units (BU), each building unit being a lysine residue or an analogue thereof;
wherein the core unit is covalently attached to two building units via amide linkages, each amide linkage being formed between a nitrogen atom present in the core unit and the carbon atom of an acyl group present in a building unit;
 the dendrimer being a five generation building unit dendrimer;
wherein building units of different generations are covalently attached to one another via amide linkages formed between a nitrogen atom present in one building unit and the carbon atom of an acyl group present in another building unit;
 the dendrimer further comprising:
 iii) a plurality of first terminal groups (T1) each comprising a cabazitaxel residue covalently attached to a diglycolyl linker group; and
 iv) a plurality of second terminal groups (T2) each comprising a PEG group;
wherein at least one third of the nitrogen atoms present in outer building units are each covalently attached to a first terminal group; and
 at least one third of the nitrogen atoms present in outer building units are each covalently attached to a second terminal group;
or a pharmaceutically acceptable salt thereof.

In some embodiments, the core is:

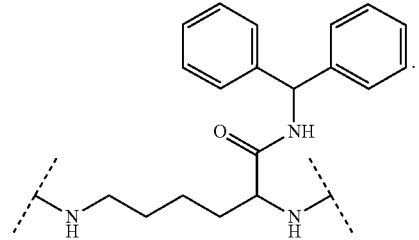

In some embodiments, the building units are each:

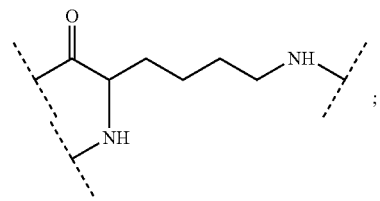

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group.

In some embodiments, the building units are each:

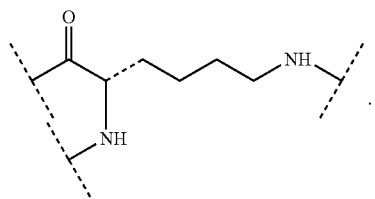

In some embodiments, the dendrimer has five complete generations of building units.

In some embodiments, each first terminal group (T1) is:

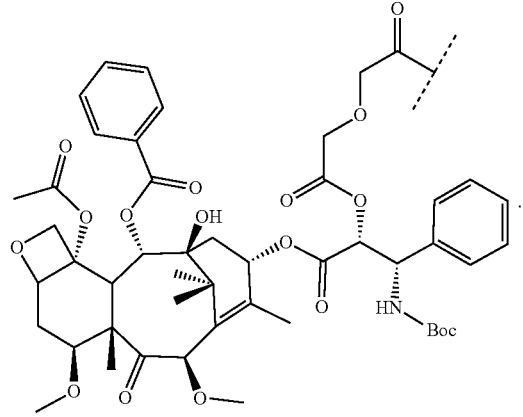

In some embodiments, the second terminal groups comprise PEG groups having an average molecular weight in the range of from 1000 to 2500 Daltons.

In some embodiments, the second terminal groups each comprise a PEG group covalently attached to a PEG linking group (L1) via an ether linkage formed between a carbon atom present in the PEG group and an oxygen atom present in the PEG linking group, and each second terminal group is covalently attached to a building unit via an amide linkage formed between a nitrogen atom present in a building unit and the carbon atom of an acyl group present in the PEG linking group.

In some embodiments, the second terminal groups are each

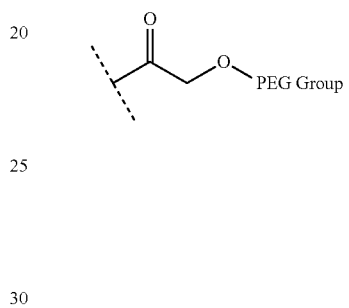

and the PEG group is a methoxy-terminated PEG having an average molecular weight in the range of from about 1750 to 2500 Daltons.

In some embodiments, the dendrimer comprises surface units comprising an outer building unit attached to a first terminal group and a second terminal group, the surface units having the structure:

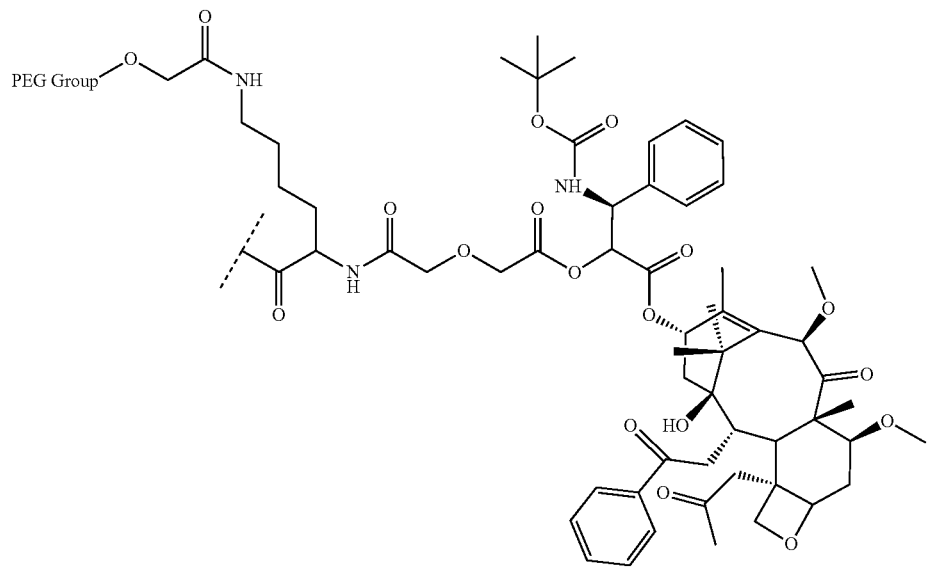

and wherein the PEG group is a methoxy-terminated PEG having an average molecular weight in the range of from about 1750 to 2500 Daltons.

In some embodiments, the dendrimer has from 28 to 32 surface units, preferably from 30 to 32 surface units.

In some embodiments, at least 40% of the nitrogen atoms present in the outer building units are each covalently attached to a first terminal group; and at least 40% of the nitrogen atoms present in the outer building units are each covalently attached to a second terminal group.

In some embodiments, the five generations of building units are complete generations, and the outer generation of building units provides 64 nitrogen atoms for covalent attachment to a first terminal group or a second terminal, wherein from 26 to 32 first terminal groups are covalently attached to one of said nitrogen atoms, and wherein from 28 to 32 second terminal groups are each covalently attached to one of said nitrogen atoms.

In some embodiments, the cabazitaxel residues comprise a w/w % of the dendrimer in the range of from 23% w/w to 28% w/w.

In some embodiments, the dendrimer is:

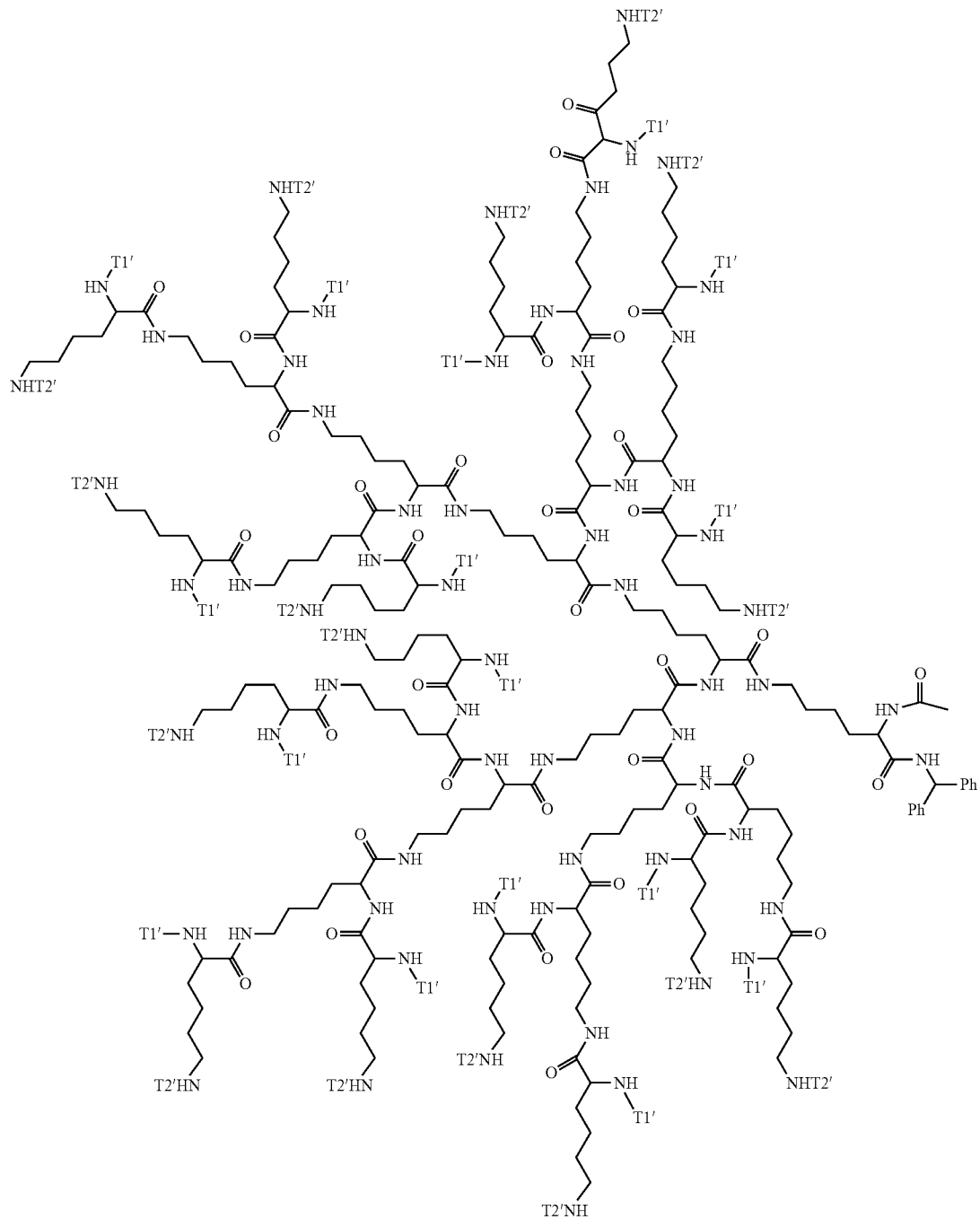

-continued
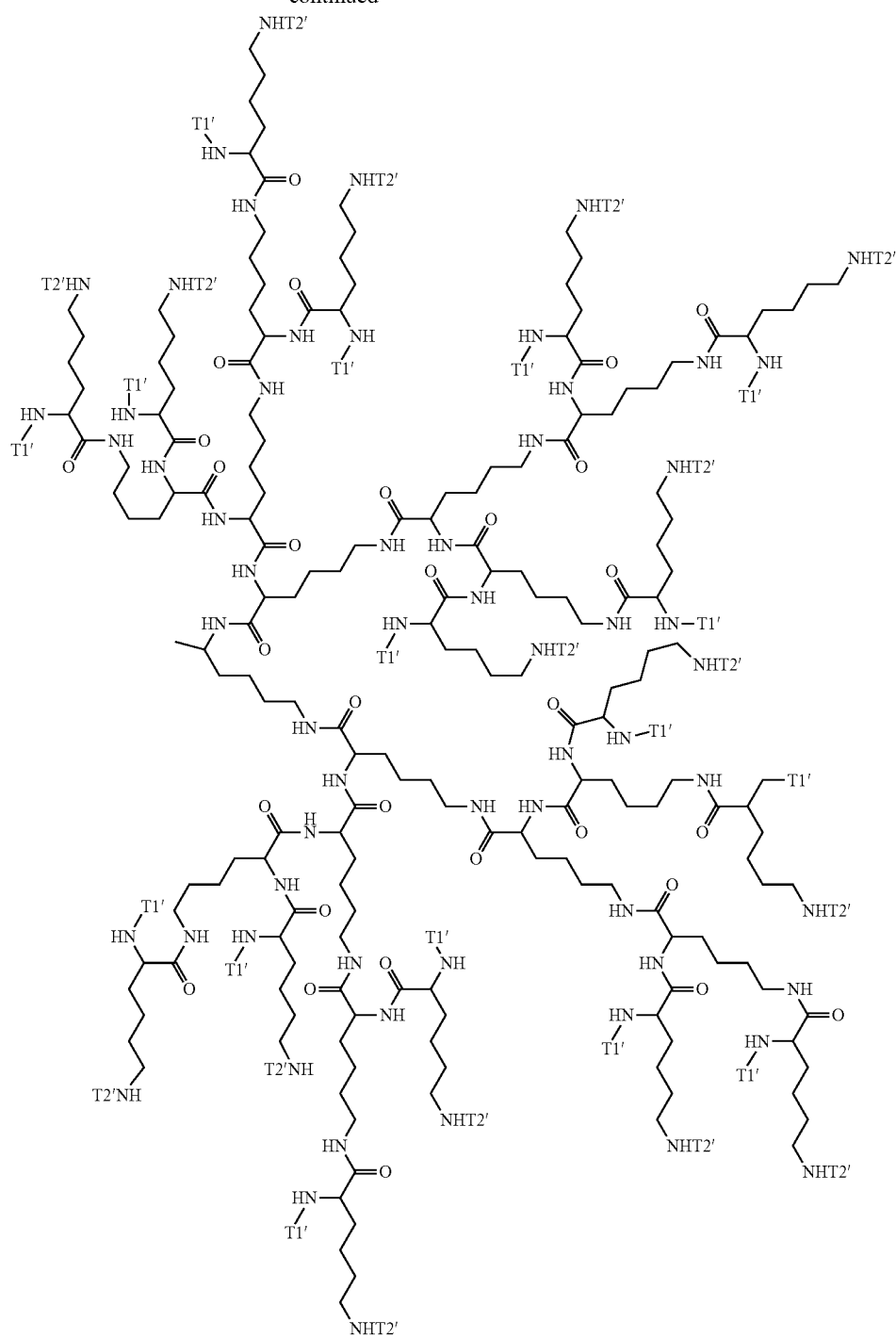

in which T1' represents a first terminal group which is

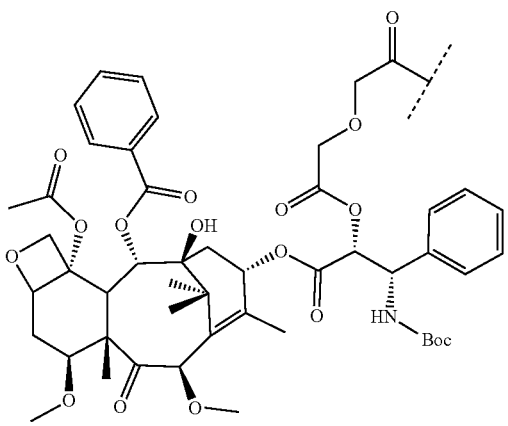

or T1' represents H, wherein less than 5 of T1' are H; and T2' represents a second terminal group which is

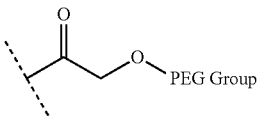

wherein the PEG group is a methoxy-terminated PEG having an average molecular weight in the range of from about 1750 to 2500 Daltons, or T2' represents H, and wherein less than 5 of T2' are H.

In some embodiments, the in vitro half-life for cabazitaxel release from the dendrimer in PBS at pH 7.4 and at 37° C. is in the range of from 20 to 100 hours.

In some embodiments, the in vitro half-life for cabazitaxel release from the dendrimer in PBS at pH 7.4 and at 37° C. is in the range of from 30 to 60 hours.

In a second aspect, there is provided a composition comprising a plurality of dendrimers or pharmaceutically acceptable salts thereof,
  wherein the dendrimers are as defined herein,
  the mean number of first terminal groups per dendrimer in the composition is in the range of from 24 to 32, and
  the mean number of second terminal groups per dendrimer in the composition is in the range of from 24 to 32.

In some embodiments, the cabazitaxel residues comprise a w/w % of the dendrimers in the composition in the range of from 23% w/w to 28% w/w.

In some embodiments, the composition is a pharmaceutical composition, and wherein the composition comprises a pharmaceutically acceptable excipient.

In a third aspect, there is provided a pharmaceutical composition comprising: i) a dendrimer as defined herein, or a pharmaceutically acceptable salt thereof, and ii) a pharmaceutically acceptable excipient.

In some embodiments, the composition is a solid composition comprising a dendrimer as defined herein, a sugar and an acid, and wherein the composition is for reconstitution with a diluent.

In some embodiments, the sugar is trehalose and the acid is citric acid.

In some embodiments, following reconstitution with a diluent, the reconstituted composition has a pH in the range of from 3.5 to 5.5.

In some embodiments, the composition comprises a dendrimer as defined herein, comprises a sugar and an acid, and a diluent.

In some embodiments, the composition is free or substantially free of polyethoxylated castor oil and polyethoxylated sorbitan monooleate.

In some embodiments, the composition is formulated for administration as an infusion over a time period of up to 30 minutes, or wherein the composition is formulated for administration as a bolus over a time period of up to 5 minutes.

In a fourth aspect, there is provided a dendrimer or a pharmaceutical composition as defined herein, for use in therapy.

In some embodiments, the dendrimer or pharmaceutical composition is for use in the treatment of cancer.

There is also provided a method of treating cancer comprising administering to a subject in need thereof a therapeutically effective amount of a dendrimer or pharmaceutical composition as defined herein.

There is also provided use of a dendrimer or of a composition as defined herein, in the manufacture of a medicament for the treatment of cancer.

In some embodiments, the cancer is selected from the group consisting of pancreatic cancer, prostate cancer, breast cancer and ovarian cancer.

In some embodiments, the cancer is metastatic castration-resistant prostate cancer (mCRPC).

In some embodiments, the therapeutically effective amount of the dendrimer is in the range of from 10 to 100 mg/m² body surface area.

In some embodiments, the therapeutically effective amount of the dendrimer is in the range of from 20 to 50 mg/m² body surface area.

In some embodiments, the therapeutically effective amount of the dendrimer is in the range of from 50 to 100 mg/m² body surface area.

In some embodiments, the composition is administered as an infusion over a time period of up to 30 minutes, or wherein the composition is administered as a bolus over a time period of up to 5 minutes.

In some embodiments, the dendrimer is administered in combination with a further therapeutic agent.

In some embodiments, the dendrimer is administered in combination with a further anti-cancer drug.

In some embodiments, the dendrimer is
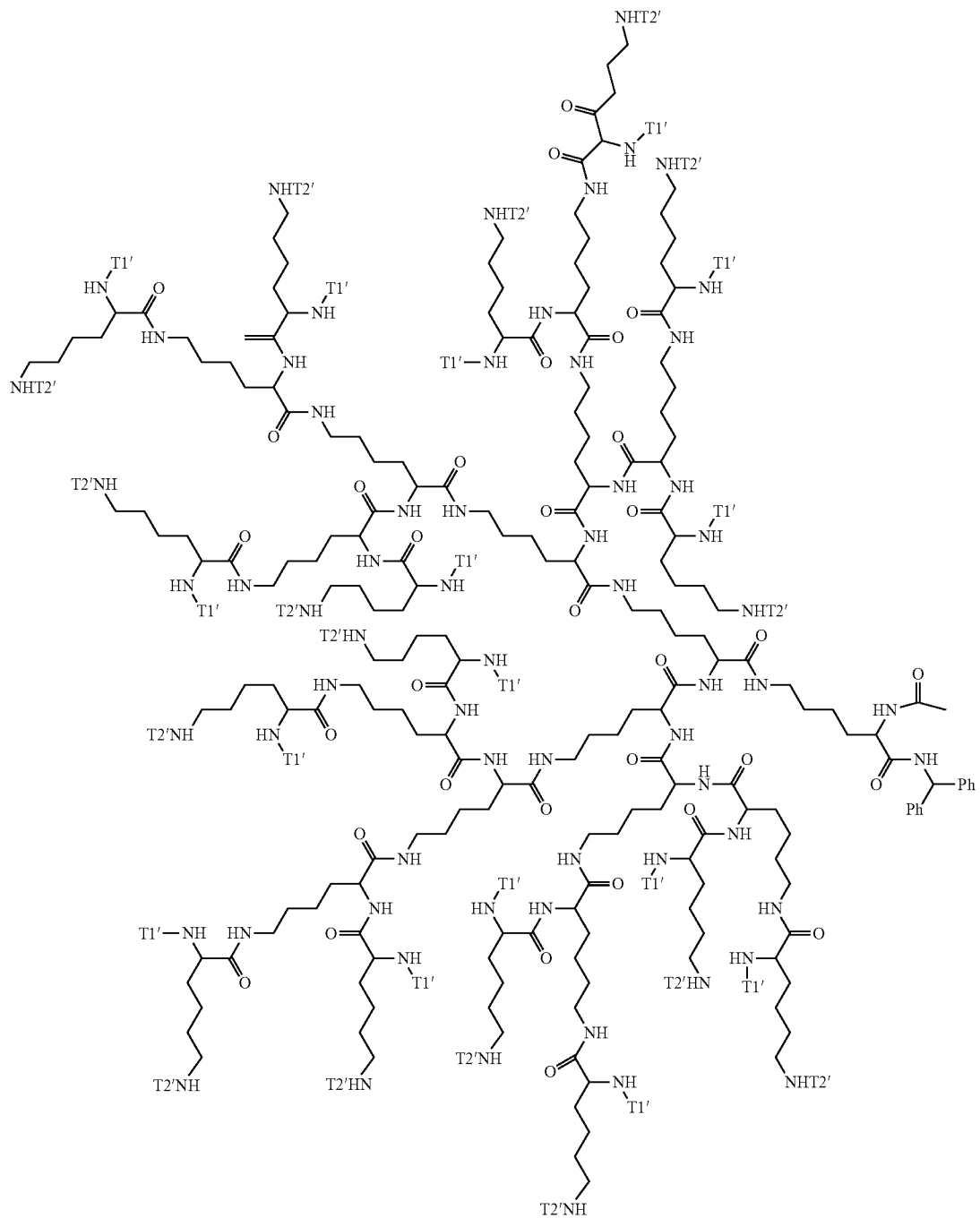

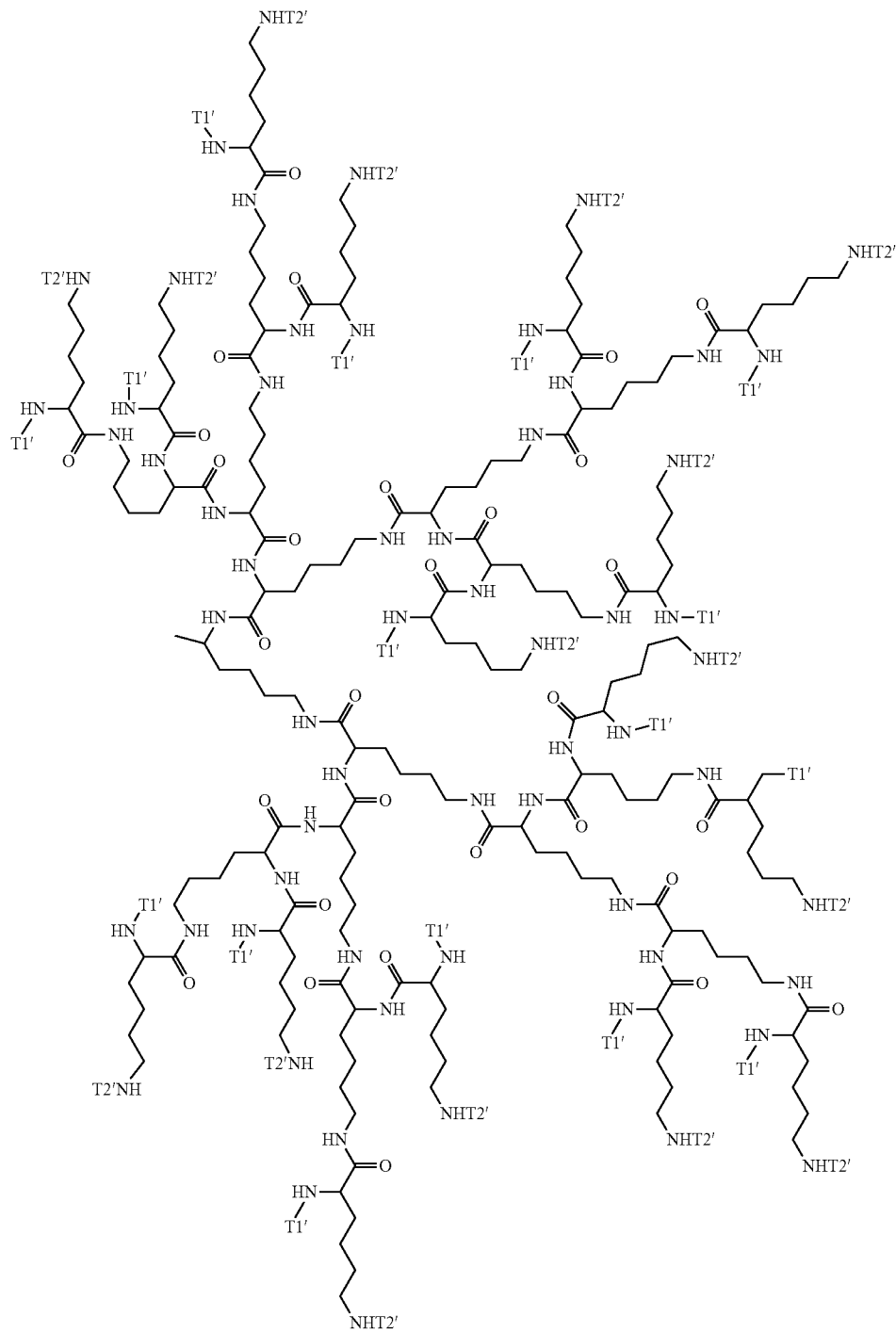

in which T1' represents a first terminal group which is

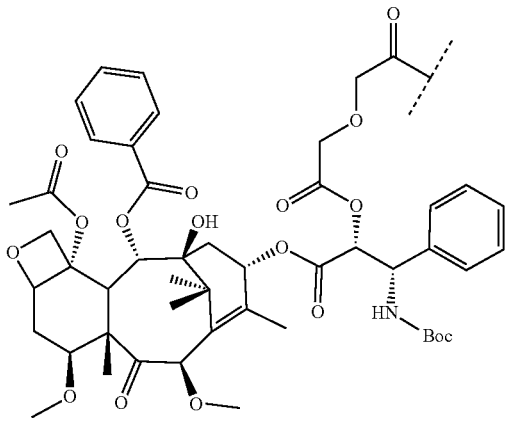

or T1' represents H, wherein less than 5 of T1' are H; and T2' represents a second terminal group which is

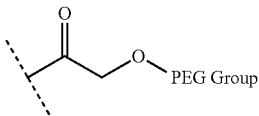

wherein the PEG group is a methoxy-terminated PEG having an average molecular weight in the range of from about 1750 to 2500 Daltons, or T2' represents H, and wherein less than 5 of T2' are H.

In some embodiments, administration of the dendrimer provides a therapeutically effective plasma concentration of cabazitaxel for a longer period of time, in comparison to administration of an equivalent dose of free cabazitaxel.

In some embodiments, administration of the dendrimer provides a maximal concentration ($C_{max}$) of cabazitaxel which is no more than 20% of the maximal concentration provided by administration of an equivalent dose of free cabazitaxel.

In some embodiments, administration of the dendrimer provides enhanced clinical efficacy in comparison to administration of an equivalent dose of free cabazitaxel.

In some embodiments, administration of the dendrimer provides reduced neutropenia, lymphopenia, anemia, and/or thrombocytopenia in comparison to administration of an equivalent dose of free cabazitaxel.

In some embodiments, administration of the dendrimer provides greater AUC of total cabazitaxel, in comparison to direct administration of an equivalent dose of free cabazitaxel.

In some embodiments, administration of the dendrimer provides enhanced clinical efficacy in comparison to administration of an equivalent dose of free cabazitaxel.

In some embodiments, administration of a course of the dendrimer provides enhanced clinical efficacy in comparison to three-weekly administration of 20 or 25 mg/m$^2$ cabazitaxel.

In some embodiments, administration of the dendrimer provides reduced neutropenia, lymphopenia, anemia, and/or thrombocytopenia in comparison to administration of an equivalent dose of free cabazitaxel.

In some embodiments, administration of the dendrimer provides reduced neutropenia, lymphopenia, anemia, and/or thrombocytopenia in comparison to three-weekly administration of 20 or 25 mg/m$^2$ cabazitaxel.

In some embodiments, the subject matter of the present application provides a drug conjugated to a dendrimer, wherein the drug exhibits an improved pharmacokinetic profile of at least one of an improved therapeutic exposure, a lower maximal concentration (C max), and/or an increased area under the curve (AUC), in comparison to the unconjugated dug.

In a fifth aspect, there is provided a process for producing a dendrimer as defined herein, comprising:

a) reacting a cabazitaxel intermediate which is:

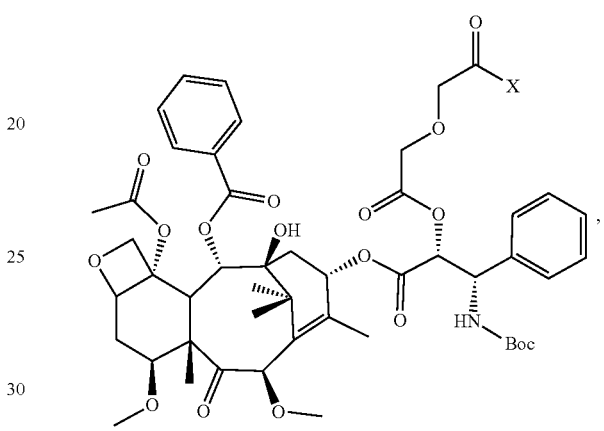

wherein X is —OH or a leaving group, or wherein X together with the C(O) group to which it is attached forms a carboxylate salt;

with a dendrimeric intermediate which comprises:

i) a core unit (C); and ii) building units (BU), each building unit being a lysine residue or an analogue thereof;

wherein the core unit is covalently attached to two building units via amide linkages, each amide linkage being formed between a nitrogen atom present in the core unit and the carbon atom of an acyl group present in a building unit;

the dendrimer being a five generation building unit dendrimer;

wherein building units of different generations are covalently attached to one another via amide linkages formed between a nitrogen atom present in one building unit and the carbon atom of an acyl group present in another building unit;

the dendrimer further comprising:

a plurality of second terminal groups (T2) each comprising a PEG group;

wherein at least one third of the nitrogen atoms present in the outer building units are each covalently attached to a second terminal group;

and wherein at least one third of the nitrogen atoms present in the outer building units are unsubstituted and available for reaction with the first intermediate;

or a salt thereof;
under amide coupling conditions;
or
b) reacting a PEG intermediate which is:

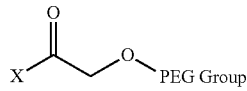

wherein PEG Group is a PEG-containing group, and
X is —OH or a leaving group, or wherein X together with the C(O) group to which it is attached forms a carboxylate salt;
with a dendrimeric intermediate which comprises:
i) a core unit (C); and
ii) building units (BU), each building unit being a lysine residue or an analogue thereof;
wherein the core unit is covalently attached to two building units via amide linkages, each amide linkage being formed between a nitrogen atom present in the core unit and the carbon atom of an acyl group present in a building unit;
the dendrimer being a five generation building unit dendrimer;
wherein building units of different generations are covalently attached to one another via amide linkages formed between a nitrogen atom present in one building unit and the carbon atom of an acyl group present in another building unit;
the dendrimer further comprising:
a plurality of first terminal groups (T1) each comprising a cabazitazel residue covalently attached to a diglycolyl linker group;
wherein at least one third of the nitrogen atoms present in the outer building units are each covalently attached to a first terminal group;
and wherein at least one third of the nitrogen atoms present in the outer building units are unsubstituted;
or a salt thereof;
under amide coupling conditions;
or
c) reacting a surface unit intermediate which is:

wherein PEG Group is a PEG-containing group, and
X is —OH or a leaving group, or wherein X together with the C(O) group to which it is attached forms a carboxylate salt;
with a dendrimeric intermediate comprising:
i) a core unit (C); and
ii) building units (BU), each building unit being a lysine residue or an analogue thereof;
wherein the core unit is covalently attached to two building units via amide linkages, each amide linkage being formed between a nitrogen atom present in the core unit and the carbon atom of an acyl group present in a building unit;
the dendrimeric intermediate being a four generation building unit dendrimeric intermediate;
wherein building units of different generations are covalently attached to one another via amide linkages formed between a nitrogen atom present in one building unit and the carbon atom of an acyl group present in another building unit;
and wherein nitrogen atoms present in the outer building units of the dendrimeric intermediate are unsubstituted;
or a salt thereof;
under amide coupling conditions.

In a sixth aspect, there is provided an intermediate for producing a dendrimer which is

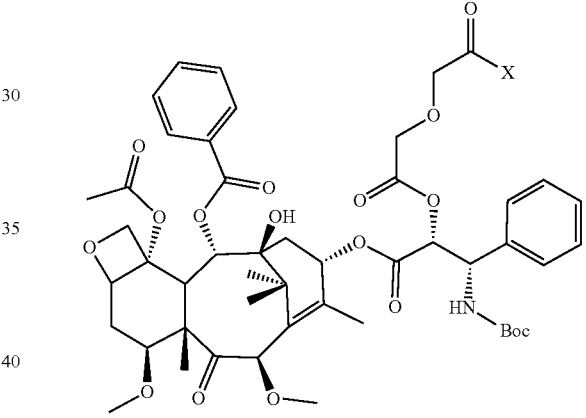

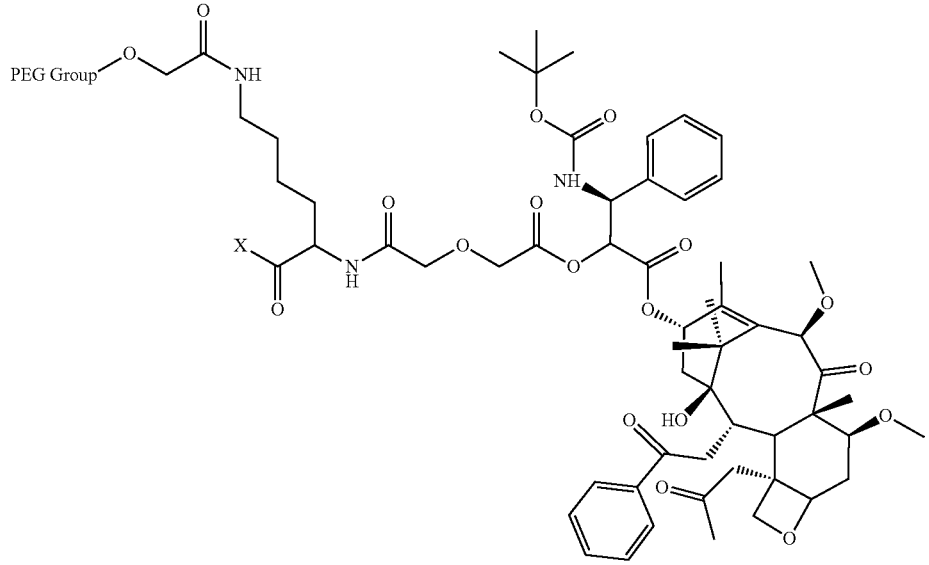

wherein X is —OH or a leaving group, or wherein X together with the C(O) group to which it is attached forms a carboxylate salt.

In a seventh aspect, there is provided an intermediate for producing a dendrimer which is

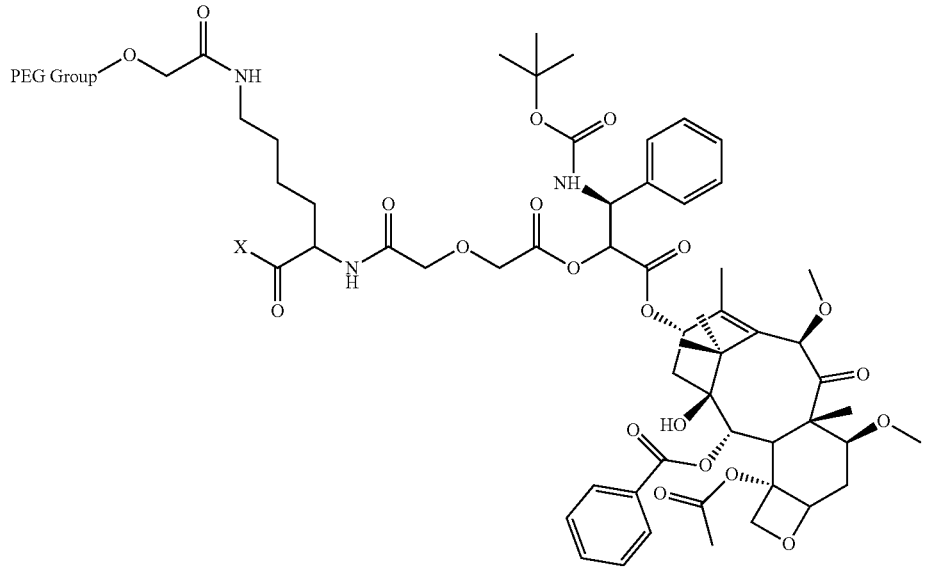

wherein PEG Group is a PEG-containing group, and X is —OH or a leaving group, or wherein X together with the C(O) group to which it is attached forms a carboxylate salt.

It will be appreciated that further aspects, embodiments, and examples, are described herein, which may include one or more of the embodiments or features as described above.

DETAILED DESCRIPTION OF THE INVENTION

General Definitions

Figure 1:
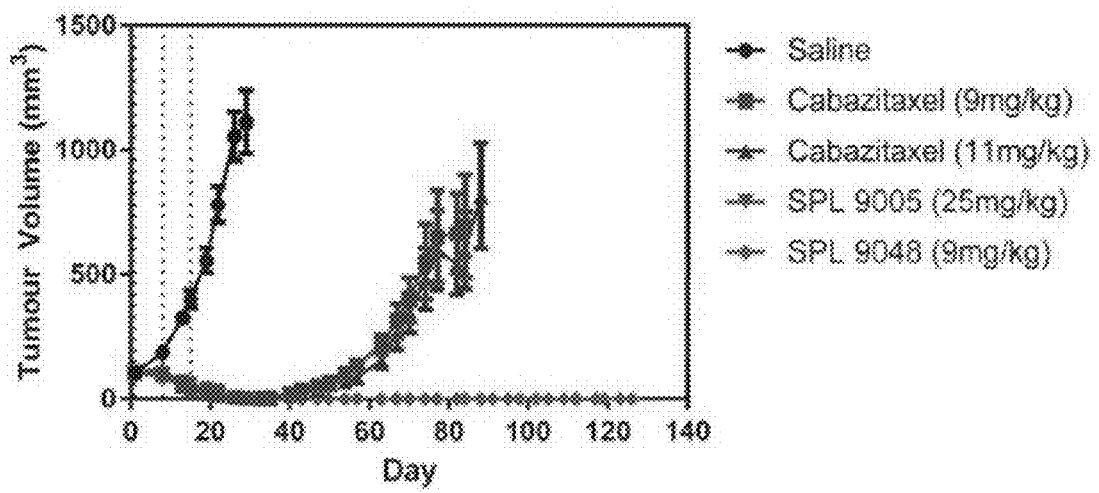
FIG. 1 shows the efficacy of a compound of the present disclosure (SPL9048) and comparator compounds (cabazitaxel, and SPL9005—a comparator cabazitaxel-dendrimer compound) in SCID mice represented by change in mean tumour volume (TV) (mm$^3$) over time in a prostate cancer model study.

Unless specifically defined otherwise, all technical and scientific terms used herein shall be taken to have the same meaning as commonly understood by one of ordinary skill in the art (e.g., chemistry, biochemistry, medicinal chemistry, polymer chemistry, and the like).

As used herein, the term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−20%, more preferably +/−10%, of the designated value.

As used herein, singular forms "a", "an" and "the" include plural aspects, unless the context clearly indicates otherwise.

Throughout this specification, the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein, the term "subject" refers to any organism susceptible to a disease or condition. In one embodiment, the disease or condition is cancer. For example, the subject can be a mammal, primate, livestock (e.g., sheep, cow, horse, pig), companion animal (e.g., dog, cat), or laboratory animal (e.g., mouse, rabbit, rat, guinea pig, hamster). In one example, the subject is a mammal. In one embodiment, the subject is human.

As used herein, the term "treating" includes alleviation of the symptoms associated with a specific disorder or condition and eliminating said symptoms. For example, as used herein, the term "treating cancer" refers to alleviating the symptoms associated with cancer and eliminating said symptoms. In one embodiment, the term "treating cancer" refers to a reduction in cancerous tumour size. In one embodiment, the term "treating cancer" refers to an increase in progression-free survival. As used herein, the term "progression-free survival" refers to the length of time during and after the treatment of cancer that a patient lives with the disease, i.e., cancer, but does not have a recurrence or increase in symptoms of the disease.

As used herein, the term "prevention" includes prophylaxis of the specific disorder or condition. For example, as used herein, the term "preventing cancer" refers to preventing the onset or duration of the symptoms associated with cancer. In one example, the term "preventing cancer" refers to slowing or halting the progression of the cancer. In one example, the term "preventing cancer" refers to slowing or preventing metastasis.

As would be understood by the person skilled in the art, a dendrimer would be administered in a therapeutically effective amount. The term "therapeutically effective amount", as used herein, refers to a dendrimer being administered in an amount sufficient to alleviate or prevent to some extent one or more of the symptoms of the disorder or condition being treated. The result can be the reduction and/or alleviation of the signs, symptoms, or causes of a disease or condition, or any other desired alteration of a biological system. In one embodiment, the term "therapeutically effective amount" refers to a dendrimer being administered in an amount sufficient to result in a reduction in cancerous tumour size. In one embodiment, the term "therapeutically effective amount" refers to a dendrimer being administered in an amount sufficient to result in an increase in progression-free survival. The term, an "effective amount", as used herein, refers to an amount of a dendrimer effective to achieve a desired pharmacologic effect or therapeutic improvement without undue adverse side effects or to achieve a desired pharmacologic effect or therapeutic improvement with a reduced side effect profile. By way of example only, therapeutically effective amounts may be determined by routine experimentation, including but not limited to a dose escalation clinical trial. The term "therapeutically effective amount" includes, for example, a prophylactically effective amount. In one embodiment, a prophylactically effective amount is an amount sufficient to prevent metastasis. It is understood that "an effective amount" or "a therapeutically effective amount" can vary from subject to subject, due to variation in metabolism of the compound and any of age, weight, general condition of the subject, the condition being treated, the severity of the condition being treated, and the judgment of the prescribing physician. Thus, it is not always possible to specify an exact "effective amount". However, an appropriate "effective amount" in any individual case may be determined by one of ordinary skill in the art using routine experimentation. Where more than one therapeutic agent is used in combination, a "therapeutically effective amount" of each therapeutic agent can refer to an amount of the therapeutic agent that would be therapeutically effective when used on its own, or may refer to a reduced amount that is therapeutically effective by virtue of its combination with one or more additional therapeutic agents.

As used herein, the term "alkyl" refers to straight (i.e., linear) or branched chain hydrocarbons ranging in size from one to 10 carbon atoms (i.e. $C_{1-10}$alkyl). Thus, alkyl moieties include, unless explicitly limited to smaller groups, moieties ranging in size, for example, from about one to about six carbon atoms or greater, such as, methyl, ethyl, n-propyl, iso-propyl and/or butyl, pentyl, hexyl, and higher isomers. In one example, the alkyl moiety is of one to 10 carbon atoms (i.e. $C_{1-10}$alkyl). In another example, the alkyl moiety is of 2 to 4 carbon atoms, preferably 4 carbon atoms.

As used herein, the term "alkylene" refers to straight (i.e. linear) or branched chain hydrocarbons ranging in size from 1 to 10 carbon atoms (i.e. $C_{1-10}$alkylene). Thus, alkylene moieties include, for example, —$CH_2$—, —$CH_2CH_2$—, —$CH_2CH_2CH_2$—, —$CH_2CH(CH_3)$—, —$CH_2CH_2CH_2CH_2$—, —$CH_2CH(CH_3)CH_2$—, and the like.

Suitable salts of the dendrimers include those formed with organic or inorganic acids or bases. As used herein, the phrase "pharmaceutically acceptable salt" refers to pharmaceutically acceptable organic or inorganic salts. Exemplary acid addition salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Exemplary base addition salts include, but are not limited to, ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion. It will also be appreciated that non-pharmaceutically acceptable salts also fall within the scope of the present disclosure since these may be useful as intermediates in the preparation of pharmaceutically acceptable salts or may be useful during storage or transport.

Those skilled in the art of organic and/or medicinal chemistry will appreciate that many organic compounds can form complexes with solvents in which they are reacted or from which they are precipitated or crystallized. These complexes are known as "solvates". For example, a complex with water is known as a "hydrate". As used herein, the phrase "pharmaceutically acceptable solvate" or "solvate" refer to an association of one or more solvent molecules and a compound of the present disclosure. Examples of solvents that form pharmaceutically acceptable solvates include, but are not limited to, water, isopropanol, ethanol, methanol, DMSO, ethyl acetate, acetic acid, and ethanolamine.

As used herein, the term "dendrimer" refers to a molecule containing a core and dendrons attached to the core. Each dendron is made up of generations of branched building units resulting in a branched structure with increasing number of branches with each generation of building units. A "dendrimer", including a drug-dendrimer conjugate, may include pharmaceutically acceptable salts or solvates as defined supra.

As used herein, the term "building unit" refers to a branched molecule which is a lysine residue or an analogue thereof having three functional groups, one for attachment to the core or a previous generation of building units and at least two functional groups for attachment to the next generation of building units or forming the surface of the dendrimer molecule.

As used herein, the term "attached" refers to a connection between chemical components by way of covalent bonding. The term "covalent bonding", as used herein, refers to a chemical bond formed by the sharing of one or more electrons, especially pairs of electrons, between atoms. The term "covalent bonding" is used interchangeable with the term "covalent attachment".

As used herein, the term "solubilisation excipient" refers to a formulation additive that is used to solubilise insoluble or sparingly soluble drugs into an aqueous formulation. Examples include surfactants such as polyethoxylated caster oils including Cremophor EL, Cremophor RH 40 and Cremophor RH 60, D-α-tocopherol-polyethylene-glycol 1000 succinate, polysorbate 20, polysorbate 80, solutol HS 15, sorbitan monoleate, poloxamer 407, Labrasol and the like.

JEVTANA® brand cabazitaxel is manufactured by Sanofi (France), and is an example of free cabazitaxel for comparing to dendrimer. JEVTANA® brand cabazitaxel pharmacokinetic data has been published (see e.g. Mita A C, Denis L J, Rowinsky E K, et al. Phase I and pharmacokinetic study of XRP6258 (RPR 116258A), a novel taxane, administered as a 1-hour infusion every 3 weeks in patients with advanced solid tumors. Clin Cancer Res. 2009; 15(2):723-730).

In Mita, the 25-mg/m$^2$ dose was correlated with a $C_{max}$ of 535±305 mcg/L and an AUC concentration of 642±320 mcg/L per hour. A triphasic model was used to describe the drug's decreased plasma concentrations. The plasma concentration pharmacokinetic activity was characterized by a rapid initial elimination phase (average terminal half-life [t½]=2.6±1.4 minutes), followed by an intermediate elimination phase (average t½=1.3±0.6 hours) and a prolonged terminal elimination phase (average t½=77.3±45.5 hours). Approximately 80% of the dose was eliminated within 2 weeks. The volume of distribution at steady state was large and highly variable (2,034±1,495 L/m2).

The principal dose-limiting toxicity in this study was hematological bone-marrow suppression (i.e., neutropenia). One patient (4%) experienced prolonged grade 4 neutropenia, and a second patient (4%) experienced febrile neutropenia, both with the 25-mg/m2 dose. Nonhematological toxicities also occurred. Two patients (8%) experienced flushing, dizziness, and chest tightness, which were identified as grade 1 hypersensitivity reactions. Other nonhematological toxicities included diarrhea (14 patients; 56%), nausea (10 patients; 40%), fatigue (nine patients; 36%), neurotoxicity (nine patients; 36%), and vomiting (four patients; 16%).

In the Phase 3 TROPIC study in patients with metastatic prostate cancer (n=67), the mean $C_{max}$ was 226 ng/mL (coefficient of variation, CV 107%) and was reached at the end of the 1-hour infusion ($T_{max}$). The mean AUC was 991 ng·h/mL (CV:34%). Neutropenia (all grades) occurred in 94% of the cabazitaxel patients and Grade 3 or 4 febrile neutropenia occurred in 8% of the cabazitaxel patients. In the TROPIC registration study for JEVTANA® brand cabazitaxel, after a 1-hour IV administration dose of cabazitaxel at 25 mg/m2, (de Bono J S, Oudard S, Ozguroglu M, et al. Prednisone plus cabazitaxel or mitoxantrone for metastatic castration-resistant prostate cancer progressing after docetaxel treatment: A randomised open-label trial. Lancet. 2010; 376(9747):1147-1154.)

Dendrimer

In a first aspect. there is provided a dendrimer comprising:
i) a core unit (C); and
ii) building units (BU), each building unit being a lysine residue or an analogue thereof;
wherein the core unit is covalently attached to two building units via amide linkages, each amide linkage being formed between a nitrogen atom present in the core unit and the carbon atom of an acyl group present in a building unit;
the dendrimer being a five generation building unit dendrimer;
wherein building units of different generations are covalently attached to one another via amide linkages formed between a nitrogen atom present in one building unit and the carbon atom of an acyl group present in another building unit;
the dendrimer further comprising:
iii) a plurality of first terminal groups (T1) each comprising a cabazitazel residue covalently attached to a diglycolyl linker group; and
iv) a plurality of second terminal groups (T2) each comprising a PEG group;
wherein at least one third of the nitrogen atoms present in outer building units are each covalently attached to a first terminal group; and
at least one third of the nitrogen atoms present in outer building units are each covalently attached to a second terminal group;
or a pharmaceutically acceptable salt thereof.

The core unit (C) of the dendrimer is covalently attached to two building units via amide linkages, each amide linkage being formed between a nitrogen atom present in the core unit and the carbon atom of an acyl group present in a building unit. Accordingly, the core unit may for example be formed from a core unit precursor comprising two amino groups. Any suitable diamino-containing molecule may be used as the core unit precursor. In some embodiments, the core unit is:

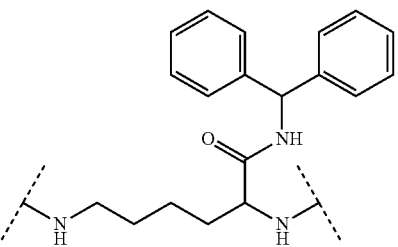

and may, for example, be formed from a core unit precursor:

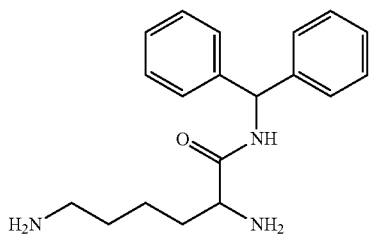 [SMILES: NCCCCC(N)C(=O)NC(c1ccccc1)c1ccccc1]

having two reactive (amino) nitrogens.

The building units (BU) are lysine residues or analogues thereof, and may be formed from suitable building unit precursors, e.g. lysine or lysine analogues containing appropriate protecting groups. Lysine analogues have two amino nitrogen atoms for bonding to a subsequent generation of building units and an acyl group for bonding to a previous generation of building units or a core. Examples of suitable building units include

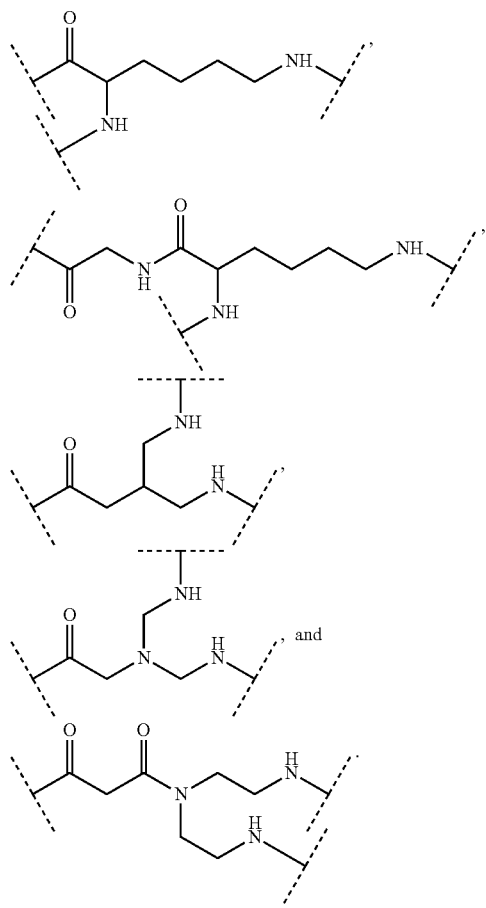

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group.

In some preferred embodiments, the building units are each:

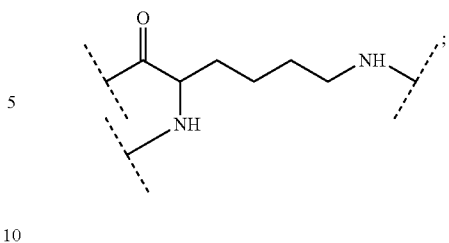

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group.

In some preferred embodiments, the building units are each:

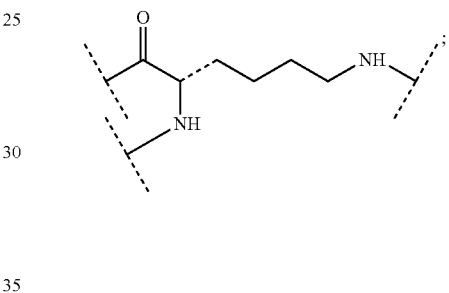

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group.

The outermost generation of building units ($BU_{outer}$) may be formed by lysine or lysine analogue building units as used in the other generations of building units (BU) as described above. The outermost generation of building units ($BU_{outer}$) is the generation of building units that is outermost from the core of the dendrimer, i.e., no further generations of building units are attached to the outermost generation of building units ($BU_{outer}$).

It will be appreciated that the dendrons of the dendrimer may for example be synthesised to the required number of generations through the attachment of building units (BU) accordingly. In some embodiments each generation of building units (BU) may be formed of the same building unit, for example all of the generations of building units may be lysine building units. In some other embodiments, one or more generations of building units may be formed of different building units to other generations of building units.

The dendrimer is a five generation building unit dendrimer. A five generation building unit dendrimer is a dendrimer having a structure which includes five building units which are covalently linked to another, for example in the case where the building units are lysines, it may comprise the substructure:

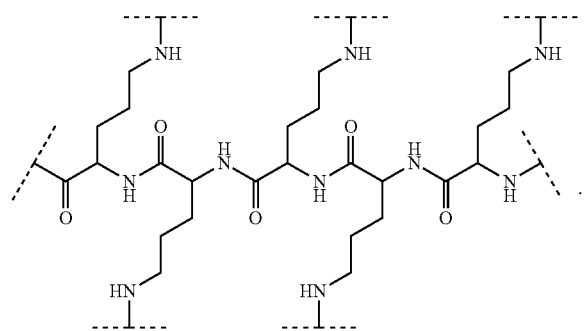

In some embodiments, the dendrimer has five complete generations of building units. With a core having two reactive amine groups, such a dendrimer will comprise 62 building units (i.e. core unit+2 BU+4 BU+8 BU+16 BU+32 BU). However, it will be appreciated that, due to the nature of the synthetic process for producing the dendrimers, one or more reactions carried out to produce the dendrimers may not go fully to completion. Accordingly, in some embodiments, the dendrimer may comprise an incomplete generations of building units. For example, a population of dendrimers may be obtained, in which the dendrimers have a distribution of numbers of building units per dendrimer. In some embodiments, a population of dendrimers is obtained which has a mean number of building units per dendrimer of at least 55, or at least 56, or at least 57, or at least 58, or at least 59, or at least 60. In some embodiments, a population of dendrimers is obtained in which at least 60%, at least 70%, at least 80%, at least 90% or at least 95% of the dendrimers have 55 or more building units. In some embodiments, a population of dendrimers is obtained in which at least 60%, at least 70%, at least 80%, at least 90% or at least 95% of the dendrimers have 60 or more building units.

Each reactive (amino) group of the core represents a conjugation site for a dendron comprising one or more generations of building units. The core has two reactive (amino) groups, and two dendrons, for the generations of building units to be attached.

In some embodiments, each generation of building units in each dendron (X) may be represented by the formula $[BU]_2(b-1)$, wherein b is the generation number. A dendron (X) having five complete generations of building units is represented as $[BU]_1$-$[BU]_2$-$[BU]_4$-$[BU]_8$-$[BU]_{16}$.

The dendrimer comprises a plurality of first terminal groups (T1) each comprising a cabazitaxel residue covalently attached to a diglycolyl linker group. Each first terminal group (T1) is preferably:

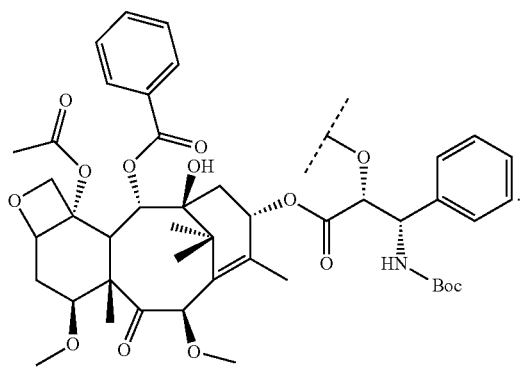

i.e. a cabazitaxel residue covalently attached to a diglycolyl linker via an ester linkage formed between an oxygen atom present as part of the cabazitaxel side-chain and a carbon atom of an acyl group present as part of the diglycolyl linker. The other acyl group of the diglycolyl linker forms an amide linkage with a nitrogen atom present in an outer building unit. In such embodiments, the cabazitaxel residue is:

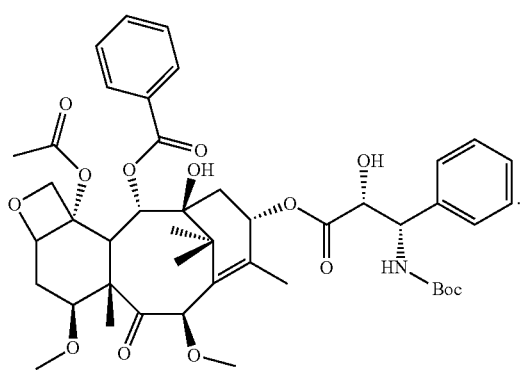

Upon in vivo administration, typically the dendrimer releases cabazitaxel, i.e.:

The dendrimer comprises a plurality of second terminal groups (T2) each comprising a PEG group. The second terminal group T2 is a pharmacokinetic modifying agent. A pharmacokinetic modifying agent is an agent that can modify or modulate the pharmacokinetic profile of the dendrimer or the pharmaceutically active agent (i.e. cabazitaxel) that the dendrimer is delivering. The pharmacokinetic modifying agent may modulate the absorption, distribution, metabolism, excretion and/or toxicity of the dendrimer of the pharmaceutically active agent. The pharmacokinetic modifying agent (T2) may influence the rate of release of the pharmaceutically active agent, either by slowing or increasing the rate in which the active agent is released from the dendrimer by either chemical (e.g., hydrolysis) or enzymatic degradation pathways. The pharmacokinetic modifying agent (T2) may change the solubility profile of the dendrimer, either increasing or decreasing the solubility of the dendrimer in a pharmaceutically acceptable carrier. The pharmacokinetic modifying agent (T2) may assist the dendrimer in delivering the pharmaceutically active agent to specific tissues (e.g., tumours). The pharmacokinetic modifying agent (T2) may extend the pharmaceutically active agent half-life by reducing clearance of the dendrimer.

A PEG group is a polyethylene glycol group, i.e. a group comprising repeat units of the formula —$CH_2CH_2O$—. PEG materials used to produce the dendrimer of the present disclosure typically contain a mixture of PEGs having some variance in molecular weight (i.e., ±10%), and therefore the molecular weight specified is typically an approximation of the average molecular weight of the PEG composition. For example, the term "$PEG_{-2100}$" refers to polyethylene glycol having an average molecular weight of approximately 2100 Daltons, i.e. ±approximately 10% (i.e., $PEG_{1900}$ to $PEG_{2300}$). Three methods are commonly used to calculate MW averages: number average, weight average, and z-average molecular weights. As used herein, the phrase "molecular weight" is intended to refer to the weight-average molecular weight which can be measured using techniques well-known in the art including, but not limited to, NMR, mass spectrometry, matrix-assisted laser desorption ionization time of flight (MALDI-TOF), gel permeation chromatography or other liquid chromatography techniques, light scattering techniques, ultracentrifugation and viscometry.

In some embodiments, the second terminal groups comprise PEG groups having an average molecular weight of between about 200 and 5000 Daltons. In some embodiments, the second terminal groups comprise PEG groups having an average molecular weight of at least 750 Daltons. In some embodiments, the second terminal groups comprise PEG groups having an average molecular weight in the range of from 1000 to 2500 Daltons. In some embodiments, the second terminal groups comprise PEG groups having an average molecular weight in the range of from 1900 to 2300 Daltons. In some embodiments, the second terminal groups comprise PEG groups having an average molecular weight in the range of from 2000 to 2200 Daltons. In some embodiments, the second terminal groups comprise PEG groups having an average molecular weight of about 2100 Daltons.

In some embodiments, the PEG group has a polydispersity index (PDI) of between about 1.00 and about 1.50, between about 1.00 and about 1.25, or between about 1.00 and about 1.10. In some embodiments, the PEG group has a polydispersity index (PDI) of about 1.05. The term "polydispersity index" refers to a measure of the distribution of molecular mass in a given polymer sample. The polydispersity index (PDI) is equal to the weight average molecular weight ($M_w$) divided by the number average molecular weight ($M_n$) and indicates the distribution of individual molecular masses in a batch of polymers. The polydispersity index (PDI) has a value equal to or greater than one, but as the polymer approaches uniform change length and average molecular weight, the polydispersity index (PDI) will be closer to one.

In some embodiments, the PEG group is a methoxy-terminated PEG.

The PEG group may be attached to the outer building unit via any suitable means. In some embodiments, a PEG linking group is used to attach the PEG group to the outer building unit. In some embodiments, the second terminal groups each comprise a PEG group covalently attached to a PEG linking group (L1) via an ether linkage formed between a carbon atom present in the PEG group and an oxygen atom present in the PEG linking group, and each second terminal group is covalently attached to a building unit via an amide linkage formed between a nitrogen atom present in a building unit and the carbon atom of an acyl group present in the PEG linking group. In some embodiments, the second terminal groups are each

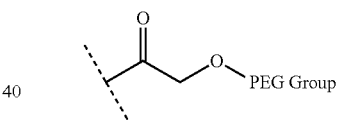

and wherein the PEG group is a methoxy-terminated PEG having an average molecular weight in the range of from about 1750 to 2500 Daltons.

In the dendrimers of the present disclosure, at least one third of the nitrogen atoms present in outer building units are each covalently attached to a first terminal group; and at least one third of the nitrogen atoms present in outer building units are each covalently attached to a second terminal group.

In some embodiments, the dendrimers have controlled stoichiometry and/or topology. For example, the dendrimers are typically produced using synthetic processes that allow for a high degree of control over the number and arrangement of first and second terminal groups present on the dendrimers. In some embodiments, each functionalised outer building unit contains one first terminal group and one second terminal group. In some embodiments, the dendrimer comprises surface units comprising an outer building unit attached to a first terminal group and a second terminal group, the surface units having the structure:

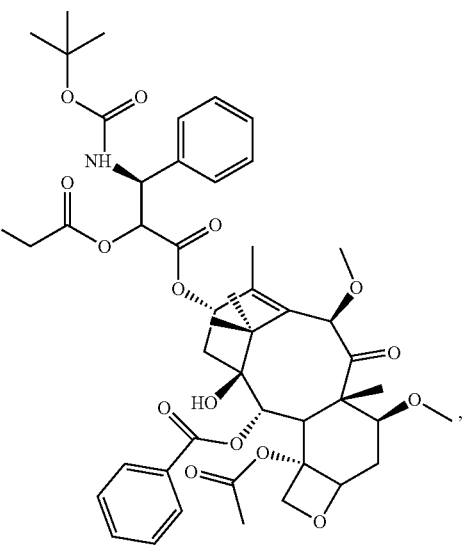

and wherein the PEG group is a methoxy-terminated PEG having an average molecular weight in the range of from about 1750 to 2500 Daltons. In some embodiments, the dendrimer has from 28 to 32 surface units. In some embodiments, the dendrimer has from 30 to 32 surface units.

In some embodiments, at least 40% of the nitrogen atoms present in the outer building units are each covalently attached to a first terminal group. In some embodiments, at least 45% of the nitrogen atoms present in the outer building units are each covalently attached to a first terminal group. In some embodiments, about 50% of the nitrogen atoms present in the outer building units are each covalently attached to a first terminal group.

In some embodiments, at least 40% of the nitrogen atoms present in the outer building units are each covalently attached to a second terminal group. In some embodiments, at least 45% of the nitrogen atoms present in the outer building units are each covalently attached to a second terminal group. In some embodiments, about 50% of the nitrogen atoms present in the outer building units are each covalently attached to a second terminal group.

In some embodiments, at least 40% of the nitrogen atoms present in the outer building units are each covalently attached to a first terminal group; and at least 40% of the nitrogen atoms present in the outer building units are each covalently attached to a second terminal group. In some embodiments, at least 45% of the nitrogen atoms present in the outer building units are each covalently attached to a first terminal group; and at least 45% of the nitrogen atoms present in the outer building units are each covalently attached to a second terminal group. In some embodiments, about 50% of the nitrogen atoms present in the outer building units are each covalently attached to a first terminal group; and about 50% of the nitrogen atoms present in the outer building units are each covalently attached to a second terminal group.

In some embodiments, the five generations of building units are complete generations, and wherein the outer generation of building units provides 64 nitrogen atoms for covalent attachment to a first terminal group or a second terminal, wherein from 26 to 32 first terminal groups are covalently attached to one of said nitrogen atoms, and wherein from 28 to 32 second terminal groups are each covalently attached to one of said nitrogen atoms. In some embodiments, from 28 to 32 first terminal groups are each covalently attached to one of said nitrogen atoms. In some embodiments, from 29 to 31 first terminal groups are each covalently attached to one of said nitrogen atoms.

In some embodiments, cabazitaxel residues comprise at least 20% w/w of the dendrimer, at least 22% w/w of the dendrimer, or at least 24% w/w of the dendrimer. In some embodiments, cabazitaxel residues comprise up to 30% w/w of the dendrimer, up to 28% w/w of the dendrimer or up to 26% w/w of the dendrimer. In some embodiments, cabazitaxel residues comprise a w/w % of the dendrimer in the range of from 20% w/w to 30% w/w, or from 23% w/w to 28% w/w, or from 24% w/w to 26% w/w. The w/w % of the dendrimer which is cabazitaxel residues may be determined by any suitable means. In some embodiments, the w/w % of the dendrimer which is cabazitaxel residues may be determined by $^1$H NMR.

In some embodiments, no more than one quarter of the nitrogen atoms present in the outer generation of building units are unsubstituted. In some embodiments, no more than one fifth of the nitrogen atoms present in said outer generation of building units are unsubstituted. In some embodiments, no more than one sixth of the nitrogen atoms present in said outer generation of building units are unsubstituted. In some embodiments, no more than one eighth of the nitrogen atoms present in said outer generation of building units are unsubstituted. In some embodiments, no more than one tenth of the nitrogen atoms present in said outer generation of building units are unsubstituted.

In some embodiments, no more than 20 nitrogen atoms present in the outer generation of building units are unsubstituted. In some embodiments, no more than 10 nitrogen atoms present in the outer generation of building units are unsubstituted. In some embodiments, no more than 5 nitrogen atoms present in the outer generation of building units are unsubstituted. In some embodiments, no more than 3 nitrogen atoms present in the outer generation of building units are unsubstituted. In some embodiments, no more than 2 nitrogen atoms present in the outer generation of building units are unsubstituted. In some embodiments, no more than 1 nitrogen atom present in the outer generation of building units are unsubstituted. In some embodiments, substantially all of the nitrogen atoms present in the outer generation of building units are substituted.

In some embodiments, the dendrimer is:
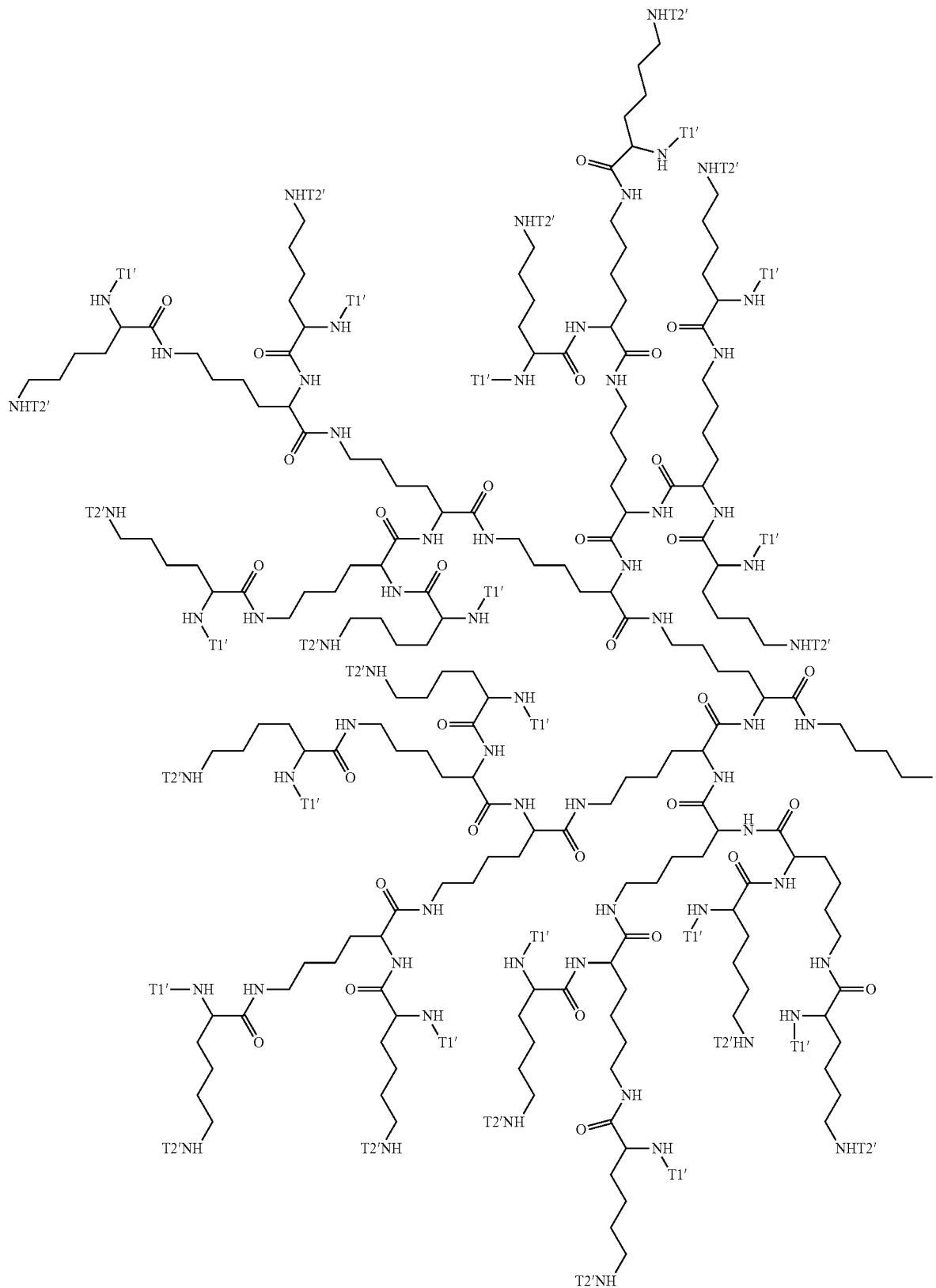

-continued
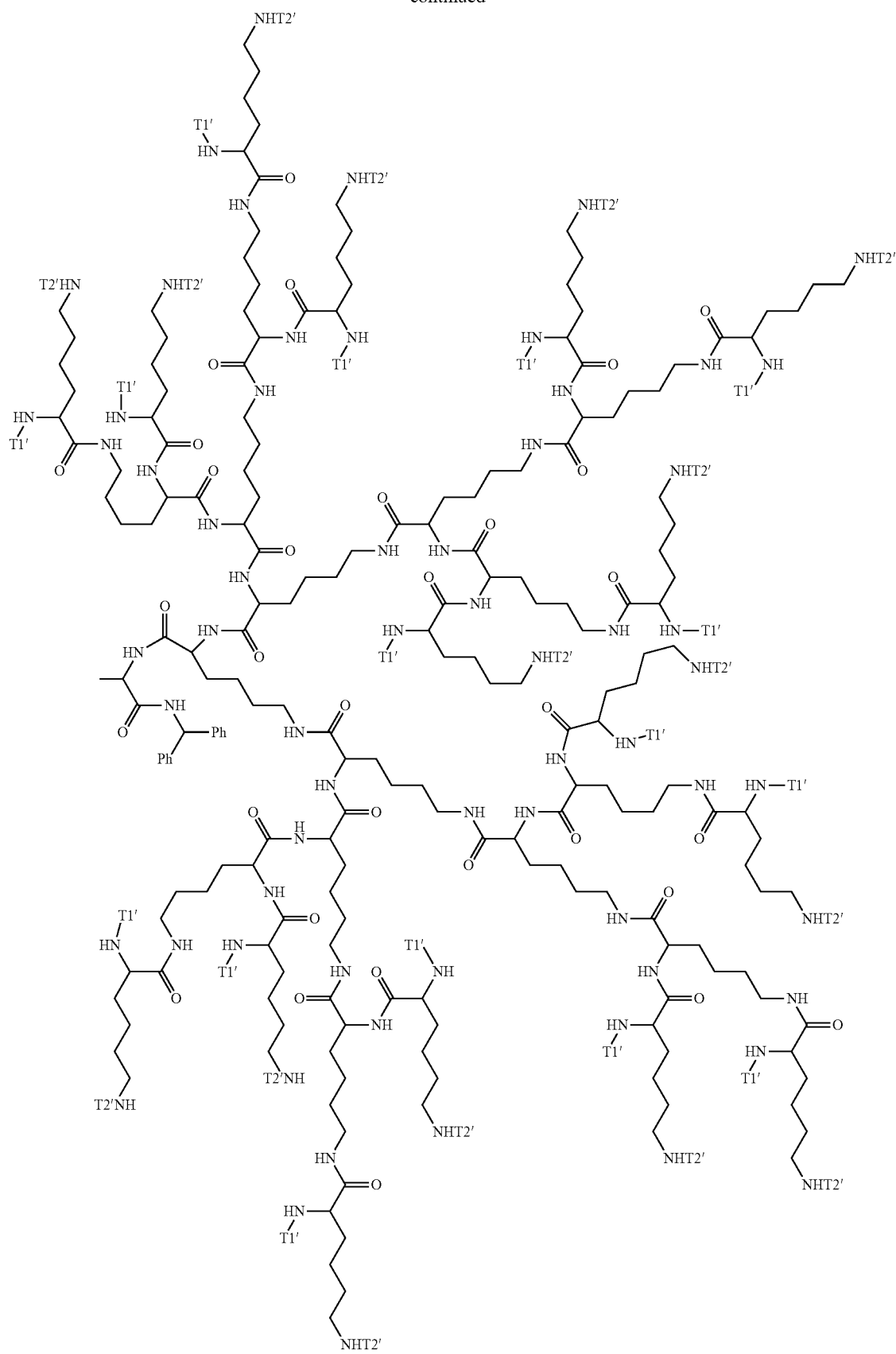

in which T1' represents a first terminal group which is

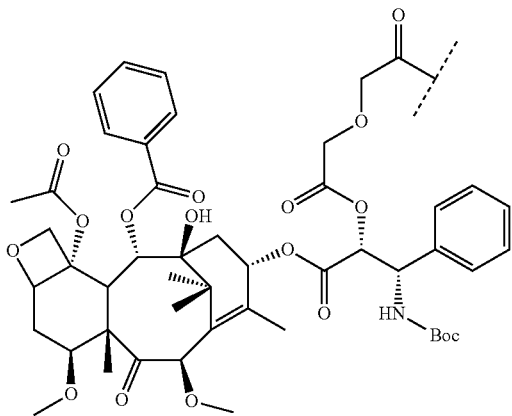

or T1' represents H, wherein less than 5 of T1' are H; and T2' represents a second terminal group which is

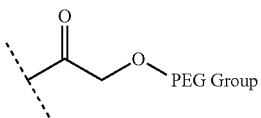

wherein the PEG group is a methoxy-terminated PEG having an average molecular weight in the range of from about 1750 to 2500 Daltons, or T2' represents H, and wherein less than 5 of T2' are H.

In some embodiments, the dendrimer has a molecular weight in the range of from 50 to 300 kDa. In some embodiments, the dendrimer has a molecular weight in the range of from 75 to 200 kDa. In one example, the dendrimer has a molecular weight in the range of from 90 to 150 kDa.

In some embodiments, the in vitro half-life for cabazitaxel release from the dendrimer in PBS (phosphate-buffer saline) at pH 7.4 and at 37° C. is in the range of from 20 to 100 hours. In some embodiments, the in vitro half-life for cabazitaxel release from the dendrimer in PBS at pH 7.4 and at 37° C. is in the range of from 24 to 60 hours. In some embodiments, the in vitro half-life for cabazitaxel release from the dendrimer in PBS at pH 7.4 and at 37° C. is in the range of from 30 to 60 hours. In some embodiments, the in vitro half-life for cabazitaxel release from the dendrimer in PBS at pH 7.4 and at 37° C. is in the range of from 30 to 50 hours.

Compositions

In some embodiments, the dendrimer is presented as a composition, preferably a pharmaceutical composition.

It will be appreciated that there may be some variation in the molecular composition between the dendrimers present in a given composition, as a result of the nature of the synthetic process for producing the dendrimers. For example, as discussed above one or more synthetic steps used to produce a dendrimer may not proceed fully to completion, which may result in the presence of dendrimers which do not all comprise the same number of first terminal groups or second terminal groups, or which contain incomplete generations of building units.

Accordingly, there is provided a composition comprising a plurality of dendrimers or pharmaceutically acceptable salts thereof, wherein the dendrimers are as defined herein, the mean number of first terminal groups per dendrimer in the composition is in the range of from 24 to 32, and the mean number of second terminal groups per dendrimer in the composition is in the range of from 24 to 32. In some embodiments, the mean number of first terminal groups per dendrimer is in the range of from 26 to 32, and wherein the mean number of second terminal groups per dendrimer is in the range of from 28 to 32. In some embodiments, the mean number of first terminal groups per dendrimer is in the range of from 28 to 32, or in the range of from 29 to 31. In some embodiments, the mean number of second terminal groups per dendrimer is in the range of from 29 to 31.

In some embodiments, at least 50%, at least 60%, at least 70%, at least 80%, at least 90%, or at least 95% of the dendrimers contain at least 24 first terminal groups. In some embodiments, at least 50%, at least 60%, at least 70%, at least 80%, at least 90%, or at least 95% of the dendrimers contain at least 26 first terminal groups. In some embodiments, at least 50%, at least 60%, at least 70%, at least 80%, at least 90%, or at least 95% of the dendrimers contain at least 28 first terminal groups.

In some embodiments, at least 50%, at least 60%, at least 70%, at least 80%, at least 90%, or at least 95% of the dendrimers contain at least 28 second terminal groups. In some embodiments, at least 50%, at least 60%, at least 70%, at least 80%, at least 90%, or at least 95% of the dendrimers contain at least 29 second terminal groups.

In some embodiments, at least 50%, at least 60%, at least 70%, at least 80%, at least 90%, or at least 95% of the dendrimers contain at least 24 first terminal groups and at least 28 second terminal groups. In some embodiments, at least 50%, at least 60%, at least 70%, at least 80%, at least 90%, or at least 95% of the dendrimers contain at least 26 first terminal groups and at least 29 second terminal groups.

In some embodiments, the composition comprising a plurality of dendrimers or pharmaceutically acceptable salts thereof, comprises cabazitaxel residues in an amount of at least 20% w/w of the dendrimers present in the composition, at least 22% w/w, or at least 24% w/w. In some embodiments, the composition comprising a plurality of dendrimers or pharmaceutically acceptable salts thereof, comprises cabazitaxel residues in an amount of up to 30% w/w of the dendrimer, up to 28% w/w of the dendrimer or up to 26% w/w of the dendrimer. In some embodiments, the composition comprising a plurality of dendrimers or pharmaceutically acceptable salts thereof, comprises cabazitaxel residues in an amount in the range of from 20% w/w to 30% w/w, or from 23% w/w to 28% w/wr, or from 24% w/w to 26% w/w. The w/w % of the dendrimers which are cabazitaxel residues may be determined by any suitable means. In some embodiments, the w/w % of the dendrimers which are cabazitaxel residue may be determined by $^1$H NMR.

The present disclosure also provides pharmaceutical compositions, both for veterinary and for human medical use, which comprise the dendrimers of the present disclosure or a pharmaceutically acceptable salt thereof, with one or more pharmaceutically acceptable carriers, and optionally any other therapeutic ingredients, stabilisers, or the like. The carrier(s) must be pharmaceutically acceptable in the sense of being compatible with the other ingredients of the formulation and not unduly deleterious to the recipient thereof. In some embodiments, the composition is a pharmaceutical composition, and wherein the composition comprises a pharmaceutically acceptable excipient. The compositions of the present disclosure may also include polymeric excipients/additives or carriers, e.g., polyvinylpyrrolidones, derivatised celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, citrate, trehalose, binders, disintegrants, thickeners, lubricants, preservatives (including antioxidants), inorganic salts (e.g., sodium chloride), antimicrobial agents (e.g., benzalkonium chloride), sweeteners, antistatic agents, sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the present disclosure are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998), and in "Handbook of Pharmaceutical Excipients", Third Ed., Ed. A. H. Kibbe, Pharmaceutical Press, 2000.

In some embodiments, the composition is a solid composition which is suitable for reconstitution with a diluent. For example, the composition may be in the form of a powder or granules. Such compositions may be advantageous for transport and/or storage of the dendrimer prior to administration, e.g. assisting in providing for stability of the dendrimer.

In some embodiments, a stable composition is one in which the rate of cabazitaxel release from the dendrimer is less than 1%, less than 0.5%, less than 0.2%, or less than 0.1% of total cabazitaxel over a 4 hours period at room temperature, e.g. 25° C.).

Excipients used with such solid compositions may include, for example, a buffer or other pH-controlling agent. The pH controlling agent may for example be useful in preserving and/or maintaining chemical stability of the dendrimer, either in the solid composition itself, or in a subsequent reconstituted composition, if the solid composition is admixed with a diluent. In some embodiments, an acid is used in a solid composition which, following reconstitution with diluent, can provide a pH of at less than 6, or which can provide a pH in the range of less than 5, or which can provide a pH in the range of from 3.5 to 5.5, or which can provide a pH in the range of from 4 to 5, or which can provide a pH of about 4.5. In some embodiments, following reconstitution with a diluent, the reconstituted composition has a pH in the range of less than 5, in the range of from 3.5 to 5.5, in the range of from 4 to 5, or of about 4.5. In some embodiments, an acid is used which has an acidic group with a pKa in the range of from 4 to 5. In some embodiments, an acid such as citric acid is included in the composition.

In some embodiments, the solid composition comprises a bulking agent, for example a non-reducing sugar. In some embodiments, the sugar is a disaccharide. In some embodiments, the sugar is trehalose, mannitol, sorbitol or lactose.

In some embodiments, the solid composition comprises a sugar and an acid, and the composition is for reconstitution with a diluent. In some embodiments, the composition comprises trehalose and citric acid.

In some embodiments, the composition comprises dendrimer and a sugar (preferably trehalose) at a weight ratio in the range of from 1:1 to 1:3, or at a weight ratio of about 1:2. In some embodiments, the composition comprises dendrimer and acid (preferably citric acid) in a weight ratio in the range of from 1:0.5 to 1:2, or about 1:1, or 1:0.96. In some embodiments, the weight ratio of dendrimer:sugar:acid is about 100:200:96. In some embodiments, the weight ratio of dendrimer:sugar:acid in the composition is about 100:200:96, and the composition comprises cabazitaxel residues in an amount of from 23% w/w to 28% w/w of the dendrimer.

In some embodiments, the composition is produced by lyophilisation, i.e. it is a lyophilisate. In some embodiments the composition is a solid lyophilisate comprising the dendrimer or a pharmaceutically acceptable salt thereof, a sugar and an acid. In some embodiments, the composition is a solid lyophilisate comprising the dendrimer or a pharmaceutically acceptable salt thereof, trehalose and citric acid.

In some embodiments, the composition is a liquid composition, e.g. a reconstituted composition, which is suitable for administration by, for example, injection or infusion. For example, the composition may be a reconstituted composition produced by admixing of a solid composition as discussed above with a diluent such as saline or WFI (water for injection).

In some embodiments, the liquid composition is a reconstituted composition which is sufficiently stable at ambient conditions (e.g. at about 25° C.) for use up to 2 hours, up to 4 hours, up to 6 hours, up to 12 hours, up to 24 hours, or up to 48 hours, or up to 1 week following reconstitution. In some embodiments, the liquid composition is a reconstituted composition which is sufficiently stable on refrigeration (e.g. at about 4° C.) for use up to 2 hours, up to 4 hours, up to 6 hours, up to 12 hours, or up to 24 hours, or up to 48 hours, or up to 1 week following reconstitution. In some embodiments, the liquid composition is a reconstituted composition which is sufficiently stable when protected from light for use up to 2 hours, up to 4 hours, up to 6 hours, up to 12 hours, or up to 24 hours, or up to 48 hours, or up to 1 week following reconstitution.

It has been found that, following reconstitution but before transferring into an infusion bag (saline), the data show that a reconstituted solution according to the invention is stable (less than 0.1% cabazitaxel release) for at least 4 hours at room temperature (25±5° C.).

In some embodiments, the liquid composition is one in which the rate of cabazitaxel release from the dendrimer when present in the composition is less than 1%, less than 0.5%, less than 0.2%, or less than 0.1% of total cabazitaxel over a 4 hours period at room temperature, e.g. 25° C.).

In some embodiments, the liquid composition is a reconstituted composition present in an infusion bag. In some embodiments, the liquid composition is a reconstituted composition present in a syringe.

It will be appreciated that the compositions described above, can be utilised with drug-dendrimer conjugates other than those described in the first aspect, for example with other drug-dendrimer conjugates in which the pharmaceutically active agent is linked through a hydroxyl group to the dendrimer via a diglycolyl linker.

Accordingly, also provided herein is a pharmaceutical composition comprising a) a dendrimer comprising a core unit, building units, a plurality of first terminal groups (T1) each comprising a residue of a pharmaceutically active agent comprising a hydroxyl group which is covalently attached to a diglycolyl linker group; and a plurality of second terminal groups (T2) each comprising a pharmacokinetic modifier; wherein the first and second terminal groups are covalently attached to outer building units; and b) an acid. In some embodiments, the pharmaceutically active agent is an oncology agent, for example a taxane such as docetaxel or cabazitaxel. In some embodiments, the pharmacokinetic modifier comprises a PEG or PEOX group. In some embodiments, the pharmacokinetic modifier comprises a PEG group. In some embodiments the core is a BHALys group. In some embodiments the building units are lysine residues or an analogue thereof. In some embodiments, the dendrimer is a five generation building unit dendrimer. In some embodiments, the acid is citric acid. In some embodiments, the composition comprises c) a sugar, for example a disaccharide, e.g. trehalose. In some embodiments, the composition is a solid composition. In some embodiments, the composition is produced by lyophilisation, i.e. it is a solid lyophilisate. In some embodiments, the composition is for reconstitution with a diluent. In some embodiments, the composition is a liquid composition, e.g. a reconstituted composition, which is suitable for administration by, for example, injection or infusion. For example, the composition may be a reconstituted composition produced by admixing of a solid composition as discussed above with a diluent such as saline or WFI (water for injection). The dendrimers of the present disclosure may be presented in compositions including those suitable for inhalation to the lung, by aerosol, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the dendrimer into association with a carrier that constitutes one or more accessory ingredients. In general, the compositions are prepared by bringing the dendrimer into association with a liquid carrier to form a solution or a suspension, or alternatively, bring the dendrimer into association with composition components suitable for forming a solid, optionally a particulate product, and then, if warranted, shaping the product into a desired delivery form. Solid compositions of the present disclosure, when particulate, will typically comprise particles with sizes ranging from about 1 nanometer to about 500 microns. In general, for solid compositions intended for intravenous administration, particles will typically range from about 1 nm to about 10 microns in diameter. The composition may contain dendrimer of the present disclosure that are nanoparticulate having a particulate diameter of below 1000 nm, for example, between 5 and 1000 nm, especially 5 and 500 nm, more especially 5 to 400 nm, such as 5 to 50 nm and especially between 5 and 20 nm. In one example, the composition contains dendrimers with a mean size of between 5 and 20 nm. In some embodiments, the dendrimer is polydispersed in the composition, with PDI of between 1.01 and 1.8, especially between 1.01 and 1.5, and more especially between 1.01 and 1.2. In one example, the dendrimer is monodispersed in the composition.

In some preferred embodiments, the composition is for patenteral delivery. For example, in one embodiment, the composition may be a sterile, lyophilized composition that is suitable for reconstitution in an aqueous vehicle prior to injection.

In one embodiment, a composition suitable for parenteral administration conveniently comprises a sterile aqueous preparation of the dendrimer, which may for example be prepared so as to be isotonic with the blood of the recipient.

Pharmaceutical compositions are also provided which are suitable for administration as an aerosol, by inhalation. These compositions comprise a solution or suspension of the desired dendrimer or a salt thereof. The desired composition may be placed in a small chamber and nebulized. Nebulization may be accomplished by compressed air or by ultrasonic energy to form a plurality of liquid droplets or solid particles comprising the dendrimers or salts thereof.

In some embodiments, the composition may be formulated for administration as an infusion. In some embodiments, the composition may be formulated for administration as a bolus dose. In some embodiments, the composition is formulated for administration as an infusion over a time period of up to 30 minutes, or is formulated for administration as a bolus over a time period of up to 5 minutes.

As discussed below, the dendrimers of the present disclosure may for example be administered in combination with one or more additional pharmaceutically active agents. Thus, in some embodiments, the composition comprises a dendrimer as defined herein, or a pharmaceutically acceptable salt thereof, one or more pharmaceutically acceptable carriers, and one or more additional pharmaceutically active agents, e.g. an additional oncology agent, a small molecule cytotoxic, a checkpoint inhibitor, an antibody therapy. In some embodiments, the composition comprises a dendrimer as defined herein, or a pharmaceutically acceptable salt thereof, and an additional oncology agent, such as gemcitabine. Not only can the dendrimers of the present disclosure be administered with other chemotherapy drugs but may also be administered in combination with other medications such as corticosteroids, anti-histamines, analgesics and drugs that aid in recovery or protect from hematotoxicity, for example, cytokines.

In some embodiments, the composition is for parenteral infusion as part of a chemotherapy regimen. In these embodiments, the composition may for example be substantially free or entirely free of solubilisation excipients, especially solubilisation excipients such as a polyethoxylated castor oil (e.g. such as that sold under the trade name CREMOPHOR® or KOLLIPHOR®), or a polyethoxylated sorbitan monooleate (such as that sold under the trade name POLYSORBATE 80®). Solubilisation excipients are additives which aid dissolution of the dendrimer in the solvent or solvents. In one embodiment the composition is substantially free or entirely free of a polyethoxylated castor oil (e.g. such as that sold under the trade name CREMOPHOR® or KOLLIPHOR®) and a polyethoxylated sorbitan monooleate (e.g. such as POLYSORBATE 80®). In one embodiment, the composition is substantially or entirely free of a solubilisation excipient. By avoiding the use of solubilisation excipients, the composition of dendrimer is less likely to cause side effects such as acute or delayed hypersensitivity including life-threatening anaphylaxis and/or severe fluid retention, and/or remove the need for steroid pre-treatment.

Methods of Use

The dendrimers of the present disclosure may be used to treat or prevent any disease, disorder or symptom that the unmodified pharmaceutically active agent can be used to treat or prevent. Accordingly, there is also provided a dendrimer or pharmaceutical composition as described herein for use in therapy.

In some embodiments, the dendrimer is used in a method of treating or preventing cancer, for example for suppressing the growth of a tumour. In some embodiments the dendrimer is for use in the treatment of cancer. There is also provided a method of treating cancer comprising administering to a subject in need thereof a therapeutically effective amount of the dendrimer. There is also provided use of a dendrimer as defined herein, or of a composition as defined herein, in the manufacture of a medicament for the treatment of cancer.

In some embodiments, the cancer is a solid tumour. The cancer may be a primary or metastatic tumour. In some embodiments the cancer is a primary tumour. In some embodiments the cancer is a metastatic tumour.

In some embodiments, the cancer, is selected from the group consisting of breast cancer, ovarian cancer (e.g. recurrent ovarian cancer), pancreatic cancer, testicular cancer (e.g. cis-platin-resistant germ cell cancer), prostate cancer (e.g. bone metastatic prostate cancer, prostatic neoplasms, hormone-refractory prostate cancer, castration resistant prostate cancer, advanced prostate cancer), dedifferentiated liposarcoma, urothelial carcinoma of the urinary bladder (e.g. urothelium transitional cell carcinoma (TCCU)), adrenocortical carcinoma, brain cancer (e.g. recurrent malignant glioma), AML (acute myeloid leukemia) and CLL (chronic lymphocytic leukemia). In some embodiments, the cancer is prostate cancer, pancreatic cancer, ovarian cancer or breast cancer. In some embodiments the cancer is prostate cancer, for example hormone-refractory prostate cancer, or for example metastatic castration-resistant prostate cancer (mCRPC). In some embodiments the cancer is breast cancer. In some embodiments, the cancer is pancreatic cancer. In some embodiments, the cancer is ovarian cancer. In some embodiments, the cancer is a tumour of the sweat glands, for example a digital papillary adenocarcinoma.

In some embodiments, the dendrimer which is used in therapy (e.g. in cancer therapy) has a core which is:

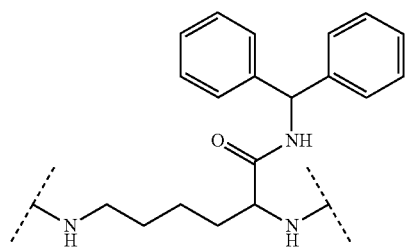

In some embodiments, the dendrimer which is used in therapy (e.g. in cancer therapy) has building units which are each:

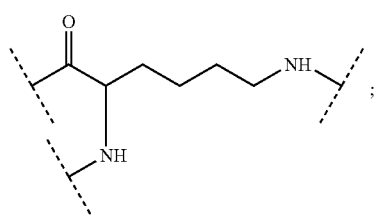

wherein the acyl group of each building unit provides a covalent attachment point for attachment to the core or to a previous generation building unit; and wherein each nitrogen atom provides a covalent attachment point for covalent attachment to a subsequent generation building unit, a first terminal group or a second terminal group.

In some embodiments, the dendrimer which is used in therapy (e.g. in cancer therapy) has first terminal groups (T1) which are each:

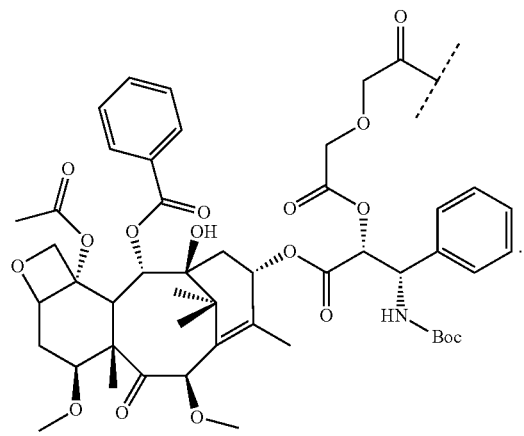

In some embodiments, the dendrimer used in therapy (e.g. in cancer therapy) has second terminal groups which are each

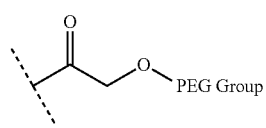

and wherein the PEG group is a methoxy-terminated PEG having a mean molecular weight in the range of from about 1750 to 2500 Daltons.

In some embodiments, the dendrimer used in therapy (e.g. in cancer therapy) has from 26 to 32 first terminal groups, and from 28 to 32 second terminal groups.

In some embodiments, the dendrimer used in therapy (e.g. in cancer therapy) is

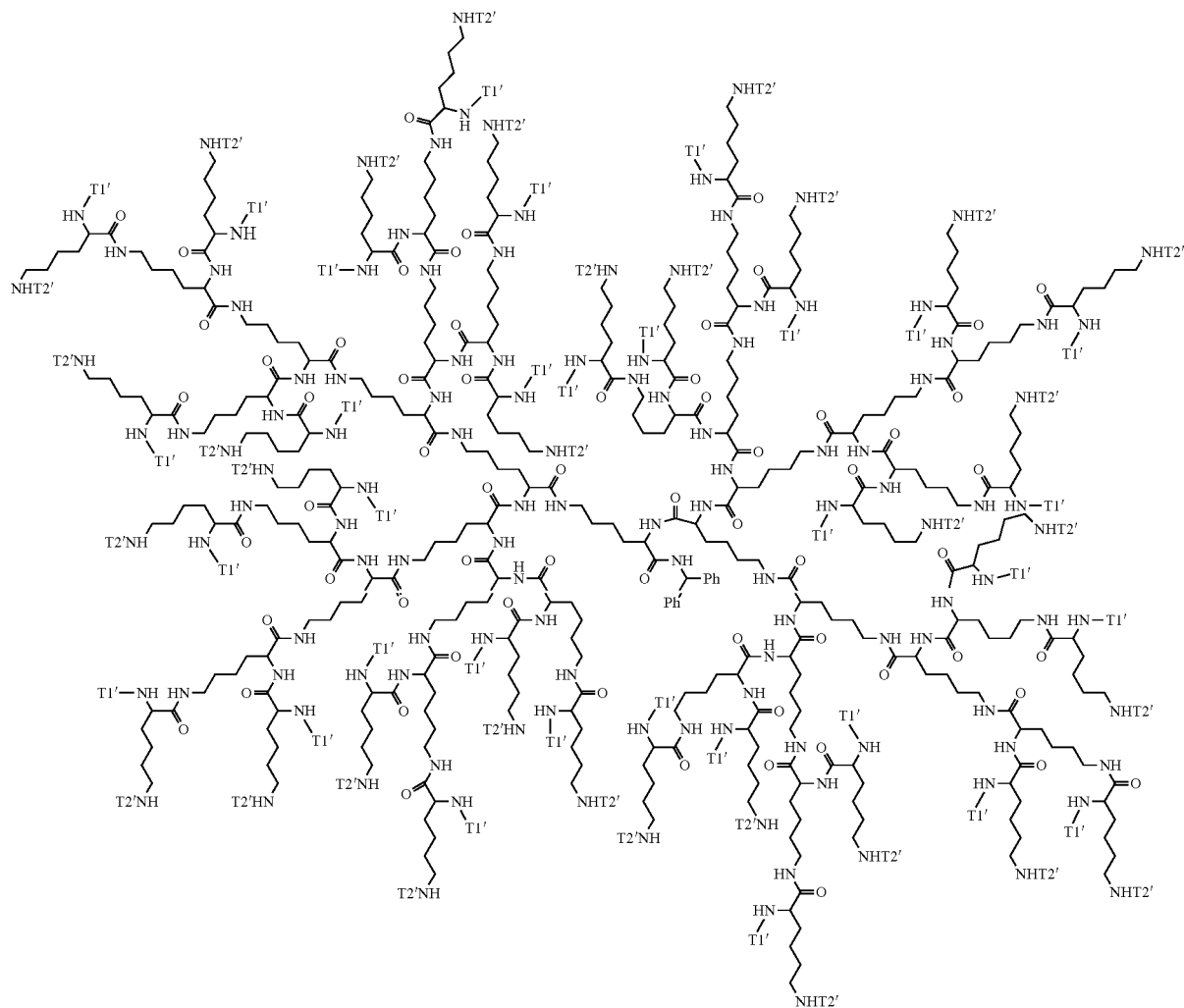

in which T1' represents a first terminal group which is

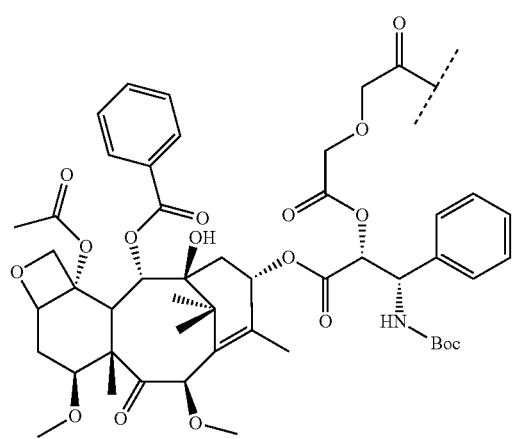

or T1' represents H, wherein less than 5 of T1' are H; and T2' represents a second terminal group which is

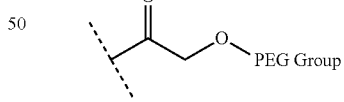

wherein the PEG group is a methoxy-terminated PEG having a molecular weight in the range of from about 1750 to 2500 Daltons, or T2' represents H, and wherein less than 5 of T2' are H.

Drugs are often co-administered with other drugs in combination therapy, especially during chemotherapy. Accordingly, in some embodiments the dendrimer is administered in combination with one or more further therapeutic/pharmaceutically active agents, for example one or more further anti-cancer agents. The dendrimer and the one or more further therapeutic/pharmaceutically active agents may be administered simultaneously, subsequently or separately. For example, they may be administered as part of the same composition, or by administration of separate compositions. The one or more further pharmaceutically active agents may for example be anti-cancer agents for therapy of prostate cancer or breast cancer, or e.g. for therapy of pancreatic cancer or ovarian cancer. Examples of further pharmaceutically active agents include chemotherapeutic and cytotoxic agents, immune-oncology agents (such as checkpoint inhibitors), and antibody therapies. Examples of further pharmaceutically active agents include paclitaxel, docetaxel, abraxane, clarithromycin, vinflunine, bavituximab, tocotrienol, gemcitabine, capecitabine, carboplatin, oxaliplatin, niraparib, folinic acid, 5-fluorouracil, irinotecan, tamsulosin, ADT, G-CSF, an LHRH antagonist, bicalutamide, enzlutamide, clarithromycin, vinflunine, bacituximab and bevacizumab.

The current label for JEVTANA® brand cabazitaxel (free cabazitaxel) states that it is administered as a one-hour intravenous infusion in combination with oral prednisone 10 mg administered daily throughout JEVTANA® brand cabazitaxel treatment. In addition, premedication is recommended at least 30 minutes prior to each dose of JEVTANA® brand cabazitaxel with the following intravenous medications to reduce the risk and/or severity of hypersensitivity (i) antihistamine (dexchlorpheniramine 5 mg, or diphenhydramine 25 mg or equivalent antihistamine), (ii) corticosteroid (dexamethasone 8 mg or equivalent steroid), and (iii) H2 antagonist (ranitidine 50 mg or equivalent H2 antagonist).

In some embodiments, the dendrimer or composition comprising the dendrimer is not administered in combination with a steroid or other medicament used in the delivery of JEVTANA® brand cabazitaxel. In some embodiments, the dendrimer or composition comprising the dendrimer is not administered as part of a regime requiring premedication. In some embodiments, the dendrimer or composition comprising the dendrimer is not administered in combination with a medication which reduces the risk and/or severity of hypersensitivity, is not administered as part of a regime requiring premedication with a medication which reduces the risk and/or severity of hypersensitivity, and is not administered as part of a regime requiring ongoing treatment with a medication which reduces the risk and/or severity of hypersensitivity. In some embodiments, the dendrimer or composition comprising the dendrimer is not administered in combination with an antihistamine, corticosteroid or H2 antagonist, and is not administered as part of a regime requiring premedication with an antihistamine, corticosteroid or H2 antagonist, and is not administered as part of a regime requiring ongoing treatment with an antihistamine, corticosteroid (e.g. prednisone, prednisolone), immune suppressant, or H2 antagonist.

It will be appreciated that a therapeutically effective amount refers to a dendrimer being administered in an amount sufficient to alleviate or prevent to some extent one or more of the symptoms of the disorder or condition being treated. A therapeutically effective amount of dendrimer may be referred to based on, for example, the amount of dendrimer administered. Alternatively, it may be determined based on the amount of active agent (cabazitaxel) which the dendrimer is theoretically capable of delivering, e.g. based on the loading of cabazitaxel on the dendrimer.

In some embodiments, the amount of dendrimer administered is sufficient to deliver between 5 and 100 mg of active agent/m$^2$, between 10 and 100 mg of active agent/m$^2$, between 5 and 50 mg of active agent/m$^2$, between 5 and 40 mg of active agent/m$^2$, between 5 and 30 mg of active agent/m$^2$, between 5 and 25 mg of active agent/m$^2$, between 5 and 20 mg of active agent/m$^2$, between 10 and 50 mg of active agent/m$^2$, between 20 to 40 mg of active agent/m$^2$ between 15 and 35 mg of active agent/m$^2$, between 10 and 20 mg/m$^2$, between 20 and 30 mg/m$^2$, between 20 and 50 mg/m$^2$, between 25 and 50 mg/m$^2$, between 30 and 40 mg/m$^2$, between 25 and 35 mg of active agent/m$^2$, between 50 and 100 mg of active agent/m$^2$, between 50 and 75 mg of active agent/m$^2$, or between 75 and 100 mg of active agent/m$^2$. Cabazitaxel is indicated for use at 20-25 mg/m$^2$ and similar or slightly higher doses of active agent have been demonstrated to be effective for the dendrimer in the comparative mouse studies below. A dose of active agent of 10 mg/kg in a mouse should be approximately equivalent to a human dose of 30 mg/m$^2$ (FDA guidance 2005). (To convert human mg/kg dose to mg/m$^2$, the figure may be multiplied by 37, FDA guidance 2005).

In some embodiments, the amount of dendrimer administered delivers an amount of cabazitaxel to a patient which is in the range of from 0.5 to 3 times the amount of cabazitaxel delivered upon administration of 20-25 mg/m$^2$ free cabazitaxel. In some embodiments, the amount of dendrimer administered delivers an amount of cabazitaxel to a patient which is in the range of from 1 to 2 times the amount of cabazitaxel delivered upon administration of 20-25 mg/m$^2$ free cabazitaxel. In some embodiments, the amount of dendrimer administered delivers an amount of cabazitaxel to a patient which is in the range of from 0.5 to less than 1 times the amount of cabazitaxel delivered upon administration of 20-25 mg/m$^2$ free cabazitaxel. In some embodiments, the amount of dendrimer administered delivers an amount of cabazitaxel to a patient which is in the range of from 0.5 to 1.5 times the amount of cabazitaxel delivered upon administration of 20-25 mg/m$^2$ free cabazitaxel. In some embodiments, the amount of dendrimer administered delivers an amount of cabazitaxel to a patient which is in the range of from 0.8 to 1.2 times the amount of cabazitaxel delivered upon administration of 20-25 mg/m$^2$ free cabazitaxel. In some embodiments, the amount of dendrimer administered delivers substantially an equivalent amount of cabazitaxel to that delivered on administration of an authorised dosage of free cabazitaxel (e.g. JEVTANA® brand cabazitaxel). For example, as discussed above, recommended dosage levels for cabazitaxel are 20-25 mg/m$^2$. In some embodiments, the amount of dendrimer administered is capable of delivering an amount of cabazitaxel to a patient substantially equivalent to administration of 20-25 mg/m$^2$ free cabazitaxel. The amount of dendrimer administered may for example be determined with reference to the amount of cabazitaxel which the dendrimer is capable of delivering (i.e. cabazitaxel loading).

In some embodiments, a therapeutically effective amount of the dendrimer is administered to a subject in need thereof at a predetermined frequency. In some embodiments, the dendrimer is administered to a subject in need thereof according to a dosage regimen in which the dendrimer is administered once per one to four weeks. In some embodiments, the dendrimer is administered to a subject in need thereof according to a dosage regimen in which the dendrimer is administered once per three to four weeks.

In some embodiments, the dendrimer or pharmaceutical composition is administered as a fast infusion or as a bolus. In some embodiments, the infusion time is over a period of less than 1 hour, less than 30 minutes or less than 20 minutes, for example it may be administered over a period of about 20 minutes, 15 minutes or 10 minutes. In some embodiments, the administration may be as a bolus, for example it may be administered over a time period suitable for a bolus injection, e.g. a time period of up to about 5 minutes, e.g. in the range of from 5 seconds to 5 minutes.

It has been surprisingly found that a dendrimer of the present disclosure has increased efficacy in comparison to the direct administration of the free drug.

An equivalent dose of free cabazitaxel is the equivalent amount of free cabazitaxel to the amount of cabazitaxel contained (loaded) in the dose of dendrimer to be administered.

As used herein, the term "free" refers to a drug, i.e., cabazitaxel, which has not been previously conjugated to a dendrimer. For example, the direct administration of free cabazitaxel refers to the direct administration of cabazitaxel molecules that are not administered as being conjugated to a dendrimer. An example of such a therapy is JEVTANA® brand cabazitaxel. As used herein, the terms "unconjugated" and "released" refer to a drug, i.e. cabazitaxel, which has dissociated or been cleaved from a dendrimer. This dissociation or cleaving may occur in vivo following administration of the drug-dendrimer conjugate.

In some embodiments, administration of the dendrimer provides enhanced clinical efficacy in comparison to administration of an equivalent dose of free cabazitaxel.

In some embodiments, administration of a course of the dendrimer provides enhanced clinical efficacy in comparison to three-weekly administration of 20 or 25 mg/m$^2$ cabazitaxel.

In some embodiments, administration of the dendrimer provides for:

alleviating or eliminating symptoms associated with cancer, reducing cancerous tissue size, increasing progression-free survival, and/or slowing or preventing metastasis, in at least 10%, at least 20%, at least 30%, at least 40% or at least 50% of the patient population.

Oncology drugs often have significant side effects that are due to off-target toxicity such as hematologic toxicity, neurological toxicity, cardiotoxicity, hepatotoxicity, nephrotoxicity, ototoxicity and encephalotoxicity. For example, taxanes such as cabazitaxel may cause the following adverse effects: infections, neutropenia, anaemia, febrile neutropenia, hypersensitivity, thrombocytopenia, myelotoxicity, myelosuppression, neuropathy, dysgeusia, dyspnoea, constipation, anorexia, nail disorders, fluid retention, asthenia, pain, nausea, diarrhea, vomiting, fatigue, non-specific neuro cognitive problems, vertigo, encephalopathy, mucositis, alopecia, skin reactions and myalgia.

In some embodiments, administration of the dendrimer provides reduced toxicity in comparison to administration of an equivalent dose of free cabazitaxel. The toxicity of a drug refers to the degree to which damage is caused to the organism, and is measured by its effect off target. In oncology, one such measurement of toxicity in animal models is weight loss, which determines the maximum tolerated dose (MTD). In humans, toxicity is commonly determined by specified adverse events (AE), which typically include the dose limiting toxicity. It will be appreciated that usually in oncology, there is a narrow therapeutic window and off-target toxicities are considered a normal side effect of killing tumour cells.

In some embodiments, administration of the dendrimer provides reduced toxicity in comparison to administration of an equivalent dose of free cabazitaxel when used in a method of treatment of cancer, for example, in the treatment of cancer, such as breast cancer, ovarian cancer, pancreatic cancer or prostate cancer, e.g. hormone-refractory prostate cancer, metastatic castration-resistant prostate cancer (mCRPC).

In some embodiments, administration of the dendrimer provides reduced toxicity in comparison to three-weekly administration of 20 or 25 mg/m$^2$ cabazitaxel.

In some embodiments, administration of the dendrimer provides reduced toxicity in comparison to three-weekly administration of 20 or 25 mg/m$^2$ cabazitaxel, when used in a method of treatment of cancer, for example, in the treatment of cancer, such as breast cancer, ovarian cancer, pancreatic cancer or prostate cancer, e.g. hormone-refractory prostate cancer, metastatic castration-resistant prostate cancer (mCRPC).

In some embodiments, administration of a course of the dendrimer provides reduced toxicity in comparison to three-weekly administration of 20 or 25 mg/m$^2$ cabazitaxel.

In some embodiments, administration of a course of the dendrimer provides reduced toxicity in at least 10%, at least 20%, at least 30%, at least 40% or at least 50% of the patient population.

Toxicology studies carried out with a dendrimer of the present disclosure indicate that the dendrimer is likely to induce less neutropenia, and therefore be less toxic in the clinic, compared with the administration of an equivalent dose of free cabazitaxel.

Accordingly, in some embodiments, administration of the dendrimer provides reduced bone marrow toxicity, for example in the form of reduced neutropenia, lymphopenia, anemia and/or thrombocytopenia, in comparison to administration of an equivalent dose of free cabazitaxel. In some embodiments, administration of the dendrimer provides reduced neutropenia in comparison to administration of an equivalent dose of free cabazitaxel.

In some embodiments, administration of a course of the dendrimer provides reduced neutropenia, lymphopenia, anemia, and/or thrombocytopenia in comparison to three-weekly administration of 20 or 25 mg/m$^2$ cabazitaxel.

In some embodiments, administration of the dendrimer provides reduced bone marrow toxicity, for example in the form of reduced neutropenia, lymphopenia, anemia and/or thrombocytopenia, in comparison to administration of an equivalent dose of free cabazitaxel, when used in a method of treatment of cancer. In some embodiments, administration of the dendrimer provides reduced neutropenia in comparison to administration of an equivalent dose of free cabazitaxel, when used in a method of treatment of cancer, for example, in the treatment of cancer, such as breast cancer, ovarian cancer, pancreatic cancer or prostate cancer, e.g. hormone-refractory prostate cancer, metastatic castration-resistant prostate cancer (mCRPC). In some embodiments, administration of a course of the dendrimer provides reduced neutropenia in comparison to three-weekly administration of 20 or 25 mg/m$^2$ cabazitaxel, when used in a method of treatment of cancer, for example, in the treatment of cancer, such as breast cancer, ovarian cancer, pancreatic cancer or prostate cancer, e.g. hormone-refractory prostate cancer, metastatic castration-resistant prostate cancer (mCRPC)

In some embodiments, the dendrimer provides a reduction in toxicity as measured by the number of patients having specified AE (e.g. infections (cystitis, upper respiratory tract, herpes zoster, candidiasis, sepsis, influenza, UTI) fever, neutropenia, anaemia, febrile neutropenia, thrombocytopenia, leukopenia, myelotoxicity, myelosuppression, neuropathy, hypersensitivity, dysgeusia, gastrointestinal toxicity, dyspnoea, cough, abdominal pain, constipation, anorexia, nail disorders, fluid retention, asthenia, pain, nausea, diarrhea, vomiting, fatigue, non-specific neuro cognitive problems, headache, vertigo, back pain, arthralgia, encephalopathy, mucositis, alopecia, skin reactions and myalgia), by at least 10%, at least 20%, at least 30%, at least 40%, at least 50%, at least 60%, at least 70%, at least 80%, or at least 90%, in comparison to the direct administration of an equivalent dose of the free pharmaceutically active agent. In one example, administration of the dendrimer provides less than 95%, less than 90%, less than 80%, less than 70%, less than 60%, less than 50%, less than 40%, less than 30%, less than 20%, or less than 10% toxicity in comparison to the direct administration of an equivalent dose of free cabazitaxel.

The dendrimers of the present disclosure surprisingly achieve a sustained pharmacokinetic profile for unconjugated or released drug. This sustained pharmacokinetic profile indicates that the drug will be present in vivo at therapeutically effective levels for longer periods of time. It will be appreciated that exposure to the drug for a longer period of time is desirable as it may prolong the therapeutic effect of the drug and allow for reduced frequency of dosing. In some embodiments, administration of the dendrimer provides a therapeutically effective plasma concentration of cabazitaxel for a longer period of time, in comparison to administration of an equivalent dose of free cabazitaxel.

In addition to having a sustained in vivo pharmacokinetic profile providing comparatively longer therapeutic levels of exposure, the dendrimers also achieve comparatively low $C_{max}$ levels upon in vivo administration.

In some embodiments, administration of the dendrimer provides a lower maximal concentration ($C_{max}$) of unconjugated/released drug in comparison to direct administration of an equivalent dose of free drug. The maximal concentration ($C_{max}$) of drug is the maximum (or peak) serum concentration that a drug achieves in a specified compartment or test area of the body after the drug has been administered and before the administration of a second dose. It will be appreciated that, whilst it is important to be able to dose a pharmaceutical agent at a level sufficient to achieve therapeutic concentration levels, if the maximum concentration levels reached are high, the risk of encountering certain off-target effects, side-effects and toxicity increase. This is particularly an issue for compounds which have a short half-life, since in such cases, in order to provide therapeutically effective levels of the active agent for a prolonged period of time, it may be necessary to increase the dose and thus the $C_{max}$ such that the likelihood of side effects increases. Accordingly, it is highly desirable to be able to deliver a pharmaceutically active agent in a form which provides therapeutically effective levels for a sustained period of time, whilst at the same time avoiding dosing at levels that achieve very high maximum concentrations ($C_{max}$) in vivo.

In some embodiments, the dendrimer has a lower maximal concentration ($C_{max}$) of unconjugated/released cabazitaxel in comparison to the direct administration of an equivalent dose of free cabazitaxel. In some embodiments, the dendrimer has a lower maximal concentration ($C_{max}$) of released/unconjugated cabazitaxel in comparison to the direct administration of an equivalent dose of free cabazitaxel when used in a method of treatment, for example, in the treatment of cancer, such as breast cancer, ovarian cancer, pancreatic cancer or prostate cancer, e.g. hormone-refractory prostate cancer, metastatic castration-resistant prostate cancer (mCRPC).

In some embodiments, the dendrimer has a lower maximal concentration ($C_{max}$) of unconjugated/released cabazitaxel in comparison to the direct administration of a dose of 20 or 25 mg/m² cabazitaxel. In some embodiments, the dendrimer has a lower maximal concentration ($C_{max}$) of released/unconjugated cabazitaxel in comparison to the direct administration of a dose of 20 or 25 mg/m² cabazitaxel, when used in a method of treatment, for example, in the treatment of cancer, such as breast cancer, ovarian cancer, pancreatic cancer or prostate cancer, e.g. hormone-refractory prostate cancer, metastatic castration-resistant prostate cancer (mCRPC).

In some embodiments, administration of the dendrimer provides a maximal concentration ($C_{max}$) of drug (i.e. released/unconjugated cabazitaxel) which is less than 90%, less than 50%, less than 40%, less than 30%, less than 20%, less than 10%, or less than 5% of the $C_{max}$ which results from direct administration of an equivalent dose of free cabazitaxel.

In some embodiments, an amount of dendrimer is administered which is sufficient to provide a maximal concentration ($C_{max}$) of unconjugated Cabazitaxel of less than 800, less than 500, less than 200, less than 100, less than 50, less than 25, or less than 20 ng/mL. In some embodiments, an amount of dendrimer is administered which provides a maximal concentration ($C_{max}$) of unconjugated/released cabazitaxel of about 10, about 15, about 20, about 25, about 30, about 35, about 40, about 45, about 50, about 55, about 60, about 65, about 70, about 75, about 80, about 85, about 80, about 95 or about 100 ng/mL.

AUC is the area under the curve in a plot of drug concentration in blood plasma versus time. The AUC represents the total drug exposure over time. It will be appreciated that the AUC is normally proportional to the total amount of drug delivered to the body.

It will be appreciated that, following administration of the dendrimer, and as some of the cabazitaxel is released from the dendrimer, there is both unbound cabazitaxel present in the body, and cabazitaxel present which is still bound to dendrimer.

In some embodiments, administration of the dendrimer provides greater AUC of total cabazitaxel (i.e. both dendrimer-bound cabazitaxel and released cabazitaxel), in comparison to direct administration of an equivalent dose of free cabazitaxel.

In some embodiments, administration of the dendrimer provides greater AUC of total cabazitaxel (i.e. both dendrimer-bound cabazitaxel and released cabazitaxel), in comparison to the direct administration of an equivalent dose of free cabazitaxel when used in a method of treatment, for example, in the treatment of cancer, such as breast cancer, ovarian cancer, pancreatic cancer or prostate cancer, e.g. hormone-refractory prostate cancer, metastatic castration-resistant prostate cancer (mCRPC). In some embodiments, administration of the dendrimer provides at least 1.5 times, at least 2 times, at least 3 times, at least 4 times, or at least 5 times the AUC of total cabazitaxel (i.e. both dendrimer-bound cabazitaxel and released cabazitaxel) in comparison to the direct administration of an equivalent dose of free cabazitaxel.

In some embodiments, administration of the dendrimer provides greater AUC of total cabazitaxel (i.e. both dendrimer-bound cabazitaxel and released cabazitaxel in comparison to the direct administration of a dose of 20 or 25 mg/m² cabazitaxel, when used in a method of treatment, for example, in the treatment of cancer, such as breast cancer, ovarian cancer, pancreatic cancer or prostate cancer, e.g.

hormone-refractory prostate cancer, metastatic castration-resistant prostate cancer (mCRPC). In some embodiments, administration of the dendrimer provides at least 1.5 times, at least 2 times, at least 3 times, at least 4 times, or at least 5 times the AUC of total cabazitaxel (i.e. both dendrimer-bound cabazitaxel and released cabazitaxel) in comparison to the in comparison to the direct administration of a dose of 20 or 25 mg/m² cabazitaxel.

In some embodiments, an amount of dendrimer is administered which provides an AUC of total cabazitaxel (i.e. both dendrimer-bound cabazitaxel and released cabazitaxel) of at least 100,000, at least 110,000, at least 120,000, at least 130,000, at least 140,000, at least 150,000, at least 160,000, at least 170,000, at least 180,000, at least 190,000, or at least 200,000 ng·h/mL. In some embodiments, an amount of dendrimer is administered which provides an AUC of total cabazitaxel (i.e. both dendrimer-bound cabazitaxel and released cabazitaxel) of about 150,000, about 160,000, about 170,000, about 180,000, about 190,000, about 200,000, about 210,000, about 220,000 or about 230,000 ng·h/mL.

In some embodiments, administration of the dendrimer provides equivalent or greater AUC of unconjugated/released cabazitaxel in comparison to the direct administration of an equivalent dose of free cabazitaxel.

In some embodiments, administration of the dendrimer provides at least 1.1 times, at least 1.2 times, at least 1.3 times, at least 1.4 times, at least 1.5 times, at least 1.6 times, at least 1.7 times, at least 1.8 times, at least 1.9 times, at least 2 times, at least 2.5 times, at least 3 times, at least 3.5 times, or at least 4 times, the AUC of unconjugated/released cabazitaxel in comparison to the direct administration of an equivalent dose of free cabazitaxel.

In some embodiments, administration of the dendrimer provides from 0.8 times to 1.2 times the AUC of unconjugated/released cabazitaxel, in comparison to the direct administration of an equivalent dose of free cabazitaxel.

In some embodiments, administration of the dendrimer provides equivalent or greater AUC of unconjugated/released cabazitaxel in comparison to the direct administration of an equivalent dose of free cabazitaxel, when used in a method of treatment, for example, in the treatment of cancer, such as breast cancer, ovarian cancer, pancreatic cancer or prostate cancer, e.g. hormone-refractory prostate cancer, metastatic castration-resistant prostate cancer (mCRPC).

In some embodiments, administration of the dendrimer provides equivalent or greater AUC of unconjugated/released cabazitaxel in comparison to the direct administration of a dose of 20 or 25 mg/m² cabazitaxel.

In some embodiments, administration of the dendrimer provides at least 1.1 times, at least 1.2 times, at least 1.3 times, at least 1.4 times, at least 1.5 times, at least 1.6 times, at least 1.7 times, at least 1.8 times, at least 1.9 times, at least 2 times, at least 2.5 times, at least 3 times, at least 3.5 times, or at least 4 times, the AUC of unconjugated/released cabazitaxel in comparison to the direct administration of a dose of 20 or 25 mg/m² cabazitaxel.

In some embodiments, administration of the dendrimer provides from 0.8 times to 1.2 times the AUC of unconjugated/released cabazitaxel, in comparison to the direct administration of a dose of 20 or 25 mg/m² cabazitaxel.

In some embodiments, administration of the dendrimer provides equivalent or greater AUC of unconjugated/released cabazitaxel in comparison to the direct administration of a dose of 20 or 25 mg/m² cabazitaxel, when used in a method of treatment, for example, in the treatment of cancer, such as breast cancer, ovarian cancer, pancreatic cancer or prostate cancer, e.g. hormone-refractory prostate cancer, metastatic castration-resistant prostate cancer (mCRPC).

In some embodiments, an amount of dendrimer is administered which provides an AUC of released/unconjugated cabazitaxel of at least 500, at least 600, at least 700, at least 800, at least 900, at least 1000, at least 1100, at least 1200, at least 1300, at least 1400, at least 1500, at least 1750, at least 2000, at least 2500, at least 3000, at least 3500, or at least 4000 ng·h/mL.

In some embodiments, an amount of dendrimer is administered which provides an AUC of released/unconjugated cabazitaxel of about 500, about 600, about 700, about 800, about 900, about 1000, about 1100, about 1200, about 1300, about 1400, about 1500, about 1600, about 1700, about 1800, about 2000, about 2500, about 3000, about 3500, or about 4000 g·h/mL.

Free cabazitaxel is characterized by a triphasic elimination profile with an initial-phase half-life averaging 4 minutes, followed by an intermediate-phase half-life of 2 hours, and a prolonged terminal-phase half-life averaging 95 hours. In some embodiments, administration of the dendrimer provides a terminal phase half-life ($t_{1/2}$) for unconjugated/released cabazitaxel of at least 12 hours, at least 24 hours, at least 30 hours, at least 40 hours, at least 48 hours, at least 50 hours, or at least 75 hours.

It will be appreciated that any one or more of the above pharmacokinetic properties may provide better clinical efficacy in comparison to the direct administration of the free drug. In some embodiments, administration of the dendrimer provides better efficacy of the drug, in comparison to the direct administration of an equivalent dose of the free drug. In some embodiments, the dendrimer, provides an improved efficacy property selected from the group consisting of progression free survival, time to progression, objective response rate (PR+CR), overall response rate, overall survival and duration of response, in comparison to direct administration of an equivalent dose of free cabazitaxel.

Dendrimer Synthesis

The dendrimers of the present disclosure may be prepared by any suitable method, for example by reacting a cabazitaxel-containing precursor with a dendrimeric intermediate already containing a PEG group to introduce the pharmaceutically active agent, by reacting a PEG-containing precursor with a dendrimeric intermediate already containing a cabazitaxel residue, or by reacting an intermediate comprising the residue of a lysine group, a cabazitaxel residue and a PEG group with a dendrimeric intermediate. Accordingly, in a fifth aspect there is provided a process for producing a dendrimer as defined herein, comprising:

a) reacting a cabazitaxel intermediate which is:

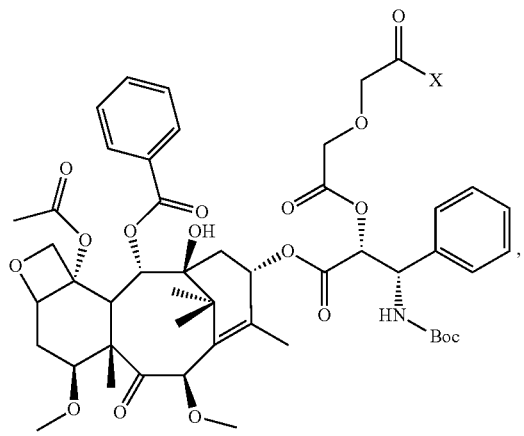

wherein X is —OH or a leaving group, or wherein X together with the C(O) group to which it is attached forms a carboxylate salt;

with a dendrimeric intermediate which comprises:
i) a core unit (C); and
ii) building units (BU), each building unit being a lysine residue or an analogue thereof;
wherein the core unit is covalently attached to two building units via amide linkages, each amide linkage being formed between a nitrogen atom present in the core unit and the carbon atom of an acyl group present in a building unit;
the dendrimer being a five generation building unit dendrimer;
wherein building units of different generations are covalently attached to one another via amide linkages formed between a nitrogen atom present in one building unit and the carbon atom of an acyl group present in another building unit;
the dendrimer further comprising:
a plurality of second terminal groups (T2) each comprising a PEG group;
wherein at least one third of the nitrogen atoms present in the outer building units are each covalently attached to a second terminal group;
and wherein at least one third of the nitrogen atoms present in the outer building units are unsubstituted and available for reaction with the first intermediate;
or a salt thereof;
under amide coupling conditions;

wherein the core unit is covalently attached to two building units via amide linkages, each amide linkage being formed between a nitrogen atom present in the core unit and the carbon atom of an acyl group present in a building unit;
the dendrimer being a five generation building unit dendrimer;
wherein building units of different generations are covalently attached to one another via amide linkages formed between a nitrogen atom present in one building unit and the carbon atom of an acyl group present in another building unit;
the dendrimer further comprising:
a plurality of first terminal groups (T1) each comprising a cabazitazel residue covalently attached to a diglycolyl linker group;
wherein at least one third of the nitrogen atoms present in the outer building units are each covalently attached to a first terminal group;
and wherein at least one third of the nitrogen atoms present in the outer building units are unsubstituted;
or a salt thereof;
under amide coupling conditions;
or
c) reacting a surface unit intermediate which is:

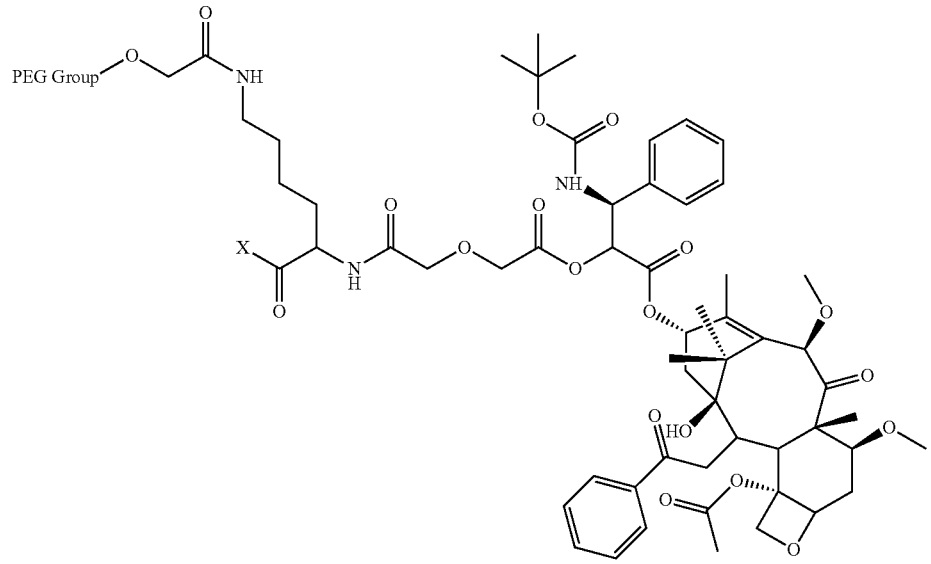

or
b) reacting a PEG intermediate which is:

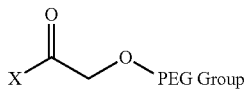

wherein PEG Group is a PEG-containing group, and X is —OH or a leaving group, or wherein X together with the C(O) group to which it is attached forms a carboxylate salt;
with a dendrimeric intermediate which comprises:
i) a core unit (C); and
ii) building units (BU), each building unit being a lysine residue or an analogue thereof;

wherein PEG Group is a PEG-containing group, and X is —OH or a leaving group, or wherein X together with the C(O) group to which it is attached forms a carboxylate salt;
with a dendrimeric intermediate comprising:
i) a core unit (C); and
ii) building units (BU), each building unit being a lysine residue or an analogue thereof;
wherein the core unit is covalently attached to two building units via amide linkages, each amide linkage being formed between a nitrogen atom present in the core unit and the carbon atom of an acyl group present in a building unit;
the dendrimeric intermediate being a four generation building unit dendrimeric intermediate;
wherein building units of different generations are covalently attached to one another via amide linkages formed between a nitrogen atom present in one building unit and the carbon atom of an acyl group present in another building unit;

and wherein nitrogen atoms present in the outer building units of the dendrimeric intermediate are unsubstituted;

or a salt thereof;

under amide coupling conditions.

Process variants a), b) and c) involve formation of amide bonds by reaction of —C(O)X groups with amine groups present in the dendrimeric intermediates. Any suitable amide formation conditions may be used. Examples of typical conditions include the use of a suitable solvent (for example dimethylformamide) optionally a suitable base, and at a suitable temperature (for example ambient temperature, e.g. in the range of from 15 to 30° C.). Where X is a leaving group, any suitable leaving group may be used, for example an activated ester. Where X is an —OH group or where X together with the C(O) group to which it is attached forms a carboxylate salt, the group will typically be converted to a suitable leaving group prior to reaction with a dendrimeric intermediate, for example by use of a suitable amide coupling reagent such as PyBOP.

Any suitable isolation and/or purification technique may be utilised, for example the dendrimer may be obtained by dissolution in a suitable solvent (e.g. THF) and precipitation by addition into an antisolvent (e.g. MTBE).

The cabazitaxel intermediate used in variant a) may itself be obtained, for example, by reaction of cabazitaxel with diglycolic anhydride, for example in the presence of a suitable solvent such as dichloromethane and a suitable base such as triethylamine.

The surface unit intermediate used in variant c) may itself be obtained, for example, by:

i) reacting a PEG intermediate which is:

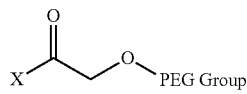

wherein PEG Group is a PEG-containing group, and
X is —OH or a leaving group, or wherein X together with the C(O) group to which it is attached forms a carboxylate salt;

with

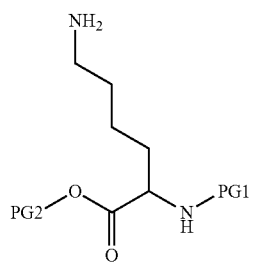

wherein PG1 is an amine protecting group (such as a Boc or Cbz group), and PG2 is an acid protecting group (such as a methyl or benzyl ester);

ii) deprotecting PG1;

iii) reacting the product of step ii) with a cabazitaxel intermediate which is:

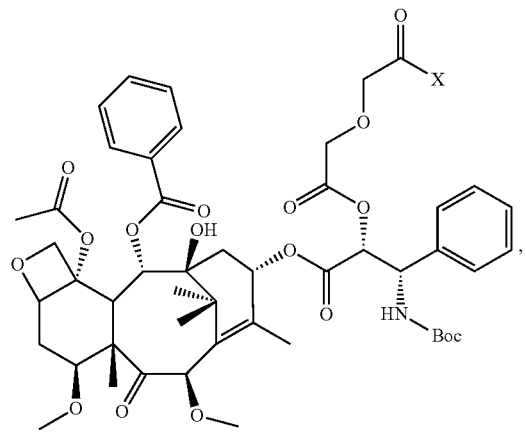

wherein X is —OH or a leaving group, or wherein X together with the C(O) group to which it is attached forms a carboxylate salt; and iv) deprotecting PG2.

The dendrimeric intermediate used in variant a) may itself be obtained by, for example, a sequential process involving:

i) reaction of a core unit (C) containing amino groups, with building units which are protected lysines or analogues thereof, which contain a —C(O)X group, wherein X is —OH or a leaving group or —CO(X) forms a carboxylate salt, and in which the amino groups present in the lysines or analogues thereof are protected, to form amide linkages between the core unit and building units;

ii) deprotecting protecting groups present on the building units;

iii) reacting free amino groups present on the building units with further building units which are protected lysines or analogues thereof, which contain a —C(O)X group, wherein X is —OH or a leaving group or —CO(X) forms a carboxylate salt, and in which the amino groups present in the lysines or analogues thereof are protected, to form amide linkages between the different generations of building units;

iv) deprotecting protecting groups present on the building units;

v) repeating steps iii) and iv) until a four generation building unit is produced;

vi) reacting free amino groups present on the building units with

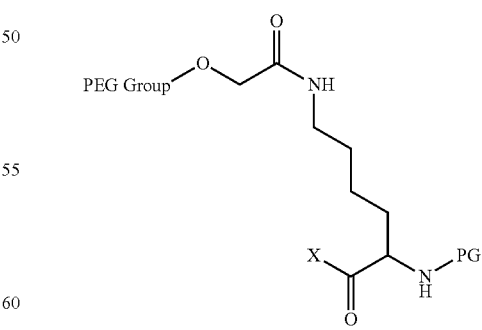

wherein PG is a protecting group, and wherein X is —OH or a leaving group, or wherein X together with the C(O) group to which it is attached forms a carboxylate salt, to form amide linkages therebetween; and vii) deprotecting the protecting groups PG.

Alternatively, the dendrimeric intermediate used in variant a) may be obtained, for example, by carrying out steps i) to v) as described above, and:

vi) reacting free amino groups present on the building units with further building units which are protected lysines or analogues thereof, which contain a —C(O)X group, wherein X is —OH or a leaving group or —CO(X) forms a carboxylate salt, and in which the amino groups present in the lysines or analogues thereof are orthogonally protected, to form amide linkages between the different generations of building units;

vii) deprotecting a first set of amino protecting groups;

viii) reacting free amino groups present on the building units with

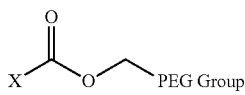

wherein PEG Group is a PEG-containing group, and X is —OH or a leaving group, or wherein X together with the C(O) group to which it is attached forms a carboxylate salt;

vii) deprotecting a second set of amino protecting groups.

The dendrimeric intermediate used in variant b) may itself be obtained, for example, by carrying out steps i) to v) as described above in relation to variant a), and:

vi) reacting free amino groups present on the building units with

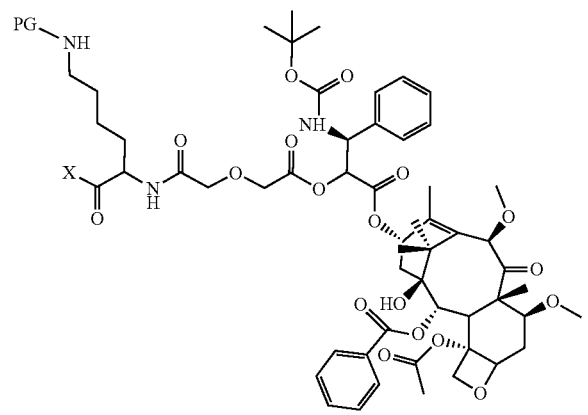

wherein PG is a protecting group, and wherein X is —OH or a leaving group, or wherein X together with the C(O) group to which it is attached forms a carboxylate salt, to form amide linkages therebetween; and vii) deprotecting the protecting groups PG.

Alternatively, the dendrimeric intermediate used in variant b) may be obtained, for example, by carrying out steps i) to v) as described above, and:

vi) reacting free amino groups present on the building units with further building units which are protected lysines or analogues thereof, which contain a —C(O)X group, wherein X is —OH or a leaving group or —CO(X) forms a carboxylate salt, and in which the amino groups present in the lysines or analogues thereof are orthogonally protected, to form amide linkages between the different generations of building units;

vii) deprotecting a first set of amino protecting groups;

viii) reacting free amino groups present on the building units with

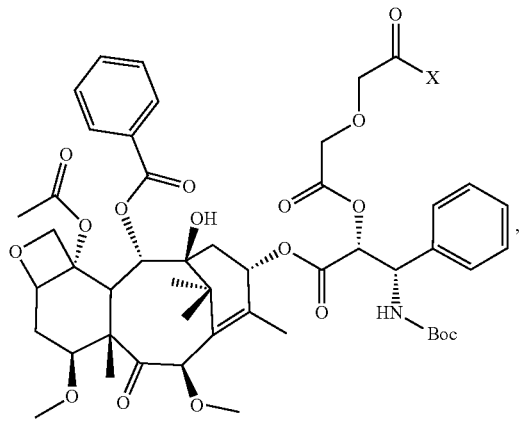

wherein X is —OH or a leaving group, or wherein X together with the C(O) group to which it is attached forms a carboxylate salt;

vii) deprotecting a second set of amino protecting groups.

The dendrimeric intermediate used in variant c) may itself be obtained, for example, by carrying out steps i) to v) as described above in relation to variant a).

The present disclosure also provides synthetic intermediates useful in producing the dendrimers. Accordingly, there is also provided an intermediate for producing a dendrimer which is

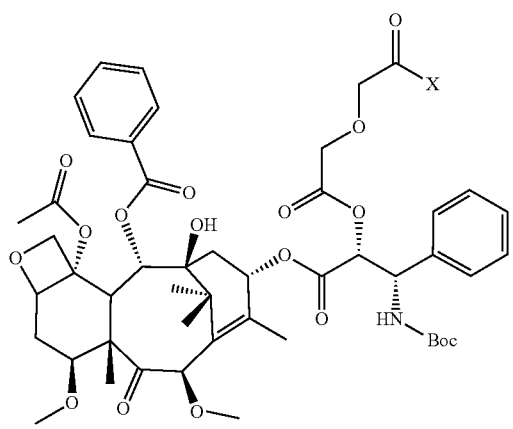

wherein X is —OH or a leaving group, or wherein X together with the C(O) group to which it is attached forms a carboxylate salt. Such an intermediate may be produced, for example, as described above.

There is also provided an intermediate for producing a dendrimer which is

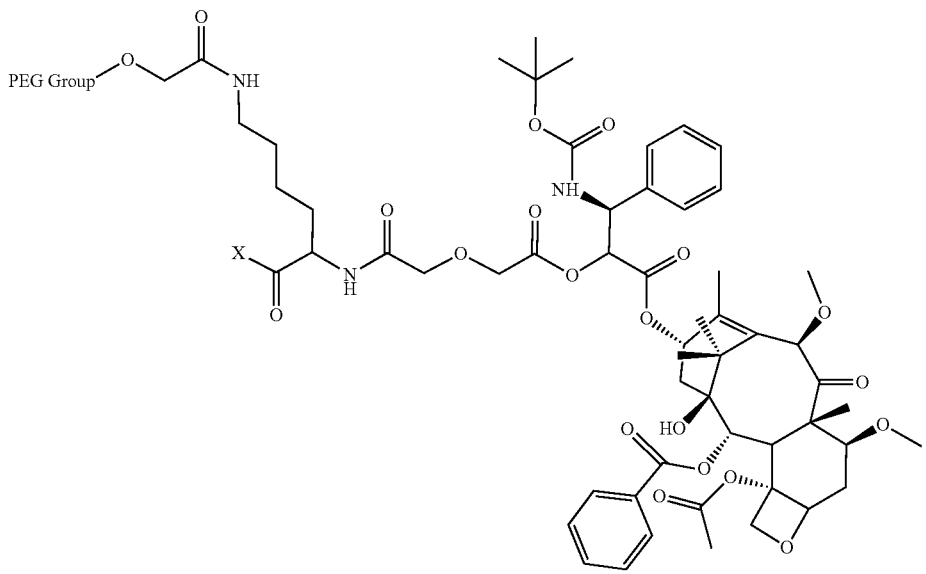

wherein PEG Group is a PEG-containing group, and X is —OH or a leaving group, or wherein X together with the C(O) group to which it is attached forms a carboxylate salt. Such an intermediate may be produced, for example, as described above.

The present disclosure will now be described with reference to the following examples which illustrate some particular aspects of the present disclosure. However, it is to be understood that the particularity of the following description of the present disclosure is not to supersede the generality of the preceding description of the present disclosure.

EXAMPLES

Example 1: Synthesis and Characterization of BHALys[Lys]$_{32}$[α-NH$_2$TFA]$_{32}$[ε-PEG~2100]$_{32}$‡

The dendrimers represented in the examples below include reference to the core and the building units in the outermost generation of the dendrimer. The subsurface generations are not depicted. The dendrimer BHALys[Lys]$_{32}$ is representative of a 5 generation dendrimer having the formula BHALys[Lys]$_2$[Lys]$_4$[Lys]$_8$[Lys]$_{16}$[Lys]$_{32}$.

32‡ relates to the theoretical number of ε surface amino groups on the dendrimer available for substitution with PEG$_{~2100}$. The actual mean number of PEG$_{~2100}$ groups attached to the BHALys[Lys]$_{32}$ was determined experimentally by $^1$H NMR (see below section in the present Example entitled Characterization of BHALys[Lys]$_{32}$[α-NH$_2$-TFA]$_{32}$ [ε-PEG$_{~2100}$]$_{32}$‡).

BHALys[Boc]$_2$

Solid α,ε-(t-Boc)$_2$-(L)-lysine p-nitrophenol ester (2.787 kg, 5.96 mol) was added to a solution of aminodiphenylmethane (benzhydrylamine) (0.99 kg, 5.4 mol) in anhydrous acetonitrile (4.0 L), DMF (1.0 L) and triethylamine (1.09 kg) over a period of 15 min. The reaction mixture was agitated at 20° C. overnight. The reaction mixture was then warmed to 35° C. and aqueous sodium hydroxide (0.5 N, 10 L) was added slowly over 30 min. The mixture was stirred for an additional 30 min then filtered. The solid cake was washed with water and dried to a constant weight (2.76 kg, 5.4 mol) in 100% yield. $^1$H NMR (CD$_3$OD) δ 7.3 (m, 10H, Ph Calc 10H); 6.2 (s, 1H, CH-Ph$_2$ Calc 1H); 4.08 (m, α-CH, 1H), 3.18 (br, ε—CH$_2$) and 2.99 (m, ε—CH$_2$ 2H); 1.7-1.2 (br, β,γ,δ-CH$_2$) and 1.43 (s, tBu) total for β,γ,δ-CH$_2$ and tBu 25H Calc 24H. MS (ESI +ve) found 534.2 [M+Na]$^+$ calc for C$_{29}$H$_{41}$N$_3$O$_5$Na [M+Na]$^+$ 534.7.

BHALys[HCl]$_2$

A solution of concentrated HCl (1.5 L) in methanol (1.5 L) was added slowly, in three portions, to a stirred suspension of BHALys[Boc]2 (780.5 g, 1.52 mol) in methanol (1.5 L) at a rate to minimize excessive frothing. The reaction mixture was stirred for an additional 30 min, then concentrated under vacuum at 35° C. The residue was taken up in water (3.4 L) and concentrated under vacuum at 35° C. twice, then stored under vacuum overnight. Acetonitrile (3.4 L) was then added and the residue was again concentrated under vacuum at 35° C. to give BHALys[HCl]$_2$ as a white solid (586 g, 1.52 mol) in 100% yield. $^1$H NMR (D$_2$O) δ 7.23 (br m, 10H, Ph Calc 10H); 5.99 (s, 1H, CH-Ph$_2$ Calc 1H); 3.92 (t, J=6.5 Hz, α-CH, 1H, Calc 1H); 2.71 (t, J=7.8 Hz, δ-CH$_2$, 2H, Calc 2H); 1.78 (m, β,γ,δ-CH$_2$, 2H), 1.47 (m, β,γ,δ-CH$_2$, 2H), and 1.17 (m, β,γ,δ-CH$_2$, 2H, total 6H Calc 6H). MS (ESI +ve) found 312 [M+H]$^+$ calc for C$_{19}$H$_{26}$N$_3$O [M+H]$^+$ 312.

BHALys[Lys]$_2$[Boc]$_4$

To a suspension of BHALys[HCl]$_2$ (586 g, 1.52 mmol) in anhydrous DMF (3.8 L) was added triethylamine (1.08 kg) slowly to maintain the reaction temperature below 30° C. Solid α,ε-(t-Boc)$_2$-(L)-lysine p-nitrophenol ester (1.49 kg) was added in three portions, slowly and with stirring for 2 hours between additions. The reaction was allowed to stir overnight. An aqueous solution of sodium hydroxide (0.5 M, 17 L) was added slowly to the well stirred mixture, and stirring was maintained until the solid precipitate was freely moving. The precipitate was collected by filtration, and the solid cake was washed well with water (2×4 L) then acetone/water (1:4, 2×4 L). The solid was slurried again with water then filtered and dried under vacuum overnight to give BHALys [Lys]$_2$[Boc]$_4$ (1.51 kg) in 100% yield. $^1$H NMR (CD$_3$OD) δ 7.3 (m, 10H, Ph Calc 10H); 6.2 (s, 1H, CH-Ph$_2$ Calc 1H); 4.21 (m, α-CH), 4.02 (m, α-CH) and 3.93 (m, α-CH, total 3H, Calc 3H); 3.15 (m, ε—CH$_2$) and 3.00 (m, δ-CH$_2$ total 6H, Calc 6H); 1.7-1.3 (br, β,γ,δ-CH$_2$) and 1.43

(s, tBu) total for β,γ,δ-CH$_2$ and tBu 57H, Calc 54H. MS (ESI +ve) found 868.6 [M-Boc]$^+$; 990.7 [M+Na]$^+$ calc for C$_{51}$H$_{81}$N$_7$O$_{11}$Na [M+Na]$^+$ 991.1.

BHALys[Lys]$_2$[HCl]$_4$

BHALys[Lys]$_2$[Boc]$_4$ (1.41 kg, 1.46 mol) was suspended in methanol (1.7 L) with agitation at 35° C. Hydrochloric acid (1.7 L) was mixed with methanol (1.7 L), and the resulting solution was added in four portions to the dendrimer suspension and left to stir for 30 min. The solvent was removed under reduced pressure and worked up with two successive water (3.5 L) strips followed by two successive acetonitrile (4 L) strips to give BHALys[Lys]$_2$[HCl]$_4$ (1.05 Kg, 1.46 mmol) in 102% yield. $^1$H NMR (D$_2$O) δ 7.4 (br m, 10H, Ph Calc 10H); 6.14 (s, 1H, CH-Ph$_2$ Calc 1H); 4.47 (t, J=7.5 Hz, α-CH, 1H), 4.04 (t, J=6.5 Hz, α-CH, 1H), 3.91 (t, J=6.8 Hz, α-CH, 1H, total 3H, Calc 3H); 3.21 (t, J=7.4 Hz, ε—CH$_2$, 2H), 3.01 (t, J=7.8 Hz, ε—CH$_2$, 2H) and 2.74 (t, J=7.8 Hz, ε—CH$_2$, 2H, total 6H, Calc 6H); 1.88 (m, β,γ,δ-CH$_2$), 1.71 (m, β,γ,δ-CH$_2$), 1.57 (m, β,γ,δ-CH$_2$) and 1.35 (m, β,γ,δ-CH$_2$ total 19H, Calc 18H).

BHALys[Lys]$_4$[Boc]$_8$

BHALys[Lys]$_2$[HCl]$_4$ (1.05 Kg, 1.47 mol) was dissolved in DMF (5.6 L) and triethylamine (2.19 L). The α,ε-(t-Boc)$_2$-(L)-lysine p-nitrophenol ester (2.35 kg, 5.03 mol) was added in three portions and the reaction stirred overnight at 25° C. A NaOH (0.5M, 22 L) solution was added and the resulting mixture filtered, washed with water (42 L) and then air dried. The solid was dried under vacuum at 45° C. to give BHALys [Lys]$_4$[Boc]$_8$ (2.09 kg, 1.11 mol) in 76% yield. $^1$H NMR (CD$_3$OD) δ 7.3 (m, 10H, Ph Calc 10H); 6.2 (s, 1H, CH-Ph$_2$ Calc 1H); 4.43 (m, α-CH), 4.34 (m, α-CH), 4.25 (m, α-CH) and 3.98 (br, α-CH, total 7H, Calc 7H); 3.15 (br, ε—CH$_2$) and 3.02 (br, ε—CH$_2$ total 14H, Calc 14H); 1.9-1.2 (br, β,γ,δ-CH$_2$) and 1.44 (br s, tBu) total for β,γ,δ-CH$_2$ and tBu 122H, Calc 144H.

BHALys[Lys]$_4$[TFA]$_8$

To a stirred suspension of BHALys[Lys]$_4$[Boc]8 (4 g, 2.13 mmol) in DCM (18 mL) was added TFA (13 mL) at 0° C. The solids dissolved, and the solution was stirred overnight under an atmosphere of argon. The solvents were removed under vacuum, and residual TFA was removed by trituration with diethyl ether (100 mL). The product was re-dissolved in water then freeze dried to give BHALys[Lys]$_4$[TFA]$_8$ as an off-white solid (4.27 g, 2.14 mmol) in 101% yield. $^1$H NMR (D$_2$O) δ 7.21 (br m, 10H, Ph Calc 10H); 5.91 (s, 1H, CH-Ph$_2$ Calc 1H); 4.17 (t, J=7.4 Hz, α-CH, 1H), 4.09 (t, J=7.1 Hz, α-CH, 1H), 4.02 (t, J=7.2 Hz, α-CH, 1H, 3.84 (t, J=6.5 Hz, α-CH, 2H), 3.73 (t, J=6.7 Hz, α-CH, 1H), 3.67 (t, J=6.7 Hz, α-CH, 1H, total 7H, Calc 7H); 3.0 (m, ε—CH$_2$), 2.93 (m, ε—CH$_2$) and 2.79 (b, ε—CH$_2$, total 15H, Calc 14H); 1.7 (br, β,γ,ε—CH$_2$), 1.5 (br, β,γ,δ-CH$_2$), 1.57 (m, β,γ,δ-CH$_2$) and 1.25 (br, β,γ,δ-CH$_2$ total 45H, Calc 42H). MS (ESI +ve) found 541.4 [M+2H]$^{2+}$; calc for C$_{55}$H$_{99}$N$_{15}$O$_7$ [M+2H]$^{2+}$ 541.2.

BHALys[Lys]$_8$[Boc]$_{16}$

A solution of α,ε-(t-Boc)$_2$-(L)-lysine p-nitrophenol ester (1.89 g, 4.05 mmol) in DMF (25 mL) was added to a solution of BHALys [Lys]$_4$[NH$_2$TFA]$_8$ (644 mg, 0.32 mmol) and triethylamine (0.72 mL, 5.2 mmol) in DMF (25 mL) and the reaction was left to stir overnight under an argon atmosphere. The reaction mixture was poured onto ice/water (500 mL) then filtered and the collected solid was dried overnight under vacuum. The dried solid was washed thoroughly with acetonitrile to give BHALys[Lys]$_8$[Boc]$_{16}$ as an off white solid (0.82 g, 0.22 mmol) in 68% yield. $^1$H NMR (CD$_3$OD) δ 7.3 (m, 10H, Ph Calc 10H); 6.2 (br s, 1H, CH-Ph$_2$ Calc 1H); 4.48 (br, α-CH), 4.30 (br, α-CH) and 4.05 (br, α-CH, total 16H Calc 15H); 3.18 (br, ε—CH$_2$) and 3.02 (m, ε—CH$_2$ total 31H, Calc 30H); 1.9-1.4 (br, β,γ,δ-CH$_2$) and 1.47 (br s, tBu) total for β,γ,δ-CH$_2$ and tBu 240H, Calc 234H. MS (ESI+ve) found 3509 [M+H-(Boc)$_2$]$^+$ calc for C$_{173}$H$_{306}$N$_{31}$O$_{43}$ [M+H-(Boc)$_2$]$^+$ 3508.5; 3408 [M+H-(Boc)$_3$]$^+$ calc for C$_{168}$H$_{298}$N$_{31}$O$_{41}$ [M+H-(Boc)$_3$]$^+$ 3408.4.

BHALys[Lys]$_8$[TFA]$_{16}$

A solution of TFA/DCM (1:1, 19 mL) was added slowly to a stirred suspension of BHALys[Lys]$_8$[Boc]$_{16}$ (800 mg, 0.22 mmol) in DCM (25 mL). The solids dissolved, and the solution was stirred overnight under an atmosphere of argon. The solvents were removed under vacuum, and residual TFA was removed by repetitive freeze drying of the residue, to give BHALys [Lys]$_8$[TFA]$_{16}$ as an off-white lyophylisate (848 mg, 0.22 mmol) in 100% yield. $^1$H NMR (D$_2$O) δ 7.3 (br m, 10H, Ph Calc 10H); 6.08 (s, 1H, CH-Ph$_2$ Calc 1H); 4.3 (m, α-CH), 4.18 (m, α-CH), 4.0 (m, α-CH) and 3.89 (m, α-CH, total 16H, Calc 15H); 3.18 (br, ε—CH$_2$) and 2.94 (m, ε—CH$_2$ total 32H, Calc 30H); 1.9 (m, β,γ,δ-CH$_2$), 1.68 (m, β,γ,δ-CH$_2$) and 1.4 (m, β,γ,δ-CH$_2$ total 99H, Calc 90H). MS (ESI +ve) found 2106 [M+H]$^+$ calc for C$_{103}$H$_{194}$N$_{31}$O$_{15}$ [M+H]$^+$ 2106.9.

BHALys[Lys]$_{16}$[Boc]$_{32}$

A solution of α,ε-(t-Boc)$_2$-(L)-lysine p-nitrophenol ester (1.89 g, 4.05 mmol) in DMF (25 mL) was added to a solution of BHALys [Lys]$_8$[TFA]$_{16}$ (644 mg, 0.32 mmol) and triethylamine (0.72 mL, 5.2 mmol) in DMF (25 mL) and the reaction was left to stir overnight under an argon atmosphere. The reaction was poured onto ice/water (500 mL) then filtered and the collected solid was dried overnight under vacuum. The dried solid was washed thoroughly with acetonitrile to give BHALys[Lys]$_{16}$[Boc]$_{32}$ as an off white solid (0.82 g, 0.22 mmol) in 68% yield. $^1$H NMR (CD$_3$OD) δ 7.28 (m, 9H, Ph Calc 10H); 6.2 (br s, 1H, CH-Ph$_2$ Calc 1H); 4.53 (br, α-CH), 4.32 (br, α-CH) and 4.05 (br, α-CH, total 35H, Calc 31H); 3.18 (br, ε—CH$_2$) and 3.04 (m, ε—CH$_2$ total 67H, Calc 62H); 1.9-1.5 (br, β,γ,δ-CH$_2$) and 1.47 (br s, tBu) total for β,γ,δ-CH$_2$ and tBu 474H Calc, 474H. MS (ESI+ve) found 6963 [M+H-(Boc)$_4$]$^+$ calc for C$_{339}$H$_{610}$N$_{63}$O$_{87}$ [M+H-(Boc)$_4$]$^+$ 6960.9; 6862 [M+H-(Boc)$_5$]$^+$ calc for C$_{334}$H$_{604}$N$_{63}$O$_{85}$ [M+H-(Boc)$_5$]$^+$ 6860.8.

BHALys[Lys]$_{16}$[TFA]$_{32}$

A solution of TFA/DCM (1:1, 19 mL) was added slowly to a stirred suspension of BHALys[Lys]$_{16}$[Boc]$_{32}$ (800 mg, 0.11 mmol) in DCM (25 mL). The solids dissolved, and the solution was stirred overnight under an atmosphere of argon. The solvents were removed under vacuum, and residual TFA was removed by repetitive freeze drying of the residue, to give BHALys[Lys]$_{16}$[TFA]$_{32}$ as an off-white lyophylate (847 mg, 0.11 mmol) in 100% yield. $^1$H NMR (D$_2$O) δ 7.3 (br m, 11H, Ph Calc 10H); 6.06 (s, 1H, CH-Ph$_2$ Calc 1H); 4.3 (m, α-CH), 4.19 (m, α-CH), 4.0 (m, α-CH) and 3.88 (m, α-CH, total 35H, Calc 31H); 3.15 (br, ε—CH$_2$) and 2.98 (m, ε—CH$_2$ total 69H, Calc 62H); 1.88 (m, β,γ,δ-CH$_2$), 1.7 (m, β,γ,δ-CH$_2$) and 1.42 (m, β,γ,δ-CH$_2$ total 215H, Calc 186H). MS (ESI+ve) found 4158 [M+H]$^+$ calc for C$_{199}$H$_{386}$N$_{63}$O$_{31}$ [M+H]$^+$ 4157.6.

HO-Lys(α-BOC)(ε-PEG$_{\sim2100}$)

DIPEA (0.37 mL, 2.10 mmol) was added to an ice-cooled mixture of NHS-PEG$_{\sim2100}$ (2.29 g, 1.05 mmol) (in which PEG$_{\sim2100}$ represents a methoxy-terminated PEG group having approximate average molecular weight of 2100 Da, and in which NHS represents NHS—C(O)CH$_2$), and N-α-t-BOC-L-lysine (0.26 g, 1.05 mmol) in DMF (20 mL). The stirred mixture was allowed to warm to room temperature overnight then any remaining solids were filtered (0.45 μm PALL acrodisc) before removing the solvent in vacuo. The residue was taken up in ACN/H$_2$O (1:3, 54 mL) and purified by PREP HPLC (Waters)(Bridge C18, 5 µm, 19×150 mm, 25 to 32% ACN (5-15 min), 32 to 60% ACN (15 to 20 min), no buffer, 8 mL/min, RT=17 min), providing 1.41 g (56%) of HO-Lys(BOC)(PEG$_{2100}$). $^1$H NMR (CD$_3$OD) δ 3.96-4.09 (m, 1H), 3.34-3.87 (m, 188H); 3.32 (s, 3H), 3.15 (q, J=6.0 Hz, 2H), 2.40 (t, J=6.2 Hz, 2H), 1.28-1.88 (m, 6H), 1.41 (s, 9H).

BHALys[Lys]$_{32}$[λ-BOC]$_{32}$[ε-PEG$_{~2100}$]$_{32‡}$

To a stirred mixture of BHALys[Lys]$_{16}$[TFA]$_{32}$ (0.19 g, 24 µmol) in DMF (20 mL) was added DIPEA (0.86 mL, 4.86 mmol). This mixture was then added dropwise to a stirred mixture of PyBOP (0.62 g, 1.20 mmol) and Lys(BOC)(PEG$_{~2100}$) (2.94 g, 1.20 mmol) in DMF (20 mL) at room temperature. The reaction mixture was left to stir overnight, then diluted with water (200 mL). The aqueous mixture was subjected to a centramate filtration (5 k membrane, 20 L water). The retentate was freeze dried, providing 1.27 g (73%) of desired dendrimer. HPLC (C8 XBridge, 3×100 mm, gradient: 5% ACN (0-1 min), 5-80% ACN/H2O) (1-7 min), 80% ACN (7-12 min), 80-5% ACN (12-13 min), 5% ACN (13-15 min), 214 nm, 0.1% TFA) Rf (min)=8.52. 1H NMR (300 MHz, D$_2$O) δ (ppm): 1.10-2.10 (m, Lys CH$_2$ (β, χ, δ) and BOC, 666H), 3.02-3.36 (m, Lys CH$_2$ (ε), 110H), 3.40 (s, PEG-OMe, 98H), 3.40-4.20 (m, PEG-OCH$_2$, 5750H+Lys CH surface, 32H), 4.20-4.50 (m, Lys, CH internal 32H), 7.20-7.54 (m, BHA, 8H). $^1$H NMR indicates approximately 29 PEGs.

BHALys[Lys]$_{32}$[α-NH$_2$TFA]$_{32}$[ε-PEG$_{~2100}$]$_{32‡}$ 1.27 g (17.4 µmol) of BHALys[Lys]$_{32}$[α-BOC]$_{32}$[ε-PEG$_{~2100}$]$_{32}$ was stirred in TFA/DCM (1:1, 20 mL) at room temperature overnight. The volatiles were removed in vacuo, then the residue was taken up in water (30 mL). The mixture was then concentrated. This process was repeated two more times before being freeze dried, providing 1.35 g (106%) of desired product as a viscous colourless oil. HPLC (C8 XBridge, 3×100 mm, gradient: 5% ACN (0-1 min), 5-80% ACN/H$_2$O) (1-7 min), 80% ACN (7-12 min), 80-5% ACN (12-13 min), 5% ACN (13-15 min), 214 nm, 0.1% TFA) Rf (min)=8.51. $^1$H-nmr (300 MHz, D$_2$O) δ (ppm): 1.22-2.08 (Lys CH$_2$ ((β, χ, δ), 378H), 3.00-3.26 (Lys CH2 (ε), 129H), 3.40 (PEG-OMe, 96H), 3.45-4.18 (PEG-OCH$_2$, 5610H+Lys CH surface, 32H), 4.20-4.46 (Lys, CH internal, 33H), 7.24-7.48 (8H, BHA). $^1$H NMR indicates approximately 29 PEGs.

Characterization of BHALys[Lys]$_{32}$[α-NH$_2$TFA]$_{32}$[ε-PEG$_{~2100}$]$_{32‡}$ Table 1 illustrates the various batches of BHALys[Lys]32[α-NH$_2$TFA]$_{32}$[ε-PEG$_{~2100}$]$_{32\#}$ synthesised. The actual number of PEG chains on the dendrimer is also calculated by $^1$H NMR.

TABLE 1

Various Batches of BHALys[Lys]$_{32}$[α-NH$_2$TFA]$_{32}$[ε-PEG$_{~2100}$]$_{32‡}$

| Batch | Scale | PEG length from CoA (Da) | Number of PEGs (x) on BHALys[Lys]$_{32}$[α-NH$_2$•TFA]$_{32}$[ε-PEG$_{~2100}$]$_x$ (from proton NMR*) | Estimated MW** (kDa) |
|---|---|---|---|---|
| 1 | 101 mg | 2200 | 29 | 75.7 |
| 2 | 98 mg | 2200 | 29 | 75.7 |
| 3 | 74.8 g | 2100 | 29 | 72.8 |
| 4 | 137 mg | 2200 | 29 | 75.7 |
| 5 | 1.19 g | 2100 | 31 | 77.0 |
| 6 | 18.98 g | 2100 | 29 | 72.8 |

*Number of PEGs is calculated from the proton NMR. For batch 1:

No. of PEGs = Number (integration) of protons in PEG region of

NMR (3.4-4.2 ppm)/Average (mean) number of protons per PEG chain (CoA PEG/44 Da × 4 H)

= 5706 H/(220/44 × 4)

= 28.53 (approx. 29 PEG units)

**Molecular Weight estimated by adding MW of various components.

For batch 1:

Total MW = Mw of dendrimer + Mw of TFA + Mw of PEG

= BHALys [Lys]$_{32}$ + 32(TFA) + 29(PEG)

= 8,258 + 3,648 + 63800

= ~75.7 kDa

TABLE 2

$^1$H NMR Data for Various Batches of BHALys[Lys]$_{32}$[α-NH$_2$TFA]$_{32}$[ε-PEG$_{~2100}$]$_{32‡}$

| Batch | Scale | $^1$H NMR of BHALys[Lys]$_{32}$[α-NH$_2$•TFA]$_{32}$[ε-PEG$_{~2100}$]$_x$ |
|---|---|---|
| 1 | 101 mg | 1.22-2.08 (Lys CH$_2$(β, χ, δ), 378H), 3.00-3.26 (Lys CH$_2$ (α), 129H), 3.40 (PEG-OMe, 96H), 3.45-4.18 (PEG-OCH$_2$, 5610H + Lys CH surface, 32H), 4.20-4.46 (Lys, CH internal, 33H), 7.24-7.48 (8H, BHA). |
| 2 | 98 mg | As for batch 1 |
| 3 | 74.8 g | 1.02-2.18 (Lys CH$_2$(β, χ, δ), 378H), 2.94-3.36 (Lys CH$_2$ (α), 129H), 3.41 (PEG-OMe, 93H), 3.45-4.18 (PEG-OCH$_2$, 5432H + Lys CH surface, 32H), 4.18-4.50 (Lys, CH internal, 32H), 7.12-7.64 (9H, BHA). |
| 4 | 137 mg | As for batch 1 |
| 5 | 1.19 g | 1.02-2.16 (Lys CH$_2$(β, χ, δ), 378H), 2.93-3.36 (Lys CH$_2$ (α), 129H), 3.41 (PEG-OMe, 101H), 3.45-4.18 (PEG-OCH$_2$, 5908H + Lys CH surface, 32H), 4.18-4.50 (Lys, CH internal, 33H), 7.21-7.54 (9H, BHA). |
| 6 | 18.98 g | As for batch 3 |

Example 2: Synthesis of Linker-Cabazitaxel, Wherein the Linker is Diglycolic Acid (DGA) [DGA-Cabazitaxel]

To a solution of Cabazitaxel (2.00 g, 2.39 mmol) in dichloromethane (30 mL, 15 vol.) was added diglycolic anhydride (320.70 mg, 2.62 mmol, 1.1 eq., 95% purity). After stirring for 5 min., triethylamine (500 µL, 3.59 mmol, 1.5 eq.) was added. The reaction mixture was stirred at room temperature for 1.5 h. LC-MS analysis (eluent: 40-80% acetonitrile in water with 0.1% 10 mM ammonium formate buffer) showed presence of less than 1% starting material. The reaction mixture was diluted with 30 mL of DCM and then washed twice with sodium chloride (5%) and sodium phosphate (1%) buffer at pH=3 (30 mL). During the first wash, the pH rose to 6.0, 1M aq. HCl (2.0 mL) was added to readjust the pH at 3.0. Layers separated. DCM extract was dried over MgSO4 (3.2 g) and filtered through glass sintered funnel. Funnel washed two times with 5 mL (10 mL) DCM. The filtrate was evaporated to give white solid. Yield=2.03 g, 88.5%. $^1$H NMR: DMSO-d$_6$. δ (ppm): 0.97 (s, 3H), 0.99 (s, 3H), 1.38 (s, 9H), 1.46-1.60 (m, 5H), 1.77-1.85 (m, 4H), 2.23 (s, 3H), 2.62-2.75 (m, 1H), 3.22 (s, 3H), 3.29 (s, 3H), 3.59 (d, J=6 Hz, 1H), 3.76 (dd, J=6 Hz and 12 Hz, 1H), 4.02 (s, 2H), 4.14 (s, 2H), 4.31 (d, J=18 Hz, 1H), 4.40 (d, J=15 Hz, 1H), 4.51 (s, 1H), 4.71 (s, 1H), 4.96 (d, J=9 Hz, 1H), 5.06 (t, J=9 Hz, 1H), 5.17 (d, J=6 Hz, 1H), 5.38 (d, J=9 Hz, 1H), 5.82 (t, J=9 Hz, 1H), 7.19 (t, J=9 Hz, 1H), 7.35-7.46 (m, 4H), 7.64-7.77 (m, 3H), 7.88 (d, J=9 Hz, 1H), 7.98 (d, J=6 Hz, 2H). LC-MS: C8) (Bridge 3.0×100 mm, 120 A, 3.5 μm. 40-80% ACN/H$_2$O (1-7 min), 80% ACN (7-9 min), 80-40% ACN (9-11 min), 40% ACN (11-15 min), 0.1% 10 mM ammonium formate Rf (min)=5.76. ESI (+ve) observed [M+OH]$^+$=969. Calculated for $C_{49}H_{61}NO_{18}$=952.02 Da. In process analysis: 25 μl aliquot was diluted with 1 ml acetonitrile. Isolated material: Approximately 1.0 mg/ml solution in acetonitrile.

Example 3: Synthesis of BHALys[Lys]$_{32}$[α-DGA-Cabazitaxel]$_{32‡}$[ε-PEG$_{~2100}$]$_{32‡}$ (SPL9048)

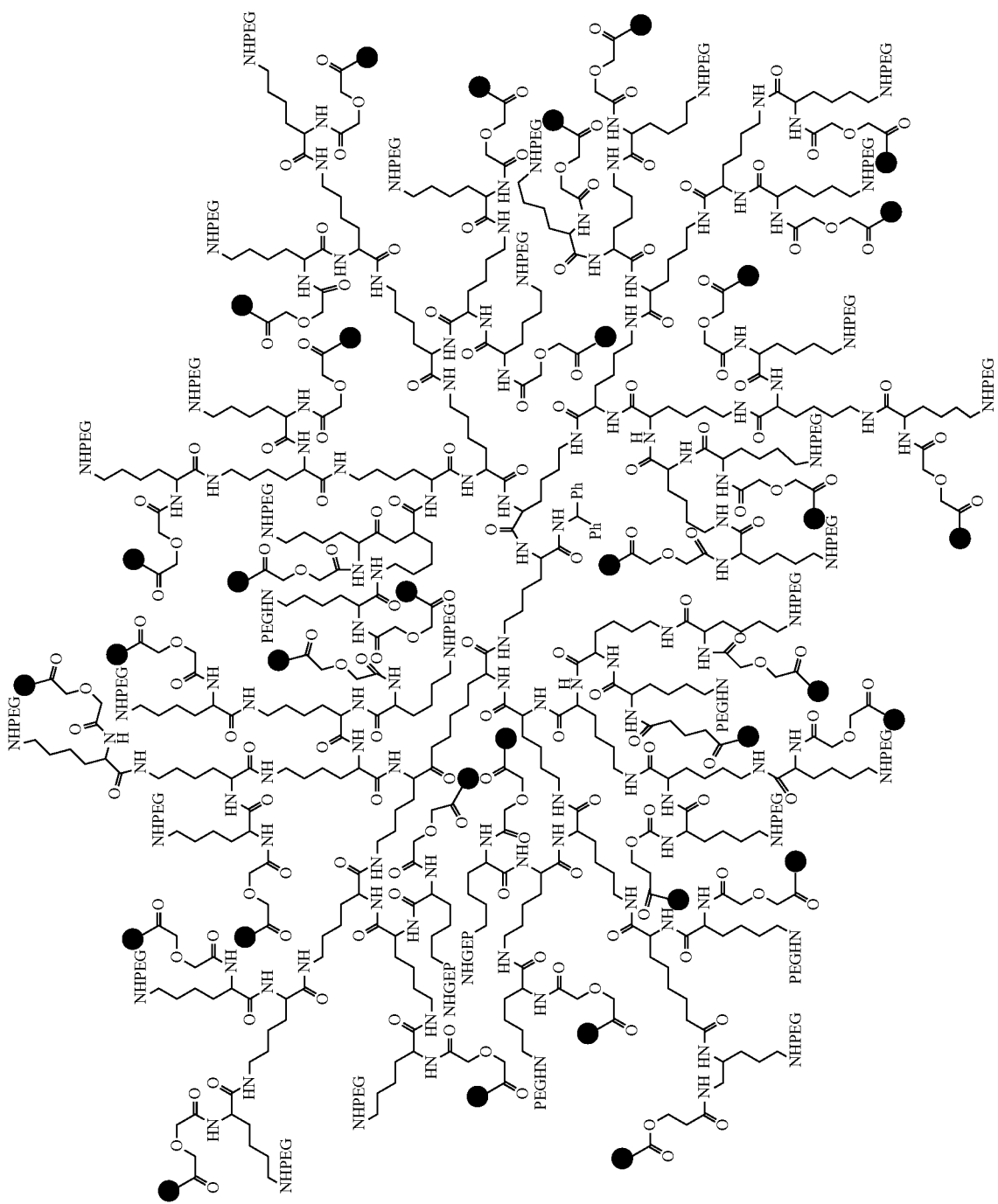

PEG represents —C(O)CH$_2$-PEG$_{\sim2100}$ in which PEG$_{\sim2100}$ represents a methoxy-terminated PEG group having approximate average molecular weight of 2100 Daltons (e.g. an average molecular weight in the range of about 1900 to 2300); and represents a residue of Cabazitaxel.

Note: 32† relates to the theoretical number of a surface amino groups on the dendrimer available for substitution with DGA-Cabazitaxel. The actual mean number of DGA-Cabazitaxel groups attached to BHALys[Lys]$_{32}$ was determined experimentally by $^1$H NMR using 3,4,5-Trichloro pyridine as an internal standard.

To a solution of DGA-Cabazitaxel (2.020 g, 2.12 mmol, 1.2 eq/NH$_2$) in DMF (20 mL, 4.8 Vol.) was added solid PyBOP (1.15 g, 2.21 mmol, 1.25 eq/NH$_2$). After 5 min stirring at rt, solid BHALys[Lys]$_{32}$[α-NH$_2$TFA]$_{32}$[ε-PEG$_{\sim2100}$]$_{32‡}$ (4.19 g, 55.25 μmol) was added. DMF (3 mL) was used to rinse residual solids from vials. Suspension was stirred at RT and mixture became homogeneous within 15 min. NMM (0.97 mL, 8.84 mmol, 5 eq/NH$_2$) was added. A pale yellow solution formed, and was stirred at rt for 24 h. The solution was diluted with ACN (24 mL) and filtered through 0.45 μm filter. BHALys[Lys]$_{32}$[α-DGA-Cabazitaxel]$_{32†}$[ε-PEG$_{\sim2100}$]$_{32‡}$ was isolated by Ultrafiltration in acetonitrile (15 Diafiltration volumes) using a 0.1 m$^2$10 kda Pelicon 3 regenerated cellulose membrane. Retentate solution was concentrated in vacuo to give a yellow gum which was dissolved in THF (60 mL) and was filtered through 0.45 μm filter. The filtrate was concentrated in vacuo to obtain a gum. The yellow gum was dissolved in THF (27.5 ml, 4.9 vol based off theoretical yield of 5.6 g BHALys[Lys]$_{32}$[α-DGA-Cabazitaxel]$_{32†}$[ε-PEG$_{\sim2100}$]$_{32‡}$) and was added via dropping funnel over 1 h to vigorously stirred MTBE (110 mL, 20 vol), cooled in an ice bath and under N$_2$. A fine white suspension formed with some clumps and some material stuck to flask walls. Once addition was complete, the suspension was stirred on ice for a further 60 min. The flask was then removed from the ice bath and allowed to warm to rt with stirring. Solids on flask walls were mostly dislodged using a spatula and the solid was collected by filtration over a P3 sintered funnel. Clumps were broken using a metal spatula and the filtered solid was washed with MTBE (2×28 mL). The wet cake was transferred to a vial and residual MTBE removed under vacuum at room temperature to afford a fine white powder; 5.35 g, 94.9%. $^1$H NMR: CD$_3$OD-d$_4$. δ (ppm): 1.13-2.73 (m, 1225H), 3.23-3.30 (m, 57H), 3.37 (s, 99H), 3.39-3.97 (m, 5720H), 4.04-4.50 (m, 114H), 5.003 (br s, 27H), 5.39-5.6.15 (m, 108H), 7.28-8.10 (m, 334H). 3,4,5-Trichloro pyridine was used as internal standard and loading was calculated by comparing Cabazitaxel aromatic signals with 3,4,5-trichloropyridine signals. Theoretical molecular weight of conjugate: 102 kDa. $^1$H NMR suggests 29.8 CTX/dendrimer. Actual molecular weight is approximately 100 kDa (24.9% CTX by weight). In more than 10 batches manufactured, Cabazitaxel loading ranged from 24.2% to 26%. HPLC (C8 Phenomenex Kinetex 2.1×75 mm, 100 A, 2.6 μm. 5-45-90% ACN (with 0.1% TFA) in water (with 0.1% TFA) gradient: 5% (0-1 min), 5-45% ACN/H2O (1-2 min), 45% ACN (2-10 min), 45-90% (10-14 min), 90% (14-18 min), 90-5% ACN (18-18.1 min), 5% ACN (18.1-20 min) Rf (min)=14.03. In process analysis: 5 μL aliquot was diluted with 1 mL acetonitrile. Isolated material: Approximately 3.0 mg/ml solution in acetonitrile.

Example 4: Efficacy of Dendrimer Compounds in SCID Mice

Example 4 compares the efficacy of dendrimer compounds in SCID mice.

In the following Experiments and Figures:

SPL9005 is BHALys[Lys]$_{32}$[α-TDA-Cabazitaxel]$_{32†}$[Σ-PEG$_{\sim2100}$]$_{32‡}$; and SPL9048 is BHALys[Lys]$_{32}$[α-DGA-Cabazitaxel]$_{32†}$[ε-PEG$_{\sim2100}$]$_{32‡}$.

SPL9005 differs from SPL9048 in that it contains TDA (thiodiglycolyl) linking groups in place of diglycolyl linking groups (i.e. —S— in place of —O— present in the diglycolyl linker). SPL9005 was prepared by analogous synthetic methods to those used for the preparation of SPL 9048.

References to amounts dosed in mg/kg for the dendrimeric compounds are to the amounts of Cabazitaxel that may theoretically be released by the dendrimers.

DU145 Mouse Xenograft Prostate Cancer Model Study

A DU145 mouse xenograft prostate cancer model study was carried out to assess the anti-tumour efficacy properties of SPL9048 versus comparator compounds. The comparator compounds were free Cabazitaxel (JEVTANA® brand cabazitaxel) and SPL9005 (BHALys[Lys]$_{32}$[α-TDA-Cabazitaxel]$_{32†}$[Σ-PEG$_{\sim2100}$]$_{32‡}$).

Dendrimer compounds were pre-weighed in glass vials and stored at 20° C. until use, and dissolved in saline immediately prior to dosing. Cabazitaxel was prepared fresh for each dosing day. An aliquot of Cabazitaxel concentrate was removed under aseptic conditions and mixed with a 13% ethanol diluent to make up a 10 mg/ml working stock solution. Dosing solutions at 4.5 and 5.5 mg/mL were prepared from this working stock immediately prior to injection.

Male SCID mice (age 7-8) weeks were inoculated subcutaneously in the flank with 3×10$^6$ DU145 cells in PBS: Matrigel (1:1). Mice were weighed and tumours measured 2-3 times weekly using electronic callipers. Tumour volume (mm$^3$) was calculated as length (mm)/2× width (mm)$^2$. On day 24 after implantation (referred to as Day 1), mice with similar sized tumours (mean tumour volume 105 mm$^3$) were randomised into 5 groups of 10 animals. Treatment groups were saline, Cabazitaxel (9 and 11 mg/kg), SPL-9048 (9 mg/kg) and SPL-9005 (25 mg/kg). Test compounds were given intravenously by tail vein injection on Days 1, 8 and 15 at 0.1 ml/10 g body weight. Cabazitaxel was given at 0.05 ml/10 g body weight. Mice received a small dish containing a food supplement (mixed with food dust) daily. The experiment was ended on Day 126, or earlier if an ethical endpoint was met. Survival curves were analysed using the Mantel Cox log rank test.

FIG. 1 shows the antitumour efficacy of the treatments against DU145 tumour xenografts. Tumour volumes were determined 2-3 times weekly and are expressed as mean tumour volume (±SEM). Each group initially consisted of 10 mice and graphs are shown until no fewer than 6 animals remained in a group. As shown in FIG. 1, at the dosage administered SPL9048 induced complete tumour regression with no regrowth observed in any of the animals on Day 126 when the experiment was concluded.

Figure 2:
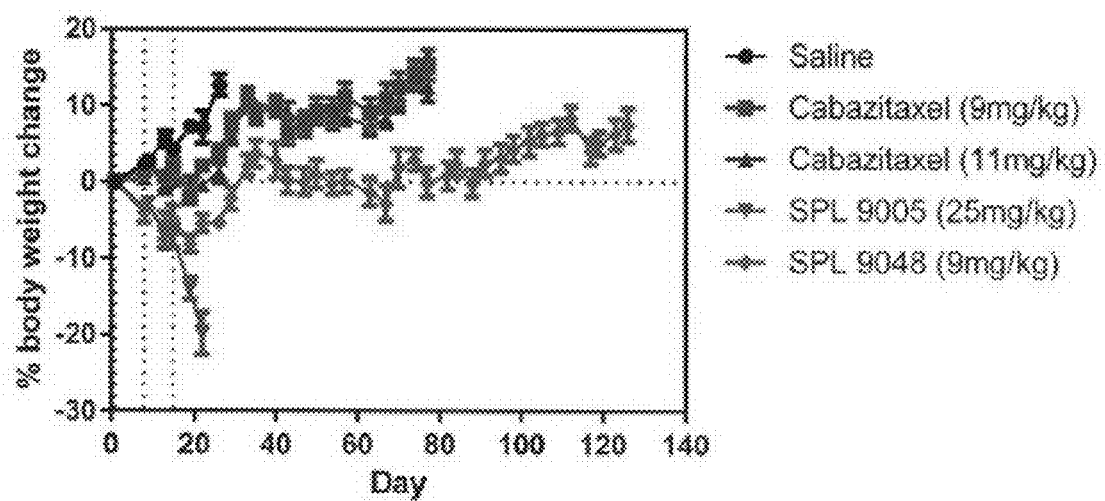
FIG. 2 shows the mean change in body weight in SCID mice following administration of a compound of the present disclosure (SPL9048) and comparator compounds (cabazitaxel, and SPL9005—a comparator cabazitaxel-dendrimer compound) over time in a prostate cancer model study.

FIG. 2 shows the effect of saline, Cabazitaxel, SPL-9005 and SPL-9048 on DU145 tumour-bearing mouse body weight for male mice. Drugs were administered i.v. on days 1, 8 and 15 (indicated by the vertical lines). The data represent the mean percent weight change from baseline (Day 1) for each groups; bars SEM. Graphs are shown for each group until fewer than 6 animals remained in each group.

As shown in FIG. 2, SPL9048 was overall well tolerated in mice (max weight loss was −10% on Day 20; neutral weight loss/gain after Day 40). SPL9048 was also better tolerated than SPL9005 by male mice. For SPL9005, 8/10 male mice had >20% weight loss after administration of a third dose on approx. day 25, but 2/10 male mice recovered to +5/10% starting weight after day 40. However, in a separate study in female SCID mice, when dosed at 25 mg/kg Cabazitaxel equivalent, SPL9005 was better tolerated in female mice with mean weight loss being below 10%, suggesting a possible sex-related difference for this compound.

MDA-MB-231 Mouse Xenograft Breast Cancer Tumour Model Study

A MDA-MB-231 (human breast carcinoma cell line) mouse xenograft breast cancer model study was carried out to assess the anti-tumour efficacy properties of SPL9048 versus free Cabazitaxel.

SPL-9048 was pre-weighed in glass vials and stored at 20° C. until use, and dissolved in saline immediately prior to dosing. Cabazitaxel was prepared fresh for each dosing day. An aliquot of Cabazitaxel concentrate was removed under aseptic conditions and mixed with a 13% ethanol diluent to make up a 10 mg/ml working stock solution. A 1.8 mg/mL dosing solution was prepared from this working stock immediately prior to injection.

Female Balb/c nude mice (age 7 weeks) were inoculated subcutaneously on the flank with $3.5 \times 10^6$ MDA-MB-231 cells in PBS: Matrigel (1:1). Mice were weighed and tumours measured twice weekly using electronic callipers. Tumour volume ($mm^3$) was calculated as length $(mm)/2 \times$ width $(mm)^2$. On day 10 after implantation (referred to as Day 1) mice with similar sized tumours (mean tumour volume 90 $mm^3$) were randomised into 4 groups of 10 animals. Treatment groups were saline, Cabazitaxel (9 mg/kg), SPL-9048 (9 mg/kg) and SPL-9048 (10 mg/kg). All compounds were given intravenously by tail vein injection on days 1, 8 and 15 at 0.1 ml/10 g body weight except Cabazitaxel which was given at 0.05 ml/10 g body weight. Mice received a small dish containing a food supplement (mixed with food dust) daily. The experiment was ended on day 113 or earlier if an ethical endpoint was met.

Figure 3:
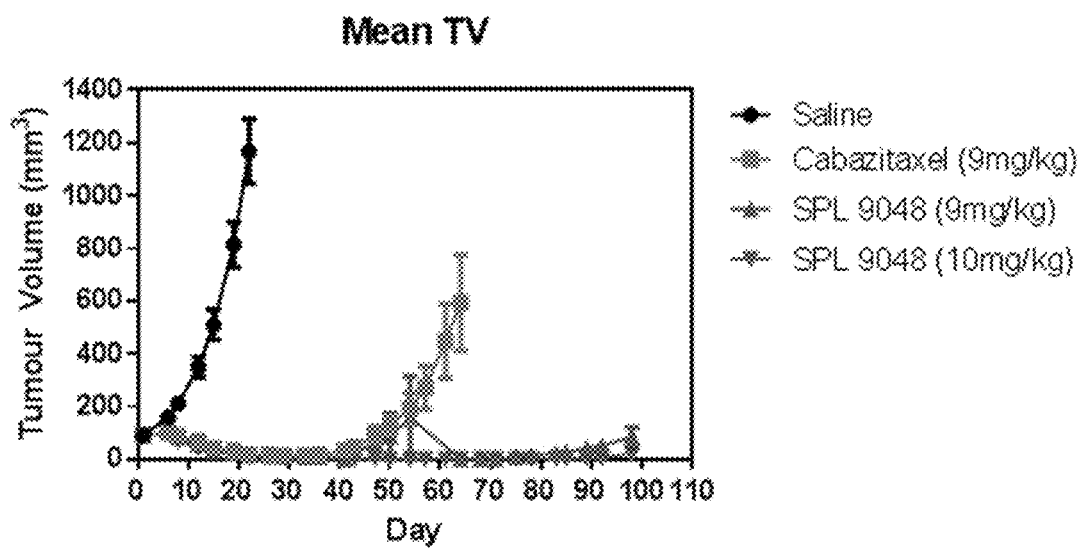
FIG. 3 shows the efficacy of a compound of the present disclosure (SPL9048) and a comparator compound (cabazitaxel) in SCID mice represented by change in mean tumour volume (TV) (mm$^3$) over time in a breast cancer tumour model study.

FIG. 3 shows the antitumour efficacy of the treatments against the MDA-MB-231 tumour xenografts. Tumour volumes were determined twice weekly and were expressed as mean tumour volume (±SEM). Each group initially consisted of 10 mice and graphs are shown until no fewer than 7 animals remained in a group. As shown in FIG. 3, SPL9048 induced complete tumour regression. Tumour regrowth in the Cabazitaxel group was evident by day 43 with 9 of 10 tumours reaching an ethical tumour volume endpoint by day 98. Both doses of SPL-9048 significantly extended survival beyond that of Cabazitaxel.

Figure 4:
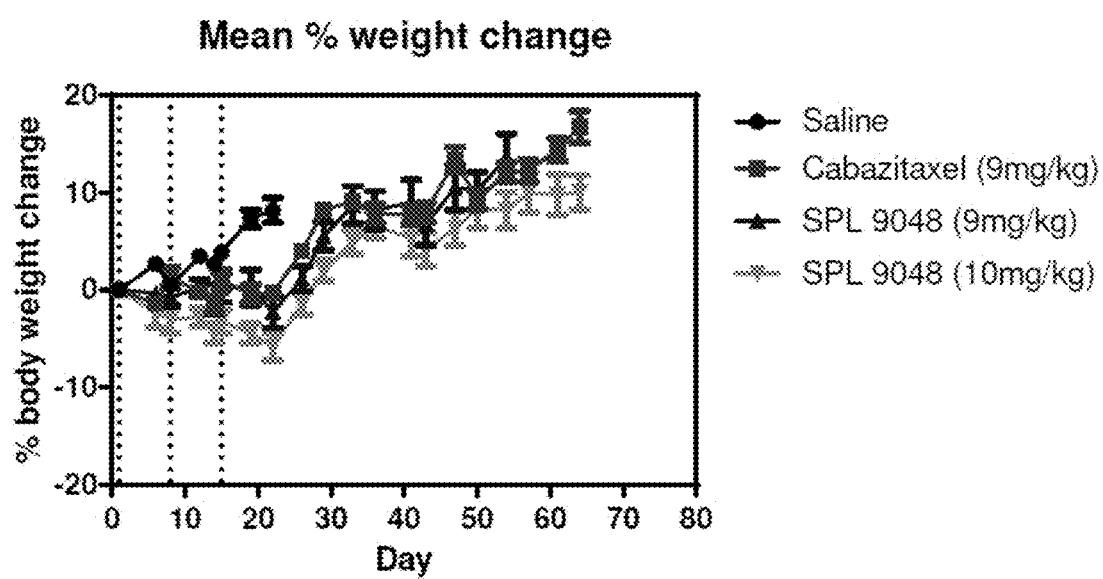
FIG. 4 shows the mean change in body weight in SCID mice following administration of a compound of the present disclosure (SPL9048) and a comparator compound (cabazitaxel) over time in a breast cancer model study.

FIG. 4 shows the effect of saline, Cabazitaxel, and SPL-9048 on MDA-MB-231 tumour-bearing mouse body weight. Each group initially consisted of 10 mice. Drugs were administered i.v. on days 1, 8 and 15 (indicated by the vertical lines). The data represent the mean percent weight change from baseline (Day 1) for each group; bars SEM. Graphs are shown for each group until fewer than 7 animals remained in each group. As shown in FIG. 4, SPL9048 was overall well tolerated and mean weight loss did not exceed 6% in any group.

Example 5: Toxicokinetic/Pharmacokinetic Studies

A single-dose toxicokinetic study of SPL-9048 and SPL-9005 was carried out by intravenous bolus injection in rats with a 21-day observation period. The control, 0.9% sodium chloride, was prepared and dispensed on the day of dosing. SPL-9048 and SPL-9005 were prepared at appropriate concentrations to meet dose level requirements. The dosing formulations were prepared and dispensed on each day of dosing and were used within 3 hours of preparation. The required amount of test article was weighed out and dissolved in a suitable volume of normal saline with gentle swirling and the pH was recorded. Cabazitaxel (JEVTANA® brand cabazitaxel) was prepared at appropriate concentration to meet dose level requirements. The desired amount (1.5 ml) of Cabazitaxel concentrate (40 mg/ml) was aliquoted under aseptic conditions and dissolved in the appropriate volume (4.5 mL) of 13% ethanol diluent between 15° C. and 30° C. to prepare a 10 mg/mL stock solution. This stock solution was further diluted with normal saline to produce the final dosing concentration within 30 minutes.

The animals used were male and female Sprague Dawley Crl:CD (SD) rats. The animals were 10 to 14 weeks old and weighed between 327 and 565 g for males and 212 and 316 g for females at initiation of dosing. Animals were acclimated to their designated housing for at least 4 days before the first day of dosing. Animals were assigned to groups by a stratified randomization scheme designed to achieve similar group mean body weights. Males and females were randomised separately. Animals in poor health or at extremes of body weight ranges were not assigned to groups. PMI Nutrition International Certified Rodent Chow No. 5CR4 was provided ad libitum throughout the study except during designated procedures. The same diet in meal form was also provided, as needed. Municipal tap water, after treatment by reverse osmosis and ultraviolet irradiation, was freely available to each animal via an automatic watering system, except during designated procedures. Water bottles were also provided, as required. Animal were socially housed for psychological/environmental enrichment and were provided with items such as a chewing object, except when interrupted by study procedures/activities. Veterinary care was available throughout the course of the study.

The test and control articles were administered to the appropriate animals at the amounts indicated in the table below via a single intravenous (slow bolus) injection to the tail vein. References to amounts dosed in mg/kg for the dendrimeric compounds SPL-9048 and SPL-9005 are to the amounts of Cabazitaxel that may theoretically be released by the dendrimers.

Animals were observed for 21 days following dose administration. The dose volume for each animal was based on the most recent body weight measurement. The animals were temporarily restrained for dose administration and were not sedated. The doses were given using a syringe with attached needle. The first day of dosing for each group was designated as Day 1. The comparator dosing formulation (JEVTANA® brand Cabazitaxel) and test articles were maintained between 15 and 30° C. during dosing.

| Test Material | Dose Level (Cabazitaxel Equivalents) (mg/kg) | Dose Volume (mL/kg) | Dose Concentration (mg/mL) | Number of Animals Toxicokinetic Study Males |
|---|---|---|---|---|
| SPL9048 | 1 | 1 | 1 | 6 |
| SPL9048 | 2.5 | 1 | 2.5 | 6 |
| SPL9005 | 1 | 1 | 1 | 6 |
| SPL9005 | 2.5 | 1 | 2.5 | 6 |
| JEVTANA® brand Cabazitaxel | 2.5 | 1 | 2.5 | 6 |

Toxicokinetic parameters were estimated using Phoenix pharmacokinetic software. A non-compartmental approach consistent with the intravenous route of administration was used for parameter estimation. All parameters were generated from SPL9048, SPL9005, and JEVTANA® brand cabazitaxel (Cabazitaxel) composite concentrations in plasma whenever practical.

Figure 5:
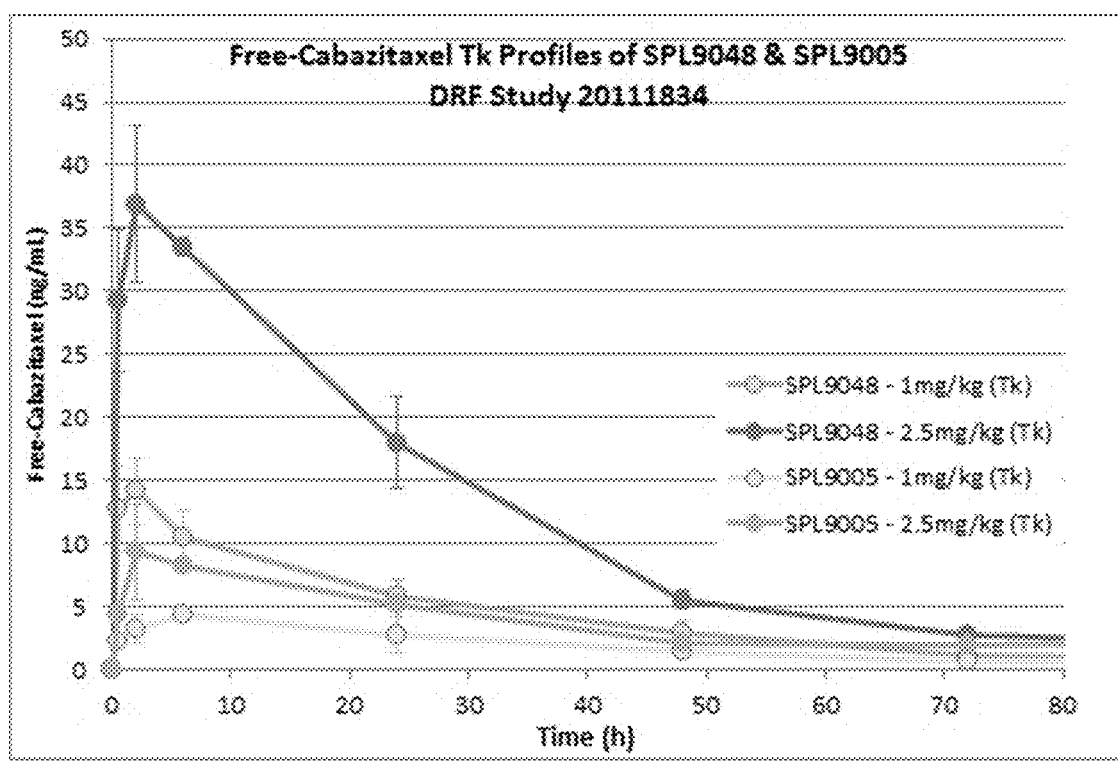
FIG. 5 shows in vivo free-cabazitaxel (released) concentration levels over time following administration to rats of a compound of the present disclosure (SPL9048) and a comparator cabazitaxel-dendrimer compound (SPL9005).

The table below and FIG. 5 provide details regarding the pharmacokinetic parameters for free Cabazitaxel following administration of SPL9048 (a Cabazitaxel-containing dendrimer of the present disclosure, or comparator compounds, i.e. SPL9005 (a different Cabazitaxel-containing dendrimer) and JEVTANA® brand cabazitaxel (Cabazitaxel).

| Treatment | Dose Level (drug eq., mg/kg) | Sex | $C_{max}$ (ng/mL) | $T_{max}$ (h) | $AUC_{0-t}$ (ng · h/mL) | % JEVTANA® brand cabazitaxel dose |
|---|---|---|---|---|---|---|
| SPL9048-1 mg/kg (Tk) | 1 | Males | 14.13 | 2 | 445.00 | 65 |
| SPL9048-2.5 mg/kg (Tk) | 2.5 | Males | 36.89 | 6 | 1239.99 | 182 |
| SPL9005-1 mg/kg (Tk) | 1 | Males | 4.41 | 6 | 202.94 | 30 |
| SPL9005-2.5 mg/kg (Tk) | 2.5 | Males | 9.29 | 2 | 548.96 | 81 |
| JEVTANA® brand cabazitaxel (cabazitaxel)-2.5 mg/kg (Tk) | 2.5 | Males | 801.05 | 2 min | 679.99 | 100 |

The free Cabazitaxel plasma profile for SPL9005 and SPL9048 was distinctly different from that for JEVTANA® brand cabazitaxel. The results show that administration of SPL9048 at 2.5 mg/kg resulted in a $C_{max}$ value of 36.89 ng/mL, a $T_{max}$ value of 6 hours, and an area under the curve (AUC) of 1239.99 ng·h/mL. Administration of SPL9005 at 2.5 mg/kg resulted in a $C_{max}$ of 9.29 ng/mL, a $T_{max}$ of 2 hours, and an AUC of 548.96 ng·h/mL. Administration of JEVTANA® brand cabazitaxel at 2.5 mg/kg resulted in a $C_{max}$ value of 801.05 ng·h/mL, a $T_{max}$ of 2 min and an AUC of 679.99 ng h/mL. For the JEVTANA® brand cabazitaxel group, Cabazitaxel was not measurable more than 24 hours after JEVTANA® brand cabazitaxel administration.

Thus, administration of SPL9048 results in reduced risk of side effects or toxicity compared with JEVTANA® brand cabazitaxel due to the considerably lower $C_{max}$. Administration of SPL9048 also resulted in increased overall exposure to Cabazitaxel compared to JEVTANA® brand cabazitaxel, as shown by the AUC values in the above table. Both SPL-9048 and SPL-9005 have a lower Cabazitaxel $C_{max}$ than administration of a comparable amount of JEVTANA® brand cabazitaxel. However, the amount of free Cabazitaxel delivered by SPL9048 over the time course of the study was higher than that delivered by a comparable dose of SPL9005 (i.e. containing an equivalent amount of Cabazitaxel), as demonstrated by the AUC levels (see Table and FIG. 4). SPL9048 demonstrated an excellent pharmacokinetic profile consistent with reduced likelihood of side effects and increased efficacy at equivalent dose.

Example 6: Toxicology Studies

Toxicology studies in rats were carried out comparing the effects of SPL9048 and free Cabazitaxel (JEVTANA® brand cabazitaxel).

SPL9048 and JEVTANA® brand cabazitaxel were dosed at 1 mg/kg to rats, n=6 (3 males, 3 females). References to amounts dosed in mg/kg for the dendrimeric compound are to the amounts of Cabazitaxel that may theoretically be released by the dendrimer.

Figure 6:
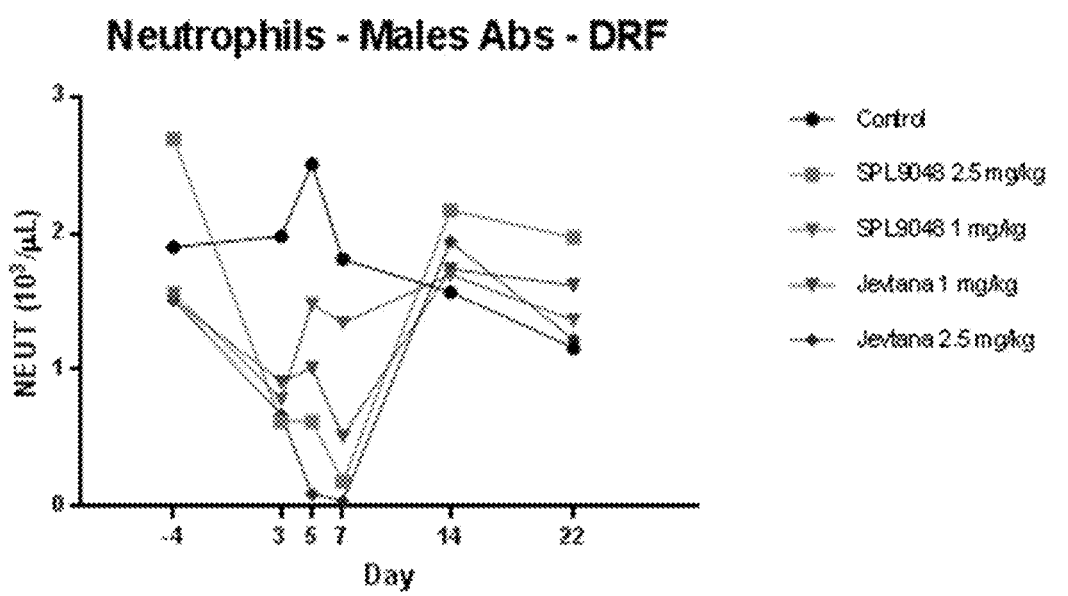
FIG. 6 shows the results of a neutropenia toxicity study data for both male and female rats, following administration of a compound of the present disclosure (SPL9048) and a comparator compound (JEVTANA® brand of cabazitaxel).
Figure 6:
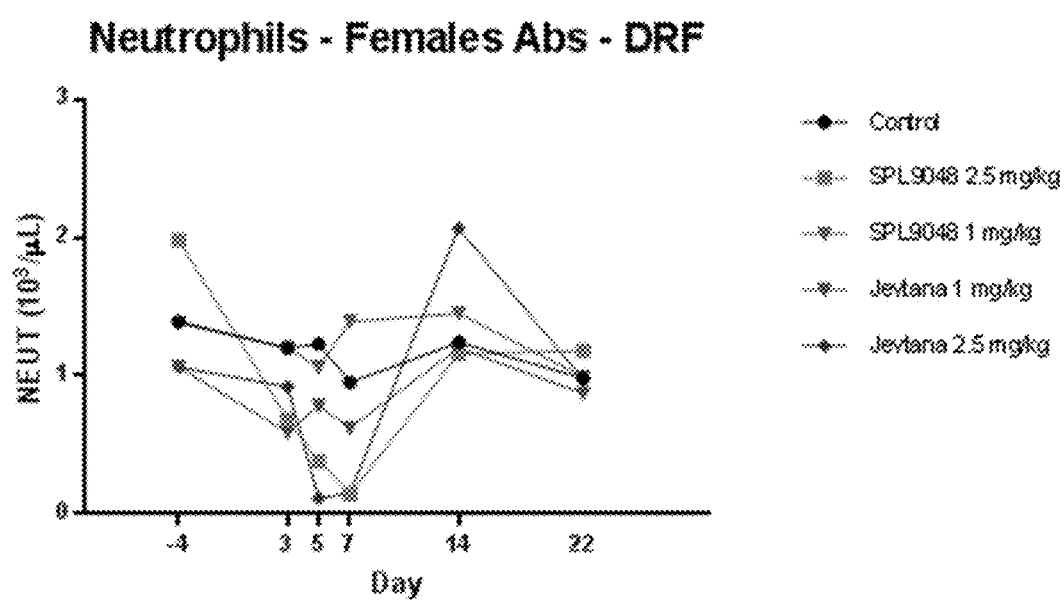

As shown in FIG. 6, the results show that there is a separation in neutropenia at this dosage level (1 mg/kg) in both male and female rats, as evidenced by the dip in values seen with the administration of JEVTANA® brand cabazitaxel (i.e. Cabazitaxel) and a lesser/no dip in values observed following administration of SPL9048 (see day 7 in particular). The rebound after day 7 appears to depend on the severity of neutropenia, as would be expected. In the 1 mg/kg JEVTANA® brand cabazitaxel (i.e., free Cabazitaxel) groups, there is a substantial rebound at day 14, whereas there is virtually no rebound in the 1 mg/kg SPL9048 groups (or controls), which is consistent with limited neutropenia in these groups. This indicates that SPL9048 is likely to induce less neutropenia, and therefore be less toxic in the clinic, compared with the administration of an equivalent dose of free Cabazitaxel.

Similar results were also found in a study at which SPL9048 and JEVTANA® brand cabazitaxel were delivered at 2.5 mg/kg active agent. SPL9048 was found to be less neutropenic at day 5 than JEVTANA® brand cabazitaxel. Reduced toxicity was observed for SPL9048 compared to JEVTANA® brand Cabazitaxel. Test article related-hematology changes (decreases in white blood cells, neutrophils, lymphocytes, monocytes, eosinophil, platelets, and reticulocytes) were noted at 2.5 mg/kg SPL9048 and 2.5 mg/kg JEVTANA® brand cabazitaxel by Day 2 in males and females and remained low through Day 7. The decreases in these parameters were generally greater in rats administered 2.5 mg/kg JEVTANA® brand cabazitaxel.

Treatment-related microscopic changes were observed in the thymus, bone marrow, and spleen in animals administered SPL9048 at 2.5 mg/kg and JEVTANA® brand cabazitaxel at 2.5 mg/kg; the severity of the bone marrow and thymus findings was generally greater in JEVTANA® brand cabazitaxel-treated rats.

Example 7: Comparative Linker Release Rates in PBS at 37° C. and pH 7.4

A study was carried out to determine the rate of Cabazitaxel release from certain dendrimeric compounds in PBS (phosphate-buffered saline) at 37° C. and pH 7.4. The compounds tested were:

i) compounds of the present disclosure, SPL9048 and SPL9049 (BHALys[Lys]$_{32}$[α-DGA-Cabazitaxel]$_{32\dagger}$[Σ-PEG$_{~1100}$]$_{32\ddagger}$. SPL9049 differs from SPL9048 in that it contains lower molecular weight PEG groups; and ii) comparator Cabazitaxel-containing dendrimeric compounds, SPL9005 and SPL9006 (SPL9006 differs from SPL9048 in that it contains MIDA (Methyliminodiacetyl) linking groups in place of diglycolyl linking groups (i.e. —N(Me)— in place of —O— present in the diglycolyl linker. SPL9006 was prepared by analogous synthetic methods to those used for the preparation of SPL 9048).

Results indicating the % Cabazitaxel released at 24 hours for two repeat experiments are shown in the table below, together with the mean time to 50% release (or estimated mean time to 50% release based on datapoints):

% of Cabazitaxel released in PBS at 37° C. and pH 7.4:

|  | % API released at 24 hours (Exp #1) | % API released at 24 hours (Exp #2) | Time to 50% release (mean) (Exp #2) |
|---|---|---|---|
| SPL9005 | 11.9 | 15 | Estimated at 5-7 days |
| SPL9006 | 7.5 | 8 | Estimated at 6-8 days |
| SPL9048 | 37 | 41 | 36 hours |
| SPL9049 | 51.5 | 32 | 54 hours |

Data for SPL9048 and SPL9049 at additional timepoints in Exp #2 is also provided below:

% of Cabazitaxel released in PBS at 37° C. and pH 7.4:

| time (h) | SPL9049 | SPL9048 |
|---|---|---|
| 0 | 0.97 | 0.95 |
| 24 | 32.06 | 41.28 |
| 48 | 45.156 | 55.48 |
| 67 | 59.676 | 62.65 |
| 87 | 67.86 | 71.12 |

The results demonstrate the relative release rates of Cabazitaxel from the dendrimer following administration. The comparator SPL9005 results in the release of about 12 to 15% Cabazitaxel over 24 hours in PBS at 37° C. and pH 7.4, the comparator SPL9006 (MIDA linker) results in the release of about 8% Cabazitaxel in PBS at 37° C. and pH 7.4 over the same time period, the compound of the present disclosure SPL9048 results in the release of about 40% Cabazitaxel in PBS at 37° C. and pH 7.4 over a 24-hour period, and SPL9049 results in the release of about 30 to 50% Cabazitaxel under the same conditions.

SPL9048 has also been observed to have increased stability in solution (e.g. with regard to precipitation) compared with SPL9049, which may be attributed to the conjugate containing a PEG$_{2200}$ group rather than a PEG$_{1100}$ group. Alongside the excellent efficacy, toxicokinetic and pharmacokinetic properties observed for SPL9048, this property is a further advantage for that drug-dendrimer conjugate.

Example 8: Stability of Citric Acid Drug-Dendrimer Conjugate Composition

A study conducted on drug release on dendrimer molecules containing a different pharmaceutical agent, in 0.1M citric acid at pH 3.5 to 6.5 identified greatest stability over 7 days at pH 4.5 at room temperature and 4 degrees Celsius. The optimal range was 3.5 to 5.5 with less than 0.3% and 0.1% release at RT and 4 C respectively. Another study was conducted to evaluate 10 different inhibitors of drug release on dendrimer molecules containing a different pharmaceutical agent in dog, mouse and human plasma. Citric acid was identified as the most effective inhibitor of drug release.

Example 9: Comparison of SPL9048 to ABRAXANE® and Gemcitabine

A CAPAN-1 (human pancreatic adenocarcinoma cell line) mouse xenograft pancreatic cancer model study was carried out to assess the anti-tumour efficacy properties of SPL9048 compared to ABRAXANE® (albumin bound paclitaxel), alone or in combination with Gemcitabine.

SPL9048 and Cabazitaxel were prepared as described above. Gemcitabine and ABRAXANE® were obtained from the Peter MacCallum Cancer Centre pharmacy, and were dissolved in saline solution immediately prior to dosing.

Female NOD-SCID Interleukin-2 receptor gamma chain null mice (aged 9 weeks) were inoculated subcutaneously on the flank with 5×10$^6$ CAPAN-1 cells in PBS:Matrigel (1:1). Mice were weighed and tumours measured twice weekly using electronic callipers. Tumour volume (mm$^3$) was calculated as length (mm)/2× width (mm)$^2$. On day twenty-six after implantation, mice with similar sized tumours (mean tumour volume 100 mm$^3$) were randomised into 8 groups of 9 animals.

ABRAXANE® and SPL9048 were administered via tail vein i.v. injection, and gemcitabine was administered by i.p. injection on days 1, 8 and 15 at 0.1 ml/10 g body weight. The experiment was ended on day 107 or earlier if an ethical endpoint was met. One mouse died immediately after injection with ABRAXANE® on day 1 due to an injection error. All other treatments were well tolerated with no weight loss. Tumour growth data was analysed in GraphPad Prism for ANOVA followed by Dunnett's post ad-hoc test. Groups were dosed as follows:
1. Saline–vehicle
2. Gemcitabine (80 mg/kg, i.p.)–vehicle (saline)
3. ABRAXANE® (40 mg/kg, i.v.)–vehicle
4. ABRAXANE® (40 mg/kg, i.v.)+Gemcitabine (80 mg/kg, i.p.)
7. SPL9048 (7.5 mg/kg, i.v.)–vehicle
8. SPL9048 (7.5 mg/kg, i.v.)+Gemcitabine (80 mg/kg, i.p.)

Figure 7:
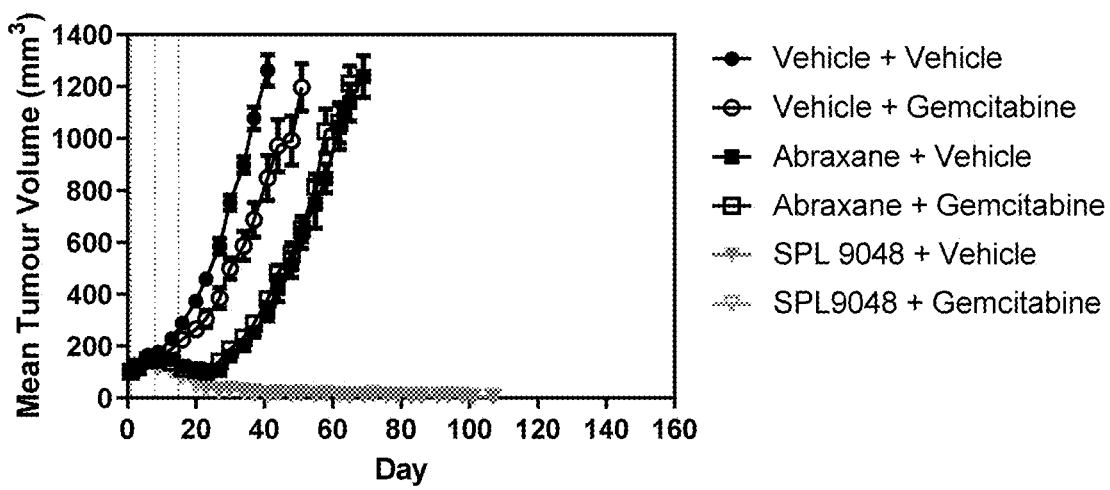
FIG. 7 shows the efficacy of a compound of the present disclosure (SPL9048) when dosed alone and in combination with gemcitabine in comparison with comparators gemcitabine, abraxane, and a combination of gemcitabine and abraxane, in female NOD-scid Interleukin 2 receptor gamma chain null mice, represented by change in mean tumour volume (TV) (mm$^3$) over time in a pancreatic cancer model study.

FIG. 7 shows the anti-tumour efficacy of the treatments against the CAPAN-1 tumour xenografts. Tumour volumes were determined twice weekly and are expressed as mean tumour volume (±SEM). As shown in FIG. 7, SPL9048, given alone or in combination with Gemcitabine, induced complete regression of CAPAN-1 tumours for the duration of the study. Neither Gemcitabine or ABRAXANE® were effective in this model. SPL9048 treatment inhibited CAPAN-1 tumour growth more effectively than ABRAXANE® (P=0.004, ABRAXANE® vs SPL-8732; P<0.0001 Mantel Cox regression analysis of Kaplan-Meier survival curves).

ABRAXANE®, administered alone and in combination with Gemcitabine, inhibited CAPAN-1 tumour growth to a similar extent (percent tumour growth inhibition on Day 37=85% and 81%, respectively; Table 2). SPL9048 significantly extended survival beyond that of Gemcitabine or ABRAXANE®.

| Treatment | Tumour Growth inhibition (%) | P (vs vehicle) |
|---|---|---|
| Gemcitabine | 40 | <0.0001 |
| ABRAXANE ® | 85 | <0.0001 |

| Treatment | Tumour Growth inhibition (%) | P (vs vehicle) |
|---|---|---|
| SPL9048 | 107 | <0.0001 |
| ABRAXANE ® + Gemcitabine | 81 | <0.0001 |
| SPL9048 + Gemcitabine | 109 | <0.0001 |

Analysis was performed on Day 37, the last day all vehicle treated animals remained in the study.

Example 10: Phase 1 Clinical Study—PK and Biomarkers

A phase 1 dose escalation study was conducted to determine appropriate dosages of SPL9048. Biomarker, PK and other data were collected from patients enrolled in the study. Patients were dosed every 3 weeks, over 1 hour using an infusion pump. Patients all had progressive metastatic disease. The patient population was heavily pre-treated with a range of chemotherapeutic agents as described in the below table.

| Prior Medicaments | Cancer Type |
|---|---|
| Androgen deprivation therapy | Prostate |
| Luteinizing hormone-releasing hormone agonist | |
| Bicalutamide | |
| Enzalutamide | |
| Docetaxel (up to two cycles) | |
| Docetaxel/G-CSF (up to six cycles) | |
| Carboplatin/Paclitaxel/Bevacizumab (one cycle) | Ovarian |
| Carboplatin/Paclitaxel (up to seven cycles) | |
| Bevacizumab (up to 18 cycles) | |
| Gemcitabine/Carboplatin | |
| Niraparib | |
| FOLFIRINOX ® (folinic acid/fluorouracil/irinotecan/oxaliplatin) (up to 10 cycles) | Pancreatic |
| Gemcitabine/Capecitabine (up to two cycles) | |
| Gemcitabine/Abraxane (up to 16 cycles) | |
| Gemcitabine (up to two cycles) | |

Figure 8:
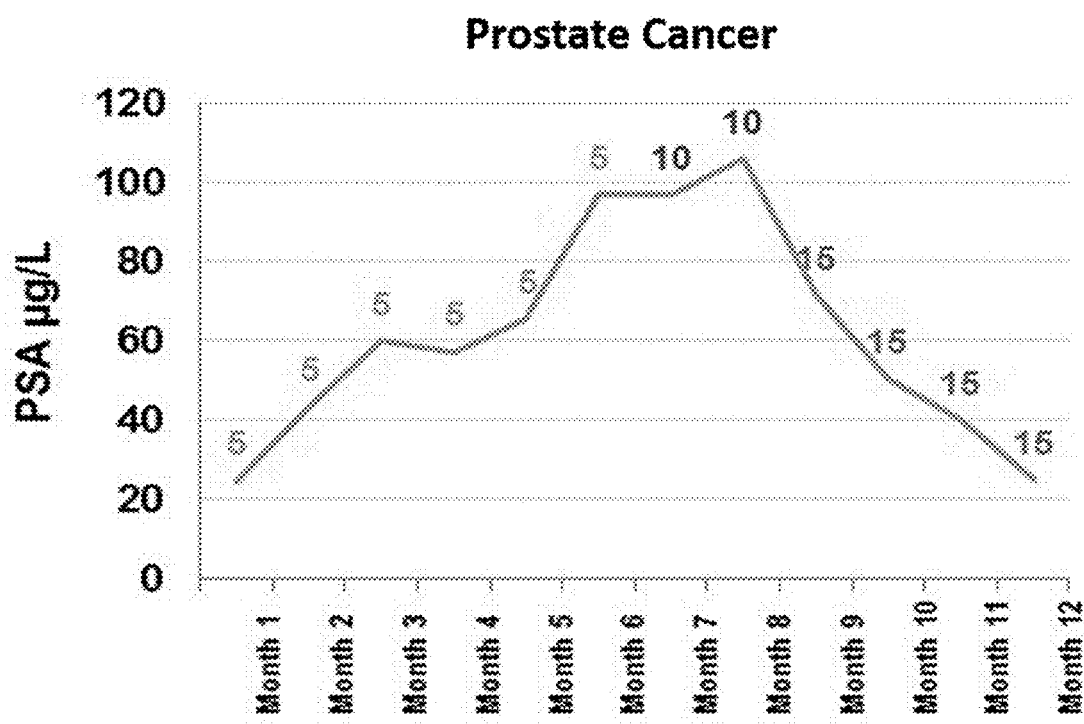
FIG. 8 shows the levels of a prostate cancer biomarker PSA (μg/L) in a patient having prostate cancer over time.
Figure 9:
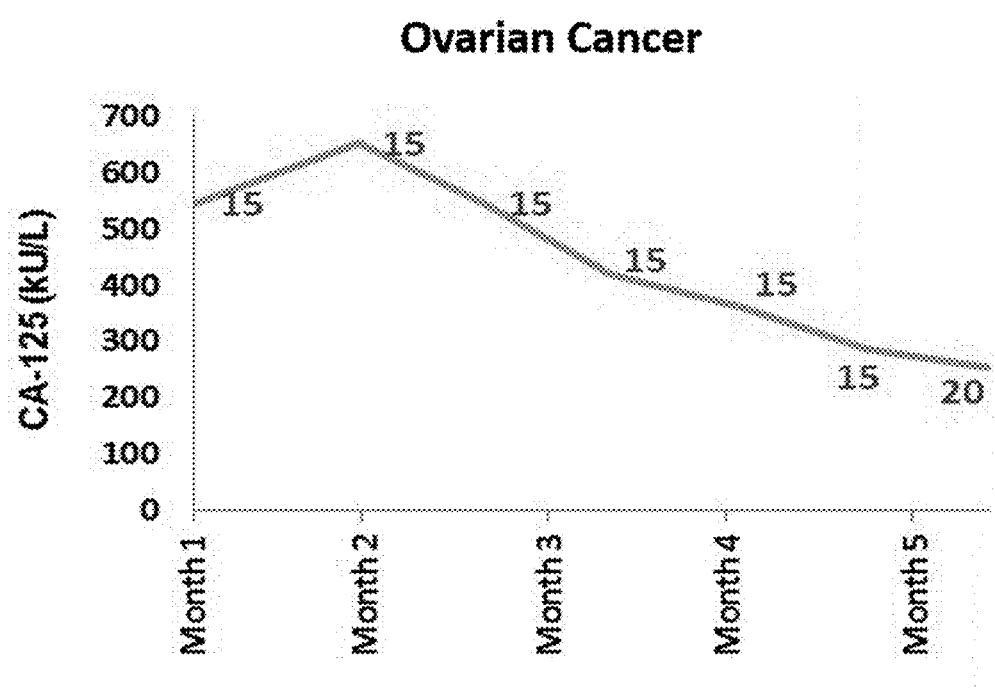
FIG. 9 shows the levels of an ovarian cancer biomarker CA-125 (μg/L) in a patient having ovarian cancer over time.

The data in FIGS. 8 and 9 shows that the biomarker response occurs at doses of SPL9048 as low as 10 mg/m$^2$. FIG. 8 shows PSA, a prostate cancer marker, declining in prostate cancer patients after multiple doses at 10 mg/m$^2$ and continuing at 20 mg/m$^2$ Cabazitaxel equivalents. FIG. 9 shows CA-125, an ovarian cancer marker, declining after two doses at 15 mg/m$^2$. These are important signs of efficacy.

The following table identifies the patients of the study, many showing signs of stable disease.

| Dose Range (mg/m$^2$ Cabazitaxel) | No. of Cycles | Tumour Type (stage at screening) | Positive Treatment Response |
|---|---|---|---|
| 2 to 15 | 12 | Digital papillary adenocarcinoma (stage IV) | Stable disease >33 weeks. |
| 5 to 20 | 13 | Prostate (stage III) | Stable disease >35 weeks. PSA declined from 106 to 25 µg/L (over 12 weeks). (see FIG. 7) |
| 15 to 20 | 7 | Ovarian (stage IV) | CA-125 declining (60%) from 652 to 255 kU/L (over 15 weeks) after one cycle at 15 mg/m$^2$ dose. (see FIG. 8) |
| 20 | 5 | Prostate | PSA declined (67%) from 262 to 86 µg/L (in 3 weeks) after three cycles, following rising PSA. Preliminary signs of PSA stability at 5 mg/m$^2$. Stable disease >6 weeks |
| 20 | 1 | Pancreatic adenocarcinoma | Stable CA 19-9, abdominal pain subsided and cessation of opioid treatment after one cycle. |
| 20 | 3 | Pancreatic adenocarcinoma (stage IV) | CA 19-9 declining (28%) from 177 baseline to 127 kU/L after one cycle. |

Pharmacokinetic data relating to the free Cabazitaxel from the study is shown in the Table below. In summary, after administration with SPL9048, free Cabazitaxel $C_{max}$ is about 3- to 10-fold less than JEVTANA® brand cabazitaxel at equivalent Cabazitaxel dose of 20 mg/m$^2$. $C_{max}$ at 20 mg/ml Cabazitaxel equivalents in the three patients was measured as 53.6, 15.8, and 17.6 ng/ml.

| Free Cabazitaxel | Dose (mg/m$^2$ Cabazitaxel equivalents) | $C_{max}$ (ng/ml) | AUCinf (ng/ml*h) | $T_{1/2}$ (terminal) (h) |
|---|---|---|---|---|
| SPL9048 (JEVTANA ® brand cabazitaxel) | 15 | 15; 11 (137) | 1370; 1700 (569) | 195; 107 (90) |
| SPL9048 (JEVTANA ® brand cabazitaxel) | 20 | 53.6; 15.8; 17.6 (183) | 745; 1020 (759) | 48; 81 (90) |

Pharmacokinetic data relating to the total Cabazitaxel (i.e free Cabazitaxel and dendrimer-bound Cabazitaxel) from the study is shown in the Table below. In summary, the total Cabazitaxel AUCinf after administration with SPL9048 is about 2000 to 4000 times greater than JEVTANA® brand cabazitaxel at equivalent Cabazitaxel dose.

| Total Cabazitaxel | Dose (mg/m$^2$) | $C_{max}$ (ng/ml) | AUCinf (ng/ml*h) | $T_{1/2}$ (terminal) (h) |
|---|---|---|---|---|
| SPL9048 (JEVTANA ® brand cabazitaxel) | 15 | 8020; 8610 (137) | 176,000; 182,000 (569) | 116; 15 (90) |
| SPL9048 (JEVTANA ® brand cabazitaxel) | 20 | 8,050; 10,100 (183) | 159,000; 222,000 (759) | 12; 13 (90) |

JEVTANA ® brand cabazitaxel numbers calculated using model described in Ferron G., et al Cancer Chemo Pharma (2013) 71: 681-692.

The invention claimed is:
1. A dendrimer comprising:
i) wherein the core is:

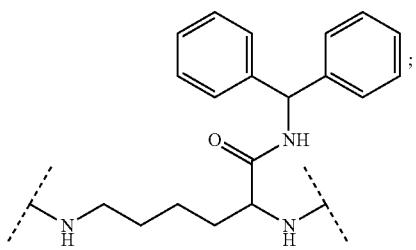

and
ii) building units (BU), wherein the building units are each:

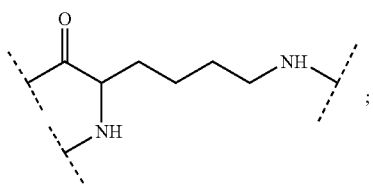

wherein the acyl group of each building unknit provides a covalent attachment point for attachment to the core or to a previous generation building unit; and wherein each nitrogen atom provides a covalent attachment point for covalent attachment to a subsequent generation building unit, a first terminal group, or a second terminal group;
wherein the core unit is covalently attached to two building units via amide linkages, each amide linkage being formed between a nitrogen atom present in the core unit and the carbon atom of an acyl group present in a building unit;
the dendrimer being a five generation building unit dendrimer;
wherein building units of different generations are covalently attached to one another via amide linkages formed between a nitrogen atom present in one building unit and the carbon atom of an acyl group present in another building unit;
the dendrimer further comprising:
iii) a plurality of first terminal groups (T1) each comprising a cabazitaxel residue covalently attached to a diglycolyl linker group; and
iv) a plurality of second terminal groups (T2) each comprising a PEG group having an average molecular weight in the range of from 1000 to 2500 Daltons;
wherein at least one third of the nitrogen atoms present in outer building units are each covalently attached to a first terminal group; and
at least one third of the nitrogen atoms present in outer building units are each covalently attached to a second terminal group;
or a pharmaceutically acceptable salt thereof.

2. A dendrimer as claimed in claim 1, wherein the building units are each:

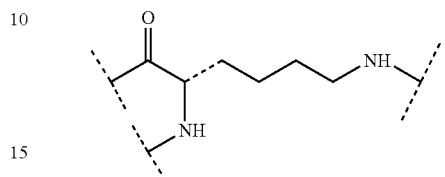

3. A dendrimer as claimed in claim 1, wherein the dendrimer has five complete generations of building units.

4. A dendrimer as claimed in claim 1, wherein each first terminal group (T1) is:

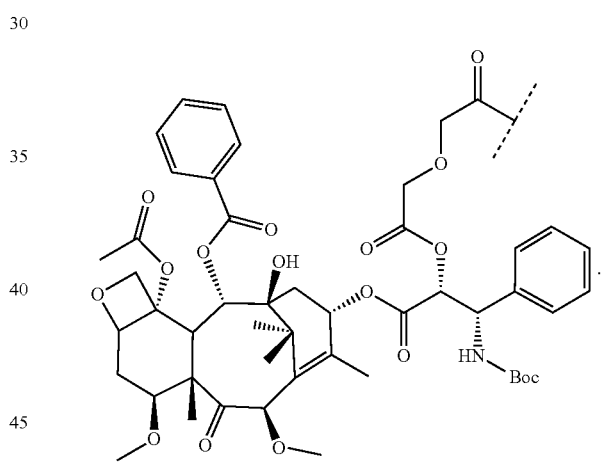

5. A dendrimer as claimed in claim 1, wherein the second terminal groups are each

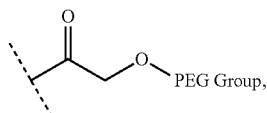

and wherein the PEG group is a methoxy-terminated PEG.

6. A dendrimer as claimed in claim 5, wherein the dendrimer comprises surface units comprising an outer building unit attached to a first terminal group and a second terminal group, the surface units having the structure:

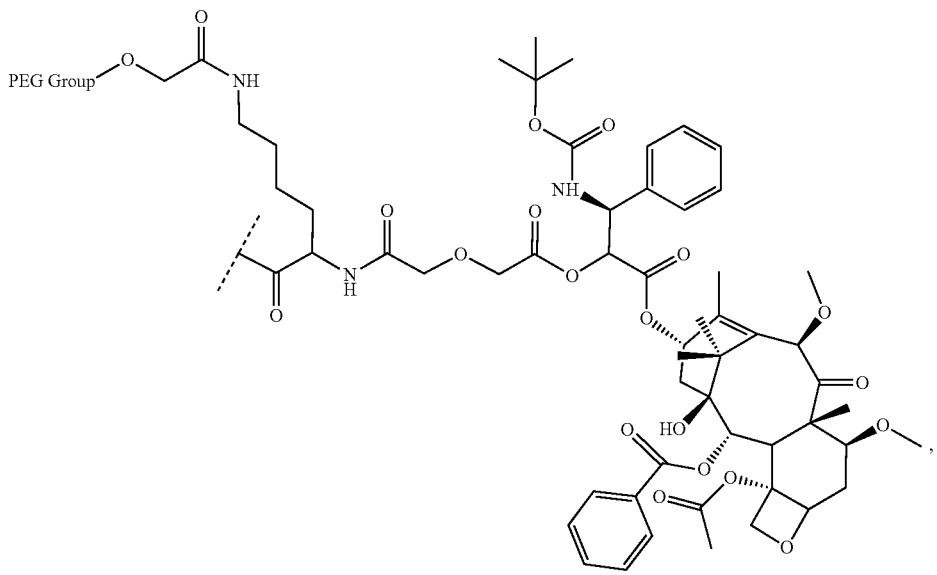

and wherein the PEG group is a methoxy-terminated PEG having an average molecular weight in the range of from about 1750 to 2500 Daltons.

7. A dendrimer as claimed in claim 6, wherein the dendrimer has from 28 to 32 surface units.

8. A dendrimer as claimed in claim 1, wherein at least 40% of the nitrogen atoms present in the outer building units are each covalently attached to a first terminal group; and at least 40% of the nitrogen atoms present in the outer building units are each covalently attached to a second terminal group.

9. A dendrimer as claimed in claim 1, wherein the five generations of building units are complete generations, and wherein the outer generation of building units provides 64 nitrogen atoms for covalent attachment to a first terminal group or a second terminal, wherein from 26 to 32 first terminal groups are covalently attached to one of said nitrogen atoms, and wherein from 28 to 32 second terminal groups are each covalently attached to one of said nitrogen atoms.

10. A dendrimer as claimed in claim 1, wherein the cabazitaxel residues comprise a w/w % of the dendrimer in the range of from 23% w/w to 28% w/w.

11. A dendrimer as claimed in claim 1, wherein the dendrimer is:

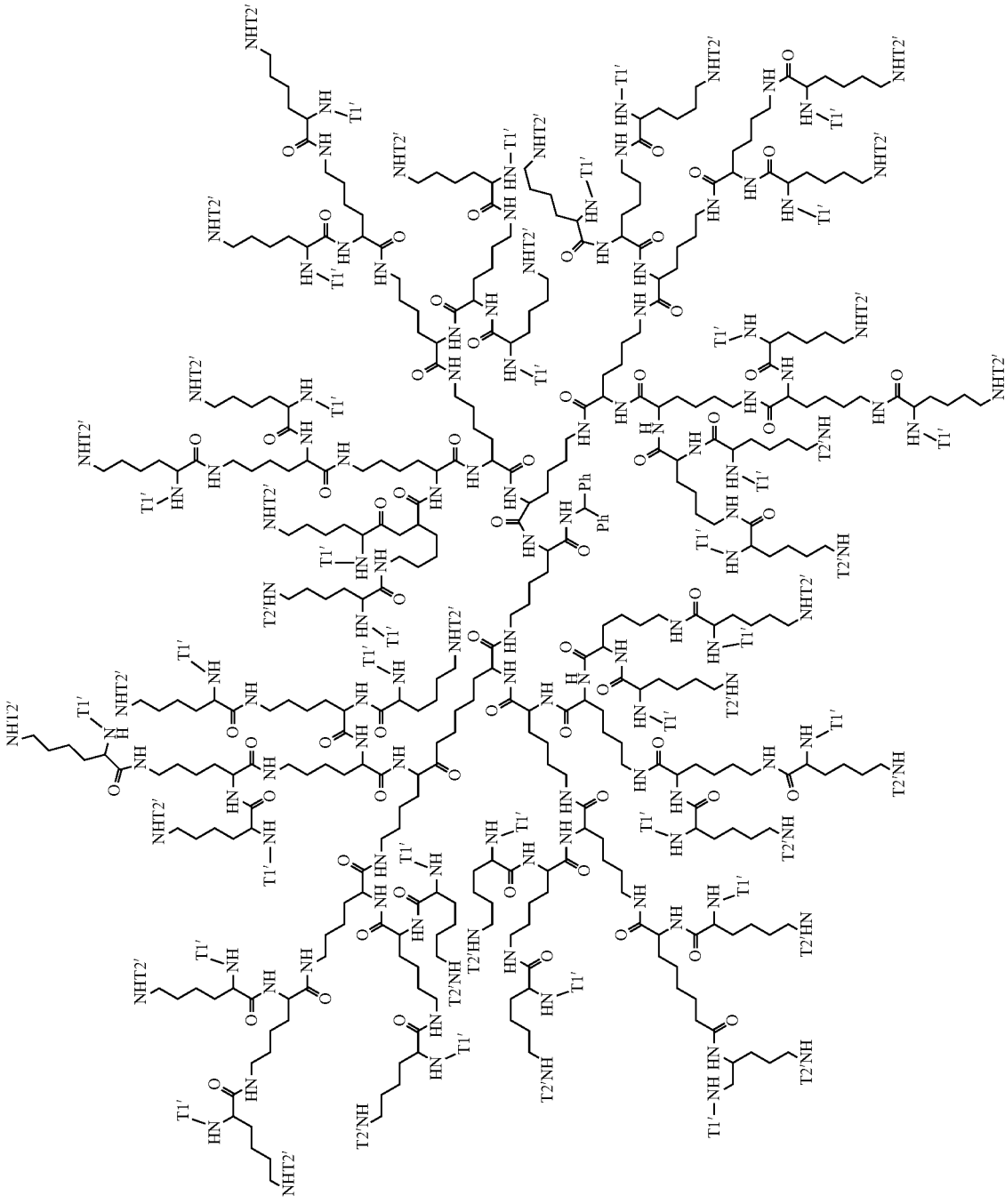

in which T1' represents a first terminal group which is

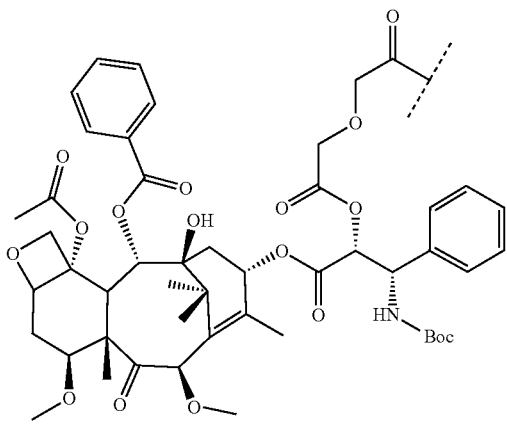

or T1' represents H, wherein less than 5 of T1' are H; and T2' represents a second terminal group which is

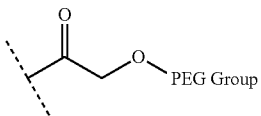

wherein the PEG group is a methoxy-terminated PEG having an average molecular weight in the range of from about 1750 to 2500 Daltons, or T2' represents H, and wherein less than 5 of T2' are H.

12. A dendrimer as claimed in claim 1, wherein the in vitro half-life for cabazitaxel release from the dendrimer in PBS at pH 7.4 and at 37° C. is in the range of from 30 to 60 hours.

13. A pharmaceutical composition comprising:
i) a dendrimer as claimed in claim 1, or a pharmaceutically acceptable salt thereof, and
ii) a pharmaceutically acceptable excipient.

14. A pharmaceutical composition as claimed in claim 13, wherein the composition is a solid composition comprising a dendrimer as claimed in claim 1, a sugar and an acid, and wherein the composition is for reconstitution with a diluent.

15. A pharmaceutical composition as claimed in claim 14, wherein the sugar is trehalose and the acid is citric acid.

16. A pharmaceutical composition as claimed in claim 14, wherein, following reconstitution with a diluent, the reconstituted composition has a pH in the range of from 3.5 to 5.5.

17. A pharmaceutical composition as claimed in claim 13, wherein the composition is free or substantially free of polyethoxylated castor oil and polyethoxylated sorbitan monooleate.

18. A pharmaceutical composition as claimed in claim 13, wherein the composition is formulated for administration as an infusion over a time period of up to 30 minutes, or wherein the composition is formulated for administration as a bolus over a time period of up to 5 minutes.

\* \* \* \* \*

UNITED STATES PATENT AND TRADEMARK OFFICE
CERTIFICATE OF CORRECTION

| | | |
|---|---|---|
| PATENT NO. | : 11,118,016 B2 | Page 1 of 1 |
| APPLICATION NO. | : 17/003699 | |
| DATED | : September 14, 2021 | |
| INVENTOR(S) | : David James Owen et al. | |

It is certified that error appears in the above-identified patent and that said Letters Patent is hereby corrected as shown below:

In the Claims

At Column 81, Claim 1, Line 3, please replace:
"wherein the core is:"
With:
-- a core unit (C), wherein the core is: --

At Column 81, Claim 1, Line 39, please replace:
"unknit"
With:
-- unit --

Signed and Sealed this
Twenty-eighth Day of May, 2024

*Katherine Kelly Vidal*

Katherine Kelly Vidal
*Director of the United States Patent and Trademark Office*